(12) United States Patent
Pelcman

(10) Patent No.: US 11,357,757 B2
(45) Date of Patent: Jun. 14, 2022

(54) HETEROARYL SUBSTITUTED BETA-HYDROXYETHYLAMINES FOR USE IN TREATING HYPERGLYCAEMIA

(71) Applicant: ATROGI AB, Stockholm (SE)

(72) Inventor: Benjamin Pelcman, Stockholm (SE)

(73) Assignee: ATROGI AB, Stockholm (SE)

( * ) Notice: Subject to any disclaimer, the term of this patent is extended or adjusted under 35 U.S.C. 154(b) by 0 days.

(21) Appl. No.: 16/645,286

(22) PCT Filed: Sep. 13, 2018

(86) PCT No.: PCT/GB2018/052595
§ 371 (c)(1),
(2) Date: Mar. 6, 2020

(87) PCT Pub. No.: WO2019/053427
PCT Pub. Date: Mar. 21, 2019

(65) Prior Publication Data
US 2021/0030731 A1    Feb. 4, 2021

(30) Foreign Application Priority Data

Sep. 13, 2017 (GB) .................................. 1714745

(51) Int. Cl.
| | | |
|---|---|---|
| A61K 31/4412 | (2006.01) | |
| A61P 3/10 | (2006.01) | |
| A61K 31/426 | (2006.01) | |
| A61K 31/44 | (2006.01) | |
| A61K 31/505 | (2006.01) | |
| A61K 45/06 | (2006.01) | |
| C07D 213/38 | (2006.01) | |
| C07D 213/64 | (2006.01) | |
| C07D 239/36 | (2006.01) | |
| C07D 277/24 | (2006.01) | |

(52) U.S. Cl.
CPC ........ *A61K 31/4412* (2013.01); *A61K 31/426* (2013.01); *A61K 31/44* (2013.01); *A61K 31/505* (2013.01); *A61K 45/06* (2013.01); *A61P 3/10* (2018.01); *C07D 213/38* (2013.01); *C07D 213/64* (2013.01); *C07D 239/36* (2013.01); *C07D 277/24* (2013.01)

(58) Field of Classification Search
None
See application file for complete search history.

(56) References Cited

U.S. PATENT DOCUMENTS

| | | |
|---|---|---|
| 2,308,232 A | 1/1943 | Scheuing et al. |
| 2,460,144 A | 1/1949 | Moore |
| 3,056,836 A | 10/1962 | Hendrik |
| 3,341,594 A | 9/1967 | Otto et al. |
| 3,410,944 A | 11/1968 | Claassen et al. |
| 3,801,631 A | 4/1974 | Comer et al. |
| 3,910,934 A | 10/1975 | Sankey et al. |
| 3,952,101 A | 4/1976 | Jen et al. |
| 3,954,871 A | 5/1976 | Buu-Hoi et al. |
| 3,985,887 A | 10/1976 | Kaiser et al. |
| 4,024,156 A | 5/1977 | Bagli et al. |
| 4,119,710 A | 10/1978 | Engelhardt et al. |
| 4,223,137 A | 9/1980 | Yoshizaki et al. |
| 4,244,967 A | 1/1981 | Engelhardt et al. |
| 4,248,884 A | 2/1981 | Legrand et al. |
| 4,743,604 A | 5/1988 | Alig et al. |
| 4,927,836 A | 5/1990 | Holloway et al. |
| 5,019,578 A | 5/1991 | Fisher et al. |
| 5,061,727 A | 10/1991 | Bloom et al. |
| 5,705,515 A | 1/1998 | Fisher et al. |
| 6,346,532 B1 | 2/2002 | Maruyama et al. |
| 6,403,612 B2 | 6/2002 | Nantermet et al. |
| 7,795,310 B2 | 9/2010 | Lee et al. |
| 9,657,348 B2 | 5/2017 | Bengtsson |
| 9,784,726 B2 | 10/2017 | Bengtsson |
| 9,891,212 B2 | 2/2018 | Bengtsson |
| 10,288,602 B2 | 5/2019 | Bengtsson |
| 2001/0044454 A1 | 11/2001 | Nantermet et al. |
| 2003/0018061 A1 | 1/2003 | Ogawa et al. |
| 2004/0105819 A1 | 6/2004 | Hale et al. |
| 2004/0266867 A1 | 12/2004 | Cheng et al. |
| 2005/0250944 A1 | 11/2005 | Chen |
| 2006/0223886 A1 | 10/2006 | Dargazanli et al. |
| 2008/0306160 A1 | 12/2008 | Kobayashi et al. |
| 2009/0181976 A1 | 7/2009 | Buschmann et al. |
| 2010/0022658 A1 | 1/2010 | Epstein et al. |
| 2010/0022659 A1 | 1/2010 | Meyerson et al. |
| 2010/0173928 A1 | 7/2010 | Sabatini et al. |

(Continued)

FOREIGN PATENT DOCUMENTS

| | | |
|---|---|---|
| AT | 285583 B | 11/1970 |
| BE | 823841 A | 4/1975 |

(Continued)

OTHER PUBLICATIONS

Allen et al., Studies on the inhibition of glucose metabolism in isolated fat cells by beta-adrenergic blocking agents. Biochem Pharmacol. Jun. 1969;18(6):1347-54.

(Continued)

*Primary Examiner* — Zinna Northington Davis
(74) *Attorney, Agent, or Firm* — McCarter & English, LLP; Steven G. Davis; Mei Bai

(57) ABSTRACT

There is herein provided a compound of formula (I) or a pharmaceutically acceptable salt thereof, wherein the ring containing $Q^1$ to $Q^5$, and the groups $R^1$, $R^2$ and $R^3$, have meanings as provided in the description.

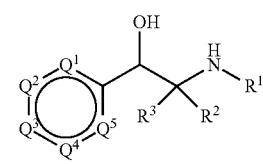

(I)

8 Claims, No Drawings

(56) References Cited

U.S. PATENT DOCUMENTS

| | | |
|---|---|---|
| 2011/0306552 A1 | 12/2011 | Rao et al. |
| 2013/0331433 A1 | 12/2013 | Thibonnier |
| 2017/0153225 A1 | 6/2017 | Bengtsson |
| 2019/0119196 A1 | 4/2019 | Pelcman et al. |
| 2019/0314301 A1 | 10/2019 | Pelcman et al. |
| 2020/0268687 A1 | 8/2020 | Pelcman et al. |
| 2020/0268688 A1 | 8/2020 | Pelcman et al. |
| 2020/0277259 A1 | 9/2020 | Pelcman et al. |
| 2020/0315993 A1 | 10/2020 | Pelcman et al. |
| 2021/0338603 A1 | 11/2021 | Pelcman et al. |

FOREIGN PATENT DOCUMENTS

| | | |
|---|---|---|
| CN | 103565784 A | 2/2014 |
| CN | 105078946 A | 11/2015 |
| CN | 106083837 A | 11/2016 |
| DE | 638650 C | 11/1936 |
| DE | 45721 A | 11/1966 |
| DE | 2015573 A1 | 10/1970 |
| DE | 2128258 A1 | 12/1971 |
| DE | 2157040 A1 | 5/1973 |
| DE | 2212600 A1 | 9/1973 |
| DE | 2259282 A1 | 6/1974 |
| DE | 2300614 A1 | 7/1974 |
| DE | 2413102 A1 | 10/1975 |
| DE | 2548053 A1 | 5/1976 |
| DE | 2700193 A1 | 7/1977 |
| DE | 2819458 A1 | 11/1978 |
| DE | 4209989 A1 | 10/1992 |
| EP | 0023385 A1 | 2/1981 |
| EP | 0043807 A2 | 1/1982 |
| EP | 0128120 A2 | 12/1984 |
| EP | 0195396 A1 | 9/1986 |
| EP | 0272976 A2 | 6/1988 |
| EP | 0290122 A1 | 11/1988 |
| EP | 0303546 A2 | 2/1989 |
| EP | 0357956 A2 | 3/1990 |
| EP | 0436435 A1 | 7/1991 |
| EP | 0543662 A2 | 5/1993 |
| EP | 0611003 A1 | 8/1994 |
| EP | 0659737 A2 | 6/1995 |
| EP | 1095932 A1 | 5/2001 |
| EP | 1277736 A1 | 1/2003 |
| EP | 1829534 A1 | 9/2007 |
| EP | 2426202 A1 | 3/2012 |
| FR | 1324914 A | 4/1963 |
| FR | 2647310 A1 | 11/1990 |
| GB | 1199630 A | 7/1970 |
| GB | 2054581 A | 2/1981 |
| GB | 2133986 A | 8/1984 |
| GB | 2151612 A | 7/1985 |
| JP | 52-105138 A | 9/1977 |
| JP | S56055355 A | 5/1981 |
| JP | H08-239349 A | 9/1996 |
| JP | 2005-097149 A | 4/2005 |
| JP | 2007-217368 A | 8/2007 |
| JP | 2008-505176 A | 2/2008 |
| NL | 7804582 A | 11/1978 |
| RU | 2095344 C1 | 11/1997 |
| WO | WO-1991/09596 | 7/1991 |
| WO | WO-1993/15041 | 8/1993 |
| WO | WO-1996/04234 | 2/1996 |
| WO | WO-1997/25311 | 7/1997 |
| WO | WO-1998/22480 | 5/1998 |
| WO | WO-1998/32753 | 7/1998 |
| WO | WO-1999/20607 | 4/1999 |
| WO | WO-1999/35279 | 7/1999 |
| WO | WO-1999/43326 | 9/1999 |
| WO | 1999/65311 A1 | 12/1999 |
| WO | WO-1999/65308 | 12/1999 |
| WO | WO-1999/65877 | 12/1999 |
| WO | WO-2000/075114 | 12/2000 |
| WO | WO-2001/74782 | 10/2001 |
| WO | WO-2002/032897 | 4/2002 |
| WO | WO-2003/032969 | 4/2003 |
| WO | 2003/101958 A2 | 12/2003 |
| WO | WO-2004/004451 | 1/2004 |
| WO | 2004/022566 A1 | 3/2004 |
| WO | WO-2004/071388 | 8/2004 |
| WO | WO-2004/110375 | 12/2004 |
| WO | WO-2005/013666 | 2/2005 |
| WO | WO-2005/025570 | 3/2005 |
| WO | 2005/037781 A2 | 4/2005 |
| WO | 2005/075458 A1 | 8/2005 |
| WO | 2005/108381 A1 | 11/2005 |
| WO | 2005/111002 A2 | 11/2005 |
| WO | WO-2005/102350 | 11/2005 |
| WO | WO-2005/110990 | 11/2005 |
| WO | WO-2005/114195 | 12/2005 |
| WO | 2006/04803 A1 | 1/2006 |
| WO | WO-2006/027579 | 3/2006 |
| WO | WO-2006/122788 | 11/2006 |
| WO | 2007/011065 A2 | 1/2007 |
| WO | 2007/026630 A1 | 3/2007 |
| WO | WO-2007/102011 | 9/2007 |
| WO | WO-2007/109882 | 10/2007 |
| WO | WO-2008/011453 | 1/2008 |
| WO | WO-2008/022038 | 2/2008 |
| WO | WO-2008/071948 | 6/2008 |
| WO | WO-2009/124166 | 10/2009 |
| WO | WO-2009/124167 | 10/2009 |
| WO | WO-2009/156413 | 12/2009 |
| WO | 2010/16939 A1 | 2/2010 |
| WO | 2011/037815 A1 | 3/2011 |
| WO | WO-2011/025960 | 3/2011 |
| WO | WO-2011/112867 | 9/2011 |
| WO | WO-2012064269 A1 * | 5/2012 ............ A61P 25/18 |
| WO | 2014/108449 A1 | 7/2014 |
| WO | WO-2018/011588 | 1/2018 |
| WO | 2019/053425 A1 | 3/2019 |
| ZA | 8703195 A * | 12/1987 |

OTHER PUBLICATIONS

Bercher et al., Wirkung fluorierter Phenyäthanolamine auf eine durch Katecholamine induzierte Hyperglykämie bei Ratten [The effect of fluoridated phenylethanolamines on hyperglycemia induced by catecholamines in the rat], Acta Biol Med Ger. 1975;34(4):667-74.

Cooperberg et al., Terbutaline and the prevention of nocturnal hypoglycemia in type 1 diabetes. Diabetes Care. Dec. 2008;31(12):2271-2.

Satoh, Glycemic effects of solanine in rats. Jpn J Pharmacol. Dec. 1967;17(4):652-8.

Star et al., Glucocorticoid-associated maternal hyperglycemia: a randomized trial of insulin prophylaxis. J Matern Fetal Med. Sep.-Oct. 2000;9(5):273-7.

Ahren et al., Adrenergic innervation of pancreatic islets and modulation of insulin secretion by the sympatho-adrenal system. Cell Tissue Res. 1981;216(1):15-30.

Alessi et al., Characterization of a 3-phosphoinositide-dependent protein kinase which phosphorylates and activates protein kinase Balpha. Curr Biol. Apr. 1, 1997;7(4):261-9.

Arch et al., Prospects for beta3-adrenoceptor agonists in the treatment of obesity and diabetes. International Journal of Obesity. 1996;20:191-199.

Baker et al., Chronic treatment with the beta(2)-adrenoceptor agonist prodrug BRL-47672 impairs rat skeletal muscle function by inducing a comprehensive shift to a faster muscle phenotype. J Pharmacol Exp Ther. Oct. 2006;319(1):439-46.

Barnes et al., Activation of GLUT1 by metabolic and osmotic stress: potential involvement of AMP-activated protein kinase (AMPK). J Cell Sci. Jun. 1, 2002;115(Pt 11):2433-42.

Baur et al., The identification of indacaterol as an ultralong-acting inhaled beta2-adrenoceptor agonist. J Med Chem. May 13, 2010;53(9):3675-84.

Beak et al., alpha.-Lithioamine synthetic equivalents: syntheses of diastereoisomers from the Boc-piperidines. J Org Chem. Apr. 1, 1990;55(9):2578-2580.

(56) References Cited

OTHER PUBLICATIONS

Bentzinger et al., Skeletal muscle-specific ablation of raptor, but not of rictor, causes metabolic changes and results in muscle dystrophy. Cell Metab. Nov. 2008;8(5):411-24.
Biel et al., Bronchodilators, N-substituted derivatives of 1-(3',4'-Dihydroxyphenyl)-2-aminoethanol (Arterenol). J Am Chem Soc. Jun. 1954;76:3149-53.
Brittain et al., Sympathomimetic bronchodilator drugs. Pharmacol Ther B. 1976;2(3):423-462.
Brown et al., A mammalian protein targeted by G1-arresting rapamycin-receptor complex. Nature. Jun. 30, 1994;369(6483):756-8.
Bryant et al., Regulated transport of the glucose transporter GLUT4. Nat Rev Mol Cell Biol. Apr. 2002;(4):267-77.
Cannon et al., Brown adipose tissue: function and physiological significance. Physiol Rev. Jan. 2004;84(1):277-359.
Carayannopoulos et al., GLUT8 is a glucose transporter responsible for insulin-stimulated glucose uptake in the blastocyst. Proc Natl Acad Sci U S A. Jun. 20, 2000;97(13):7313-8.
Castle et al., Attenuation of insulin resistance by chronic beta2-adrenergic agonist treatment possible muscle specific contributions. Life Sci. Jun. 22, 2001;69(5):599-611.
Chandler et al., Expression and localization of GLUT1 and GLUT12 in prostate carcinoma. Cancer. Apr. 15, 2003;97(8):2035-42.
Chariot et al., Effects of CRL 40827 and salbutamol on exocrine pancreatic secretion in rats. Eur J. Pharmacol. Jan. 27, 1988;146(1):17-25.
Chernogubova et al., Alpha1- and beta1-adrenoceptor signaling fully compensates for beta3-adrenoceptor deficiency in brown adipocyte norepinephrine-stimulated glucose uptake. Endocrinology. May 2005;146(5):2271-84.
Chernogubova et al., Norepinephrine increases glucose transport in brown adipocytes via beta3-adrenoceptors through a cAMP, PKA, and PI3-kinase-dependent pathway stimulating conventional and novel PKCs. Endocrinology. Jan. 2004;145(1):269-80.
Cioc et al., One-Pot Synthesis of N-Substituted beta-Amino Alcohols from Aldehydes and Isocyanides. Chemistry. 2015;21(21):7808-7813. Including supporting information.
Conde et al., beta-Adrenoceptor blocking activity of halogenated thienylethanolamine derivatives. J Med Chem. Jul. 1977;20(7):970-4.
Copp et al., TORC-specific phosphorylation of mammalian target of rapamycin (mTOR): phospho-Ser2481 is a marker for intact mTOR signaling complex 2. Cancer Res. Mar. 1, 2009;69(5):1821-7.
Cypress et al., Activation of Human Brown Adipose Tissue by a beta3-Adrenergic Receptor Agonist. Cell Metab. Jan. 21, 2015(1):33-38.
Dallner et al., Beta3-adrenergic receptors stimulate glucose uptake in brown adipocytes by two mechanisms independently of glucose transporter 4 translocation. Endocrinology. Dec. 2006;147(12):5730-9.
De Souza et al., Beta 3-adrenoceptor agonists as anti-diabetic and anti-obesity drugs in humans. Curr Pharm Des. Sep. 2001;7(14):1433-49.
Defronzo et al., Synergistic Interaction between Exercise and Insulin on Peripheral Glucose Uptake. J Clin Invest. Dec. 1981;68:1468-74.
Dehvari et al., beta(2)-Adrenoceptors increase translocation of GLUT4 via GPCR kinase sites in the receptor C-terminal tail. Br J Pharmacol. Mar. 2012;165(5):1442-56.
Drake et al., Trafficking of G protein-coupled receptors. Circ Res. Sep. 15, 2006;99(6):570-82.
Edmondson et al., Discovery of Vibegron: A Potent and Selective β3 Adrenergic Receptor Agonist for the Treatment of Overactive Bladder. J Med Chem. Jan. 28, 2016;59(2):609-23.
Elayan et al., Chronic beta2 adrenergic agonist, but not exercise, improves glucose handling in older type 2 diabetic mice. Cell Mol Neurobiol. Jul. 2012;32(5):871-7.
Engelhardt, Structure activity relationship in a series of new amino-halogen substituted phenyl-aminoethanols. Arzneimittelforschung. May 1972;22(5):869-76.

Evans et al., beta2-Adrenoceptor-mediated regulation of glucose uptake in skeletal muscle—ligand-directed signalling or a reflection of system complexity? Naunyn Schmiedebergs Arch Pharmacol. Sep. 2013;386(9):757-60.
Evron et al., GRK2: multiple roles beyond G protein-coupled receptor desensitization. Trends Pharmacol Sci. Mar. 2012;33(3):154-64.
Exton, Mechanisms of hormonal regulation of hepatic glucose metabolism. Diabetes Metab Rev. Jan. 1987;3(1):163-83.
Feldman et al., Active-Site Inhibitors of mTOR Target Rapamycin-Resistant Outputs of mTORC1 and mTORC2. PLoS Biol. Feb. 10, 2009;7(2):e38. 13 pages.
Fisher et al., BMS-187257, a Potent, Selective, and Novel Heterocyclic beta3 Adrenergic Receptor Agonist. Bioorganic & Medicinal Chemistry Letters. 1996;6(19):2253-8.
Garcia-Martinez et al., Ku-0063794 is a specific inhibitor of the mammalian target of rapamycin (mTOR). Biochem J. Jun. 12, 2009;421(1):29-42.
Gaster et al., GLUT4 is reduced in slow muscle fibers of type 2 diabetic patients: is insulin resistance in type 2 diabetes a slow, type 1 fiber disease? Diabetes. Jun. 2001;50(6):1324-9.
Gavai et al., BMS-196085: a potent and selective full agonist of the human beta(3) adrenergic receptor. Bioorg Med Chem Lett. Dec. 3, 2001;11(23):3041-4.
Gawlik et al., Targeted disruption of Slc2a8 (GLUT8) reduces motility and mitochondrial potential of spermatozoa. Mol Membr Biol. Apr. 2008;25(3):224-35.
Gilman, G proteins: transducers of receptor-generated signals. Annu Rev Biochem. 1987;56:615-49.
Green et al., Use of Akt inhibitor and a drug-resistant mutant validates a critical role for protein kinase B/Akt in the insulin-dependent regulation of glucose and system A amino acid uptake. J Biol Chem. Oct. 10, 2008;283(41):27653-67.
Greife et al., Effects of the phenethanolamine clenbuterol on protein and lipid metabolism in growing rats. J Anim Physiol a Anim Nutr. 1989;61:19-27.
Gusovsky, Measurement of second messengers in signal transduction: cAMP and inositol phosphates. Curr Protoc Neurosci. May 2001;Chapter 7:Unit7.12.
Harrison et al., Activation of cell surface glucose transporters measured by photoaffinity labeling of insulin-sensitive 3T3-L1 adipocytes. J Biol Chem. Feb. 25, 1992;267(6):3783-8.
Harrison et al., Suppressed intrinsic catalytic activity of GLUT1 glucose transporters in insulin-sensitive 3T3-L1 adipocytes. Proc Natl Acad Sci U S A. Sep. 1, 1991;88(17):7839-43.
Hawkins et al., Signalling through Class I PI3Ks in mammalian cells. Biochem Soc Trans. Nov. 2006;34(Pt 5):647-62.
Hebert et al., Direct evidence for ATP modulation of sugar transport in human erythrocyte ghosts. J Biol Chem. Aug. 5, 1986;261(22):10093-9.
Hresko et al., mTOR.RICTOR is the Ser473 kinase for Akt/protein kinase B in 3T3-L1 adipocytes. J Biol Chem. Dec. 9, 2005;280(49):40406-16.
Huang et al., The GLUT4 glucose transporter. Cell Metab. Apr. 2007;5(4):237-52.
Huang, An in vitro assay for the kinase activity of mTOR complex 2. Methods Mol Biol. 2012;821:75-86.
Hutchinson et al., Agonist effects of zinterol at the mouse and human beta(3)-adrenoceptor. Naunyn Schmiedebergs Arch Pharmacol. May 2006;373(2):158-68.
Hutchinson et al., alpha1A-adrenoceptors activate glucose uptake in L6 muscle cells through a phospholipase C-, phosphatidylinositol-3 kinase-, and atypical protein kinase C-dependent pathway. Endocrinology. Feb. 2005;146(2):901-12.
Hutchinson et al., AMP-activated protein kinase activation by adrenoceptors in L6 skeletal muscle cells: mediation by alpha1-adrenoceptors causing glucose uptake. Diabetes. Mar. 2006;55(3):682-90.
Inokuma et al., Uncoupling protein 1 is necessary for norepinephrine-induced glucose utilization in brown adipose tissue. Diabetes. May 2005;54(5):1385-91.

(56) References Cited

OTHER PUBLICATIONS

Jones et al., G protein-coupled receptor kinases 2 and 5 are differentially expressed in rat skeletal muscle and remain unchanged following beta2-agonist administration. Exp Physiol. Mar. 2003;88(2):277-84.
Jozwiak et al., Comparative molecular field analysis of the binding of the stereoisomers of fenoterol and fenoterol derivatives to the beta2 adrenergic receptor. J Med Chem. Jun. 2007;50(12):2903-15.
Kaiser et al., Adrenergic agents. 1. Synthesis and potential beta-adrenergic agonist activity of some catecholamine analogs bearing a substituted amino functionality in the meta position. J Med Chem. Jan. 1974;17(1):49-57.
Kleiman et al., Developmentally spliced PKCbetaII provides a possible link between mTORC2 and Akt kinase to regulate 3T3-L1 adipocyte insulin-stimulated glucose transport. Biochem Biophys Res Commun. Oct. 23, 2009;388(3):554-9.
Koshy et al., Quantitative Measurement of GLUT4 Translocation to the Plasma Membrane by Flow Cytometry. Jove, J Vis Exp. www.jove.com. 3 pages, (2010).
Kovala et al., Protein kinase A regulation of cAMP phosphodiesterase expression in rat skeletal myoblasts. J Biol Chem. Mar. 25, 1994;269(12):8680-5.
Kumar et al., Fat cell-specific ablation of rictor in mice impairs insulin-regulated fat cell and whole-body glucose and lipid metabolism. Diabetes. Jun. 2010;59(6):1397-406.
Lacey et al., Selective stimulation of glucagon secretion by beta 2-adrenoceptors in isolated islets of Langerhans of the rat. Br J Pharmacol. Jul. 1991;103(3):1824-8.
Lamming et al., A Central role for mTOR in lipid homeostasis. Cell Metab. Oct. 1, 2013;18(4):465-9.
Laplante et al., mTOR signaling in growth control and disease. Cell. Apr. 13, 2012;149(2):274-93.
Largis et al., Antidiabetic and antiobesity effects of a highly selective β3-adrenoceptor agonist (CL 316,243). Drug Development Research. Jun. 1994;32(2):69-76.
Lawrence et al., GLUT4 facilitates insulin stimulation and cAMP-mediated inhibition of glucose transport. Proc Natl Acad Sci U S A. Apr. 15, 1992;89(8):3493-7.
Lidell et al., Evidence for two types of brown adipose tissue in humans. Nat Med. May 2013;19(5):631-4.
Liggett et al., Characterization of beta-adrenergic receptors of human skeletal muscle obtained by needle biopsy. Am J Physiol. 1988;254:E795-8.
Liu et al., Biphasic effects of the beta-adrenoceptor agonist, BRL 37344, on glucose utilization in rat isolated skeletal muscle. Br J Pharmacol. Mar. 1996;117(6):1355-61.
Liu et al., Chronic norepinephrine infusion stimulates glucose uptake in white and brown adipose tissues. Am J Physiol. 1994;266:914-20.
Macaulay et al., Isoproterenol inhibits cyclic AMP-mediated but not insulin-mediated translocation of the GLUT4 glucose transporter isoform. Mol Cell Biochem. Dec. 7, 1994;141(1):27-33.
Macheda et al., Molecular and cellular regulation of glucose transporter (GLUT) proteins in cancer. J Cell Physiol. Mar. 2005;202(3):654-62.
Marette et al., Stimulation of glucose transport by insulin and norepinephrine in isolated rat brown adipocytes. Am J Physiol. Oct. 1989;257(4 Pt 1):C714-21.
Mathvink et al., Potent, selective 3-pyridylethanolamine beta3 adrenergic receptor agonists possessing a thiazole benzenesulfonamide pharmacophore. Bioorg Med Chem Lett. Sep. 4, 2000;10(17):1971-3.
Mills et al., Beta-blockers and glucose control. Drug Intell Clin Pharm. Apr. 1985;19(4):246-51.
Murata et al., Indinavir inhibits the glucose transporter isoform Glut4 at physiologic concentrations. AIDS. Apr. 12, 2002;16(6):859-63.
Nave et al., Mammalian target of rapamycin is a direct target for protein kinase B: identification of a convergence point for opposing effects of insulin and amino-acid deficiency on protein translation. Biochem J. Dec. 1, 1999;344 Pt 2:427-31.
Nedergaard et al., New powers of brown fat: fighting the metabolic syndrome. Cell Metab. Mar. 2, 2011;13(3):238-40.
Nedergaard et al., PPARgamma in the control of brown adipocyte differentiation. Biochim Biophys Acta. May 30, 2005;1740(2):293-304.
Nedergaard et al., Three years with adult human brown adipose tissue. Ann N.Y. Acad Sci. 2011;1212:E20-E36.
Nedergaard et al., Unexpected evidence for active brown adipose tissue in adult humans. Am J Physiol Endocrinol Metab. 2007;293:E444-E452.
Neve et al., Turnover of beta 1- and beta 2-adrenergic receptors after down-regulation or irreversible blockade. Mol Pharmacol. Aug. 1986;30(2):104-11.
Nevzorova et al., Characterization of the beta-adrenoceptor subtype involved in mediation of glucose transport in L6 cells. Br J Pharmacol. Sep. 2002;137(1):9-18.
Nevzorova et al., Multiple signalling pathways involved in beta2-adrenoceptor-mediated glucose uptake in rat skeletal muscle cells. Br J Pharmacol. Feb. 2006;147(4):446-54.
Ngala et al., beta2-adrenoceptor agonists can both stimulate and inhibit glucose uptake in mouse soleus muscle through ligand-directed signalling. Naunyn Schmiedebergs Arch Pharmacol. Sep. 2013;386(9):761-73.
Ngala et al., Beta2-adrenoceptors and non-beta-adrenoceptors mediate effects of BRL37344 and clenbuterol on glucose uptake in soleus muscle: studies using knockout mice. Br J Pharmacol. Dec. 2009;158(7):1676-82.
Ngala et al., Metabolic responses to BRL37344 and clenbuterol in soleus muscle and C2C12 cells via different atypical pharmacologies and beta2-adrenoceptor mechanisms. Br J Pharmacol. Oct. 2008;155(3):395-406.
Ning et al., A new, one-step synthesis of 1-heteroaryl-2-alkylaminoethanols. Tetrahedron Letters. 2010;51:843-845.
Nobles et al., Distinct phosphorylation sites on the beta(2)-adrenergic receptor establish a barcode that encodes differential functions of beta-arrestin. Sci Signal. Aug. 9, 2011;4(185):ra51.
Nugent et al., Potentiation of glucose uptake in 3T3-L1 adipocytes by PPAR gamma agonists is maintained in cells expressing a PPAR gamma dominant-negative mutant: evidence for selectivity in the downstream responses to PPAR gamma activation. Mol Endocrinol. Oct. 2001;15(10):1729-38.
Palmada et al., SGK1 kinase upregulates GLUT1 activity and plasma membrane expression. Diabetes. Feb. 2006;55(2):421-7.
Pan et al., Effects of clenbuterol on insulin resistance in conscious obese Zucker rats. Am J Physiol Endocrinol Metab. Apr. 2001;280(4):E554-61.
Parmee et al., Discovery of L-755,507: a subnanomolar human beta 3 adrenergic receptor agonist. Bioorg Med Chem Lett. May 5, 1998;8(9):1107-12.
Phung et al., Pathological angiogenesis is induced by sustained Akt signaling and inhibited by rapamycin. Cancer Cell. Aug. 2006;10(2):159-70.
Plazinska et al., Molecular interactions between fenoterol stereoisomers and derivatives and the beta2-adrenergic receptor binding site studied by docking and molecular dynamics simulations. J Mol Model. Nov. 2013;19(11):4919-30.
Ploug et al., Kinetics of glucose transport in rat muscle: effects of insulin and contractions. Am J Physiol. 1987;253:12-20.
Polak et al., Adipose-specific knockout of raptor results in lean mice with enhanced mitochondrial respiration. Cell Metab. Nov. 2008;8(5):399-410.
PubChem CID: CID=4225365, 2-(Cyclohexylmethylamino)-1-phenylethanol, 2-[(cyclohexylmethyl)amino]-1-phenylethanol; 2-(cyclohexylmethylamino)-1-phen HMS1755E04, 1 page, Dec. 1, 2018.
PubChem CID: CID=83307546, SCHEMBL19329935; AKOS023017379. 4-[2-(Cyclohexylmethylamino)-1-hydroxyethyl]phenol. Dec. 12, 2001.

(56) References Cited

OTHER PUBLICATIONS

PubChem, Compound CID: 60051619, SCHEMBL19329904, 1 page, Aug. 20, 2012.
PubChem, Compound CID: 89173082, SCHEMBL13799302, 1 page, Feb. 13, 2015.
Rao et al., Synthesis, antimicrobial and molecular docking studies of enantiomerically pure N-alkylated beta-amino alcohols from phenylpropanolamines. Bioorg Med Chem Lett. Jul. 2014;24(14):3057-63.
Reinicke et al., Cellular distribution of Glut-1 and Glut-5 in benign and malignant human prostate tissue. J Cell Biochem. Feb. 2012;113(2):553-62.
Rodnick et al., Interaction of insulin and exercise on glucose transport in muscle. Diabetes Care. Nov. 1992;15(11):1679-89.
Rovira et al., mTOR Inhibition: Reduced Insulin Secretion and Sensitivity in a Rat Model of Metabolic Syndrome. Transplant Direct. Jan. 22, 2016;2(2):e65, 9 pages.
Rowland et al., Mapping insulin/GLUT4 circuitry. Traffic. Jun. 2011;12(6):672-81.
Rydzewski, Real World Drug Discovery, a Chemist's Guide to Biotech and Pharmaceutical Research. Elsevier, Amsterdam. pp. 42-43, (2008).
Salvador et al., Inhibition by butoxamine, propranolol and MJ1999 of the glycogenolytic action of the catecholamines in the rat. Biochem Pharmacol. Oct. 1967;16(10):2037-41.
Santulli et al., Pinpointing beta adrenergic receptor in ageing pathophysiology: victim or executioner? Evidence from crime scenes. Immun Ageing. Mar. 15, 2013;10(1):10.
Sarabia et al., Glucose uptake in human and animal muscle cells in culture. Biochem Cell Biol. Feb. 1990;68(2):536-42.
Sarbassov et al., Prolonged rapamycin treatment inhibits mTORC2 assembly and Akt/PKB. Mol Cell. Apr. 21, 2006;22(2):159-68.
Sarbassov et al., Rictor, a novel binding partner of mTOR, defines a rapamycin-insensitive and raptor-independent pathway that regulates the cytoskeleton. Curr Biol. Jul. 27, 2004;14(14):1296-302.
Sekulic et al., A direct linkage between the phosphoinositide 3-kinase-AKT signaling pathway and the mammalian target of rapamycin in mitogen-stimulated and transformed cells. Cancer Res. Jul. 1, 2000;60(13):3504-13.
Sennitt et al., The contribution of classical (beta1/2-) and atypical beta-adrenoceptors to the stimulation of human white adipocyte lipolysis and right atrial appendage contraction by novel beta3-adrenoceptor agonists of differing selectivities. J Pharmacol Exp Ther. Jun. 1998;285(3):1084-95.
Shah et al., The role of glucose transporters in brain disease: diabetes and Alzheimer's Disease. Int J Mol Sci. Oct. 3, 2012;13(10):12629-55.
Shan et al., Effects of GLUT4 expression on insulin resistance in patients with advanced liver cirrhosis. J Zhejiang Univ Sci B. Aug. 2011;12(8):677-82.
Shenoy et al., G-Protein Coupled Receptor—A Potential New Drug Target to Combat Diabetic Syndrome: An Overview. IJPSR. 2011;2(10):2490-2500.
Shibata et al., Cold exposure reverses inhibitory effects of fasting on peripheral glucose uptake in rats. Am J Physiol. Jul. 1989;257(1 Pt 2):R96-101.
Shimizu et al., Activation of brown adipose tissue thermogenesis in recovery from anesthetic hypothermia in rats. Am J Physiol. Aug. 1991;261(2 Pt 2):R301-4.
Simpson et al., The facilitative glucose transporter GLUT3: 20 years of distinction. Am J Physiol Endocrinol Metab. 2008;295:E242-E253.
Sobel et al., Abolition of crypticity of Arthrobacter pyridinolis toward glucose and alpha-glucosides by tricarboxylic acid cycle intermediates. J Bacteriol. Oct. 1973;116(1):271-8.
Spiller et al., A descriptive study of adverse events from clenbuterol misuse and abuse for weight loss and bodybuilding. Subst Abus. 2013;34(3):306-12.
Sprenger et al., Biophysical techniques for detection of cAMP and cGMP in living cells. Int J Mol Sci. Apr. 12, 2013;14(4):8025-46.

Stanford et al., Brown adipose tissue regulates glucose homeostasis and insulin sensitivity. J Clin Invest. Jan. 2013;123(1):215-23.
Taha et al., The insulin-dependent biosynthesis of GLUT1 and GLUT3 glucose transporters in L6 muscle cells is mediated by distinct pathways. Roles of p21ras and pp70 S6 kinase. J Biol Chem. Oct. 20, 1995;270(42):24678-81.
Tanis et al., Solvent and in situ catalyst preparation impacts upon Noyori reductions of aryl-chloromethyl ketones: application to syntheses of chiral 2-amino-1-aryl-ethanols. Tetrahedron: Asymmetry. Aug. 28, 2006;17(14):2154-82.
Tanis et al., The design and development of 2-aryl-2-hydroxy ethylamine substituted 1H,7H-pyrido[1,2,3-de]quinoxaline-6-carboxamides as inhibitors of human cytomegalovirus polymerase. Bioorg Med Chem Lett. Mar. 15, 2010;20(6):1994-2000.
Taverna et al., Reversible association of cytochalasin B with the human erythrocyte membrane. Inhibition of glucose transport and the stoichiometry of cytochalasin binding. Biochim Biophys Acta. Oct. 11, 1973;323(2):207-19.
Thong et al., Turning signals on and off: GLUT4 traffic in the insulin-signaling highway. Physiology (Bethesda). Aug. 2005;20:271-84.
Torgan et al., Exercise training and clenbuterol reduce insulin resistance of obese Zucker rats. Am J Physiol. Mar. 1993;264(3 Pt 1):E373-9.
Tritos et al., Clinical review 97: Syndromes of severe insulin resistance. J Clin Endocrinol Metab. Sep. 1998;83(9):3025-30.
Unger, Die Wirkung von butedrin auf den Blutzucker. The Effect of Butedrine on Blood Sugar. Zschr Inn Med. Jour Inn Med. Apr. 8, 1961;16(17):742-745.
Vardanega-Peicher et al., Time sequence of changes in the responsiveness of glycogen breakdown to adrenergic agonists in perfused liver of rats with insulin-induced hypoglycemia. Braz J Med Biol Res. Jul. 2000;33(7):805-13.
Violin et al., G-protein-coupled receptor kinase specificity for beta-arrestin recruitment to the beta2-adrenergic receptor revealed by fluorescence resonance energy transfer. J Biol Chem. Jul. 21, 2006;281(29):20577-88.
Watson-Wright et al., The Muscle Slice—A New Preparation for the Characterization of beta-Adrenergic Binding in Fast- and Slow-twitch Skeletal Muscle. Muscle & Nerve. 1986;9:416-22.
Woo et al., Stereochemistry of an agonist determines coupling preference of beta2-adrenoceptor to different G proteins in cardiomyocytes. Mol Pharmacol. Jan. 2009;75(1):158-65.
Yamamoto et al., Beta(2)-Adrenergic activation increases glycogen synthesis in L6 skeletal muscle cells through a signalling pathway independent of cyclic AMP. Diabetologia. Jan. 2007;50(1):158-67.
Zeng et al., Rapamycin derivatives reduce mTORC2 signaling and inhibit AKT activation in AML. Blood. Apr. 15, 2007;109(8):3509-12.
Zhu et al., Discovery of benzamides as potent human 3 adrenergic receptor agonists. Bioorg Med Chem Lett. Jan. 1, 2016;26(1):55-9.
Ziegler et al., Endogenous epinephrine protects against obesity induced insulin resistance. Auton Neurosci. Jul. 5, 2011;162(1-2):32-4.
Ziegler et al., Epinephrine and the metabolic syndrome. Curr Hypertens Rep. Feb. 2012;14(1):1-7.
Zierath, In vitro studies of human skeletal muscle: hormonal and metabolic regulation of glucose transport. Acta Physiol Scand Suppl. 1995;626:1-96.
Zinzalla et al., Activation of mTORC2 by association with the ribosome. Cell. Mar. 4, 2011;144(5):757-68.
International Search Report and Written Opinion for Application No. PCT/GB2018/052595, dated Nov. 6, 2018, 12 pages.
Besev et al., Diastereocontrol by a hydroxyl auxiliary in the synthesis of pyrrolidines via radical cyclization. Org Lett. Sep. 5, 2002;4(18):3023-5.
Chen et al., Syntheses of 2,5- and 2,6-difluoronorepinephrine, 2,5-difluoroepinephrine, and 2,6-difluorophenylephrine: effect of disubstitution with fluorine on adrenergic activity. J Med Chem. Nov. 26, 1993;36(24):3947-55.

(56) References Cited

OTHER PUBLICATIONS

Lands, The Effect on Blood Pressure and Toxicity of 1-{3-Fluorophenyl)-2-Aminoethanol and Related Compounds. Journal of Pharmacology and Experimental Therapeutics. Dec. 1, 1952;106(4):440-443.

Lu et al., Syntheses of (R)- and (S)-2- and 6-fluoronorepinephrine and (R)- and (S)-2- and 6-fluoroepinephrine: effect of stereochemistry on fluorine-induced adrenergic selectivities. J Med Chem. Apr. 20, 2000;43(8):1611-9.

Luthy et al., Lead-oriented synthesis: Investigation of organolithium-mediated routes to 3-D scaffolds and 3-D shape analysis of a virtual lead-like library. Bioorg Med Chem. Jun. 1, 2015;23(11):2680-94.

Mathvink et al., Discovery of a potent, orally bioavailable beta(3) adrenergic receptor agonist, (R)-N-[4-[2-[[2-hydroxy-2-(3-pyridinyl)ethyl]amino]ethyl]phenyl]-4-[4-[4-(trifluoromethyl)phenyl]thiazol-2-yl]benzenesulfonamide. J Med Chem. Oct. 19, 2000;43(21):3832-6.

McCarty et al., Central Stimulants. a,a-Disubstituted 2-Piperidinemethanols and 1,1-Disubstituted Heptahydroöxazolo [3,4-a]pyridines. J Am Chem Soc. 1957;79:472-480.

Sanner, Stereoselective condensations of a'-lithio pyrrolidine amidines. Tetrahedron Letters. 1989;30(15):1909-1912.

Ye et al., Dual catalysis for enantioselective convergent synthesis of enantiopure vicinal amino alcohols. Nat Commun. Jan. 29, 2018;9(1):410, 9 pages.

Ye et al., One-Pot Cascade Hydration-Asymmetric Transfer Hydrogenation as a Practical Strategy to Construct Chiral beta-Adrenergic Receptor Blockers. ChemCatChem. Jun. 15, 2015;7(12):1801-1805.

U.S. Appl. No. 14/759,572, filed Jul. 7, 2015, U.S. Pat. No. 9,784,726, Issued.

U.S. Appl. No. 15/727,851, filed Oct. 9, 2017, U.S. Pat. No. 10,288,602, Issued.

U.S. Appl. No. 14/759,747, filed Apr. 8, 2015, U.S. Pat. No. 9,657,348, Issued.

U.S. Appl. No. 15/104,830, filed Jun. 15, 2016, U.S. Pat. No. 9,891,212, Issued.

U.S. Appl. No. 15/324,580, filed Jan. 6, 2017, 2017-0153225, Abandoned.

U.S. Appl. No. 16/082,750, filed Sep. 6, 2018, 2019-0119196, Published.

U.S. Appl. No. 16/317,009, filed Jan. 10, 2019, 2019-0314301, Abandoned.

U.S. Appl. No. 16/908,312, filed Jun. 22, 2020, 2020-0315993, Abandoned.

U.S. Appl. No. 17/320,774, filed May 14, 2021, 2021-0338603, Published.

U.S. Appl. No. 16/646,050, filed Mar. 10, 2020, 2020-0277259, Published.

U.S. Appl. No. 16/646,497, filed Mar. 11, 2020, 2020-0268688, Published.

U.S. Appl. No. 16/646,492, filed Mar. 11, 2020, 2020-0268687, Published.

U.S. Appl. No. 17/439,638, filed Sep. 15, 2021, Pending.

U.S. Appl. No. 17/439,668, filed Sep. 15, 2021, Pending.

Ookawa et al., Asymmetric Synthesis of Optically Active threo- and erythro-Pyrrolidinylbenzyl Alcohol by the Highly Stereospecific Arylation of (S)-Proline and the Subsequent Highly Diastereoselective Reduction of the alpha-Amino Ketone. J Chem Soc Perkin Trans 1. 1987;1465-1471.

U.S. Appl. No. 16/802,750, filed Sep. 6, 2018, 2019-0119196, Published.

U.S. Appl. No. 17/575,175, filed Jan. 13, 2022, Pending.

CAS RN 2155248-91-0. Chemcats entry date: Jan. 15, 2019. 1 page.
CAS RN 2274711-69-0. Chemcats entry date: Jan. 15, 2019. 1 page.
CAS RN 2278127-42-5. Chemcats entry date: Jan. 15, 2019. 1 page.
CAS RN 2287791-82-4. Chemcats entry date: Jan. 15, 2019. 1 page.
CAS RN 2289315-62-2. Chemcats entry date: Jan. 15, 2019. 1 page.

Ashmore et al., Effects of Dichloroisoproterenol on Blood Sugar and Plasma Free Fatty Acids. Proceedings of the Society for Experimental Biology and Medicine. 1962;109:291-294.

Chait et al., Diabetes and atherosclerosis: is there a role for hyperglycemia? J Lipid Res. Apr. 2009;50 Suppl(Suppl) S335-9.

* cited by examiner

HETEROARYL SUBSTITUTED BETA-HYDROXYETHYLAMINES FOR USE IN TREATING HYPERGLYCAEMIA

CROSS-REFERENCE TO RELATED APPLICATIONS

This application is a U.S. national stage filing, under 35 U.S.C. § 371(c), of International Application No. PCT/GB2018/052595, filed on Sep. 13, 2018, which claims priority to United Kingdom Patent Application No. 1714745.5, filed on Sep. 13, 2017.

FIELD OF THE INVENTION

The present invention relates to novel compounds and compositions, and their use in the treatment of hyperglycaemia and disorders characterised by hyperglycaemia, such as type 2 diabetes. In particular, the invention relates to novel compounds, compositions and methods for the treatment of conditions such as type 2 diabetes through activation of the $\beta_2$-adrenergic receptor. Importantly, such compounds are thought to have a beneficial side-effect profile as they do not exert their effect through significant cAMP release.

BACKGROUND OF THE INVENTION

The listing or discussion of an apparently prior-published document in this specification should not necessarily be taken as an acknowledgement that the document is part of the state of the art or is common general knowledge.

Hyperglycaemia, or high blood sugar is a condition in which an excessive amount of glucose circulates in the blood plasma. If not treated, hyperglycaemia can be a serious problem, potentially developing into life-threatening conditions such as ketoacidosis. For example, chronic hyperglycemia may cause injury to the heart, and is strongly associated with heart attacks and death in subjects with no coronary heart disease or history of heart failure. There are various causes of hyperglycaemia, including diabetes and severe insulin resistance.

Severe insulin resistance (SIR) is a condition wherein the patient experiences very low levels of (or, in extreme cases, no significant) response to insulin. There are several syndromes characterized by SIR, including Rabson-Mendenhall syndrome, Donohue's syndrome (leprechaunism), Type A and Type B syndromes of insulin resistance, the HAIR-AN (hyperandrogenism, insulin resistance, and acanthosis nigricans) syndrome, pseudoacromegaly, and lipodystrophy. The majority of these conditions have genetic causes, such as mutations in the insulin receptor gene. The prevalence for Donohue's syndrome, Rabson-Mendenhall syndrome and Type A syndrome of insulin resistance, has been reported to vary from about 50 reported cases to 1 in 100,000. However, since some diseases are severe and extremely rare, it is likely that many patients do not get diagnosed before they die, particularly in less developed areas of the world. Thus, the exact number of patients with these syndromes is difficult to assess.

The current standard for hyperglycaemia treatment in patients having SIR is a controlled diet, supplemented with drugs affecting insulin receptor sensitivity, such as metformin, or insulin supplement. However, particularly for disorders caused by mutations in the insulin receptor gene, this treatment is not sufficiently effective and ultimately proves unsuccessful.

Diabetes comprises two distinct diseases, type 1 (or insulin-dependent diabetes) and type 2 (insulin-independent diabetes), both of which involve the malfunction of glucose homeostasis. Type 2 diabetes affects more than 400 million people in the world and the number is rising rapidly. Complications of type 2 diabetes include severe cardiovascular problems, kidney failure, peripheral neuropathy, blindness and, in the later stages of the disease, even loss of limbs and, ultimately death. Type 2 diabetes is characterized by insulin resistance in skeletal muscle and adipose tissue, and there is presently no definitive cure. Most treatments used today are focused on remedying dysfunctional insulin signalling or inhibiting glucose output from the liver but many of those treatments have several drawbacks and side effects. There is thus a great interest in identifying novel insulin-independent ways to treat type 2 diabetes.

In type 2 diabetes, the insulin-signalling pathway is blunted in peripheral tissues such as adipose tissue and skeletal muscle. Methods for treating type 2 diabetes typically include lifestyle changes, as well as insulin injections or oral medications to regulate glucose homeostasis. People with type 2 diabetes in the later stages of the disease develop 'beta-cell failure' i.e. the inability of the pancreas to release insulin in response to high blood glucose levels. In the later stages of the disease patients often require insulin injections in combination with oral medications to manage their diabetes. Further, most common drugs have side effects including downregulation or desensitization of the insulin pathway and/or the promotion of lipid incorporation in adipose tissue, liver and skeletal muscle. There is thus a great interest in identifying novel ways to treat metabolic diseases including type 2 diabetes that do not include these side effects.

Following a meal, increased blood glucose levels stimulate insulin release from the pancreas. Insulin mediates normalization of the blood glucose levels. Important effects of insulin on glucose metabolism include facilitation of glucose uptake into skeletal muscle and adipocytes, and an increase of glycogen storage in the liver. Skeletal muscle and adipocytes are responsible for insulin-mediated glucose uptake and utilization in the fed state, making them very important sites for glucose metabolism.

The signalling pathway downstream from the insulin receptor has been difficult to understand in detail. In brief, control of glucose uptake by insulin involves activation of the insulin receptor (IR), the insulin receptor substrate (IRS), the phosphoinositide 3-kinase (PI3K) and thus stimulation of phosphatidylinositol (3,4,5)-triphosphate (PIP3), the mammalian target of rapamycin (also called the mechanistic target of rapamycin, mTOR), Akt/PKB (Akt) and TBC1D4 (AS160), leading to translocation of the glucose transporter 4 (GLUT4) to the plasma membrane. Akt activation is considered necessary for GLUT4 translocation.

It should be noted that skeletal muscles constitute a major part of the body weight of mammals and have a vital role in the regulation of systemic glucose metabolism, being responsible for up to 85% of whole-body glucose disposal. Glucose uptake in skeletal muscles is regulated by several intra- and extracellular signals. Insulin is the most well studied mediator but others also exist. For example, AMP activated kinase (AMPK) functions as an energy sensor in the cell, which can increase glucose uptake and fatty acid oxidation. Due to the great influence skeletal muscles have on glucose homeostasis it is plausible that additional mechanisms exist. In the light of the increased prevalence of type 2 diabetes, it is of great interest to find and characterize novel insulin-independent mechanisms to increase glucose uptake in muscle cells.

Blood glucose levels may be regulated by both insulin and catecholamines, but they are released in the body in response to different stimuli. Whereas insulin is released in response to the rise in blood sugar levels (e.g. after a meal), epinephrine and norepinephrine are released in response to various internal and external stimuli, such as exercise, emotions and stress, and also for maintaining tissue homeostasis. Insulin is an anabolic hormone that stimulates many processes involved in growth including glucose uptake, glycogen and triglyceride formation, whereas catecholamines are mainly catabolic.

Although insulin and catecholamines normally have opposing effects, it has been shown that they have similar actions on glucose uptake in skeletal muscle (Nevzorova et al., *Br. J. Pharmacol*, 137, 9, (2002)). In particular, it has been reported that catecholamines stimulate glucose uptake via adrenergic receptors (Nevzorova et al., *Br. J. Pharmacol*, 147, 446, (2006); Hutchinson, Bengtsson *Endocrinology* 146, 901, (2005)) to supply muscle cells with an energy-rich substrate. Thus it is likely that in mammals, including humans, the adrenergic and the insulin systems can work independently to regulate the energy needs of skeletal muscle in different situations. Since insulin also stimulates many anabolic processes, including some that promote undesired effects such as stimulation of lipid incorporation into tissues, leading to e.g. obesity, it would be beneficial to be able to stimulate glucose uptake by other means; for example, by stimulation of the adrenergic receptors (ARs).

All ARs are G protein-coupled receptors (GPCRs) located in the cell membrane and characterized by an extracellular N-terminus, followed by seven transmembrane α-helices (TM-1 to TM-7) connected by three intracellular (IL-1 to IL-3) and three extracellular loops (EL-1 to EL-3), and finally an intracellular C-terminus. There are three different classes of ARs, with distinct expression patterns and pharmacological profiles: $\alpha_1$-, $\alpha_2$- and β-ARs. The $\alpha_1$-ARs comprise the $\alpha_{1A}$, $\alpha_{1B}$ and $\alpha_{1D}$ subtypes while $\alpha_2$-ARs are divided into $\alpha_{2A}$, $\alpha_{2B}$ and $\alpha_{2C}$. The β-ARs are also divided into the subtypes $β_1$, $β_2$, and $β_3$, of which $β_2$-AR is the major isoform in skeletal muscle cells. ARs are G protein coupled receptors (GPCRs) that signal through classical secondary messengers such as cyclic adenosine monophosphate (cAMP) and phospholipase C (PLC).

Many effects occurring downstream of ARs in skeletal muscles have been attributed to classical secondary messenger signalling, such as increase in cAMP levels, PLC activity and calcium levels. Stimulation involving the classical secondary messengers has many effects in different tissues. For example, it increases heart rate, blood flow, airflow in lungs and release of glucose from the liver, which all can be detrimental or be considered unwanted side effects if stimulation of ARs should be considered as a type 2 diabetes treatment. Adverse effects of classical AR agonists are, for example, tachycardia, palpitation, tremor, sweats, agitation and increased glucose levels in the blood (glucose output from the liver). It would thus be beneficial to be able to activate ARs without activating these classical secondary messengers, such as cAMP, to increase glucose uptake in peripheral tissues without stimulating the unwanted side effects.

Glucose uptake is mainly stimulated via facilitative glucose transporters (GLUT) that mediate glucose uptake into most cells. GLUTs are transporter proteins that mediate transport of glucose and/or fructose over the plasma membrane down the concentration gradient. There are fourteen known members of the GLUT family, named GLUT1-14, divided into three classes (Class I, Class II and Class III) dependent on their substrate specificity and tissue expression. GLUT1 and GLUT4 are the most intensively studied isoforms and, together with GLUT2 and GLUT3, belong to Class I which mainly transports glucose (in contrast to Class II that also transports fructose). GLUT1 is ubiquitously expressed and is responsible for basal glucose transport. GLUT4 is only expressed in peripheral tissues such as skeletal muscle, cardiac muscle and adipose tissues. GLUT4 has also been reported to be expressed in, for example, the brain, kidney, and liver. GLUT4 is the major isoform involved in insulin stimulated glucose uptake. The mechanism whereby insulin signalling increases glucose uptake is mainly via GLUT4 translocation from intracellular storage to the plasma membrane. It is known that GLUT4 translocation is induced by stimulation of the $β_2$-adrenergic receptor.

Thus, a possible treatment of a condition involving dysregulation of glucose homeostasis or glucose uptake in a mammal, such as type 2 diabetes, would involve the activation of the $β_2$-adrenergic receptor leading to GLUT4 translocation to the plasma membrane and promotion of glucose uptake into skeletal muscle leading to normalization of whole body glucose homeostasis. In addition, it would be advantageous if the treatment does not involve signalling through cAMP as this would lead to a favourable side-effect profile.

The vasodilator 4-(2-(butylamino)-1-hydroxyethyl)phenol, which has been used in the treatment of peripheral vascular disorders, has been found to initially increase blood sugar and has been contraindicated in diabetes and prediabetes (see Unger, H., *Zeitschrift für die Gesamte Innere Medizin und Ihre Grenzgebiete*, 16, 742 (1961)).

DESCRIPTION OF THE INVENTION

We have now surprisingly found that certain heteroaryl substituted p-hydroxyethylamines acting as agonists at the $β_2$-adrenergic receptor increase glucose uptake in skeletal muscle.

In addition, we have found that this effect is not mediated through significant cAMP release, such that many of the commonly described side effects seen with traditional $β_2$-adrenergic agonists (e.g. tachycardia, palpitation, tremor, sweats, agitation, and the like) can be reduced.

The use of such compounds in medicine represents a promising strategy for the treatment of conditions characterized by high blood sugar levels (i.e. hyperglycaemia), such as type 2 diabetes.

Compounds of the Invention

In a first aspect of the invention, there is provided a compound of formula I

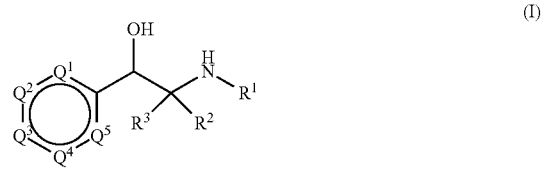

or a pharmaceutically acceptable salt thereof, wherein:
$R^1$ represents $C_{1-12}$ alkyl optionally substituted by one or more halo;
$R^2$ and $R^3$ each independently represent H or $C_{1-3}$ alkyl optionally substituted by one or more halo;

or R² and R³ may be linked together to form, together with the carbon atom to which they are attached, a 3- to 6-membered ring, which ring optionally is substituted by one or more groups independently selected from halo and C₁ alkyl optionally substituted by one or more halo;

the ring comprising $Q^1$ to $Q^5$ represents a 5- or 6-membered heteroaryl optionally substituted with one or more X, each X independently represents, as appropriate, halo, $R^a$, —CN, —N₃, —N($R^b$)$R^c$, —NO₂, —ONO₂, —$OR^d$, $S(O)_pR^e$ or —$S(O)N(R^f)R^g$;

$R^a$ represents $C_{1-6}$ alkyl optionally substituted by one or more groups independently selected from G;

each $R^b$, $R^c$, $R^d$, $R^e$, $R^f$ and $R^g$ independently represents H or $C_{1-6}$ alkyl optionally substituted by one or more groups independently selected from G;

or alternatively any of $R^b$ and $R^c$ and/or $R^f$ and $R^g$ may be linked together to form, together with the nitrogen atom to which they are attached, a 4- to 6-membered ring, which ring optionally contains one further heteroatom and which ring optionally is substituted by one or more groups independently selected from halo, $C_{1-3}$ alkyl optionally substituted by one or more halo, and =O;

G represents halo, —CN, —N($R^{a1}$)$R^{b1}$, —OR, —$S(O)_pR^{d1}$, —$S(O)_qN(R^{e1})R^{f1}$ or =O;

each $R^{a1}$, $R^{b1}$, $R^{c1}$, $R^{d1}$, $R^{e1}$ and $R^{f1}$ independently represents H or $C_{1-6}$ alkyl optionally substituted by one or more halo;

or alternatively any of $R^{a1}$ and $R^{b1}$ and/or $R^{e1}$ and $R^{f1}$ may be linked together to form, together with the nitrogen atom to which they are attached, a 4- to 6-membered ring, which ring optionally contains one further heteroatom and which ring optionally is substituted by one or more groups independently selected from halo, $C_{1-3}$ alkyl optionally substituted by one or more halo, and =O;

each p independently represents 0, 1 or 2; and
each q independently represents 1 or 2, which compounds (including pharmaceutically acceptable salts) may be referred to herein as the "compounds of the invention".

For the avoidance of doubt, the skilled person will understand that references herein to compounds of particular aspects of the invention (such as the first aspect of the invention, e.g. compounds of formula I) will include references to all embodiments and particular features thereof, which embodiments and particular features may be taken in combination to form further embodiments.

Unless indicated otherwise, all technical and scientific terms used herein have the same meaning as commonly understood by one of ordinary skill in the art to which this invention pertains.

Pharmaceutically acceptable salts include acid addition salts and base addition salts. Such salts may be formed by conventional means, for example by reaction of a free acid or a free base form of a compound of the invention with one or more equivalents of an appropriate acid or base, optionally in a solvent, or in a medium in which the salt is insoluble, followed by removal of said solvent, or said medium, using standard techniques (e.g. in vacuo, by freeze-drying or by filtration). Salts may also be prepared by exchanging a counter-ion of a compound of the invention in the form of a salt with another counter-ion, for example using a suitable ion exchange resin.

Particular acid addition salts that may be mentioned include carboxylate salts (e.g. formate, acetate, trifluoroacetate, propionate, isobutyrate, heptanoate, decanoate, caprate, caprylate, stearate, acrylate, caproate, propiolate, ascorbate, citrate, glucuronate, glutamate, glycolate, α-hydroxybutyrate, lactate, tartrate, phenylacetate, mandelate, phenylpropionate, phenylbutyrate, benzoate, chlorobenzoate, methylbenzoate, hydroxybenzoate, methoxybenzoate, dinitrobenzoate, o-acetoxy-benzoate, salicylate, nicotinate, isonicotinate, cinnamate, oxalate, malonate, succinate, suberate, sebacate, fumarate, malate, maleate, hydroxymaleate, hippurate, phthalate or terephthalate salts), halide salts (e.g. chloride, bromide or iodide salts), sulphonate salts (e.g. benzenesulphonate, methyl-, bromo- or chloro-benzenesulphonate, xylenesulphonate, methanesulphonate, ethanesulphonate, propanesuphonate, hydroxy-ethanesulphonate, 1- or 2-naphthalene-sulphonate or 1,5-naphthalenedisulphonate salts) or sulphate, pyrosulphate, bisulphate, sulphite, bisulphite, phosphate, monohydrogenphosphate, dihydrogenphosphate, metaphosphate, pyrophosphate or nitrate salts, and the like.

Particular acid addition salts that may be mentioned include the hydrochloride salt.

For the avoidance of doubt, the skilled person will understand that acid addition salts may include diacid salts (e.g. dihydrochloride salts).

Particular base addition salts that may be mentioned include salts formed with alkali metals (such as Na and K salts), alkaline earth metals (such as Mg and Ca salts), organic bases (such as ethanolamine, diethanolamine, triethanolamine, tromethamine and lysine) and inorganic bases (such as ammonia and aluminium hydroxide). More particularly, base addition salts that may be mentioned include Mg, Ca and, most particularly, K and Na salts.

For the avoidance of doubt, compounds of the first aspect of the invention may exist as solids, and thus the scope of the invention includes all amorphous, crystalline and part crystalline forms thereof, and may also exist as oils. Where compounds of the first aspect of the invention exist in crystalline and part crystalline forms, such forms may include solvates, which are included in the scope of the invention. Compounds of the first aspect of the invention may also exist in solution.

Compounds of the first aspect of the invention may contain double bonds and may thus exist as E (entgegen) and Z (zusammen) geometric isomers about each individual double bond. All such isomers and mixtures thereof are included within the scope of the invention.

Compounds of the first aspect of the invention may also exhibit tautomerism. All tautomeric forms and mixtures thereof are included within the scope of the invention. For example, a compound of the first aspect of the invention may be one wherein $Q^1$, $Q^4$ and $Q^5$ represent C—H, $Q^2$ represents N and $Q^3$ represents C—OH. In such instances the skilled person will understand that such a compound may exist in the 2-hydroxypyridine form (compound A) or in the 2-pyridone form (compound b), as depicted below.

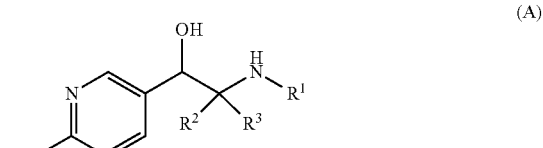

(A)

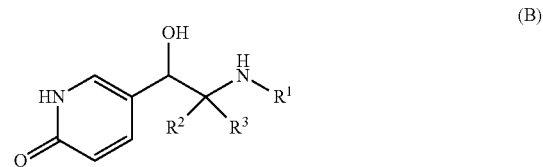

(B)

Compounds of the first aspect of the invention may also contain more than one asymmetric carbon atoms and may therefore exhibit optical and/or diastereoisomerism. Diastereoisomers may be separated using conventional techniques, e.g. chromatography or fractional crystallisation. The various stereoisomers (i.e. enantiomers) may be isolated by separation of a racemic or other mixture of the compounds using conventional, e.g. fractional crystallisation or HPLC, techniques. Alternatively the desired optical isomers may be obtained from appropriate optically active starting materials under conditions which will not cause racemisation or epimerisation (i.e. a 'chiral pool' method), by reaction of the appropriate starting material with a 'chiral auxiliary' which can subsequently be removed at a suitable stage, by derivatisation (i.e. a resolution, including a dynamic resolution); for example, with a homochiral acid followed by separation of the diastereomeric derivatives by conventional means such as chromatography, or by reaction with an appropriate chiral reagent or chiral catalyst all under conditions known to the skilled person. All stereoisomers and mixtures thereof are included within the scope of the invention.

As used herein, references to halo and/or halogen groups will each independently refer to fluoro, chloro, bromo and iodo (for example, fluoro (F) and chloro (Cl), such as F).

Unless otherwise specified, $C_{1-z}$ alkyl groups (where z is the upper limit of the range) defined herein may be straight-chain or, when there is a sufficient number (i.e. a minimum of three) of carbon atoms, be branched-chain, and/or cyclic (so forming a $C_{3-z}$-cycloalkyl group). When there is a sufficient number (i.e. a minimum of four) of carbon atoms, such groups may also be part cyclic. Part cyclic alkyl groups that may be mentioned include cyclopropylmethyl and cyclohexylethyl. When there is a sufficient number of carbon atoms, such groups may also be multicyclic (e.g. bicyclic or tricyclic) or spirocyclic. Such alkyl groups may also be saturated or, when there is a sufficient number (i.e. a minimum of two) of carbon atoms, be unsaturated (forming, for example, a $C_{2-z}$ alkenyl or a $C_{2-z}$ alkynyl group). Particular alkyl groups that may be mentioned include saturated alkyl groups.

As described herein, the ring comprising $Q^1$ to $Q^5$ (which may be referred to as ring Q) represents a 5- or 6-membered heteroaryl optionally substituted with one or more X.

As such, the skilled person will understand that representing $Q^1$ to $Q^5$ the ring may comprise, in addition to carbon atoms, one or more heteroatom, so as to form suitable heteroaryl groups as known to those skilled in the art. Moreover, the skilled person will understand that where the ring containing $Q^1$ to $Q^5$ is 5-membered, one of $Q^1$ to $Q^5$ (e.g. $Q^5$) will represent a direct bond (i.e. that group will not be present).

For the avoidance of doubt, the depiction of the ring containing the $Q^1$ to $Q^5$ groups with a circle therein (for example, such as in formula I) will be understood to indicate that the ring is aromatic.

Various heteroaryl groups will be well-known to those skilled in the art, such as pyridinyl, pyridonyl, pyrrolyl, furanyl, thiophenyl, oxadiazolyl, thiadiazolyl, thiazolyl, oxazolyl, pyrazolyl, triazolyl, tetrazolyl, isoxazolyl, isothiazolyl, imidazolyl and the like. The oxides of heteroaryl/heteroaromatic groups are also embraced within the scope of the invention (e.g. the N-oxide).

In particular, the term heteroaryl (or heteroaromatic) includes references to 5-membered or 6-membered heteroaromatic groups containing at least one N atom and optionally one additional heteroatoms selected (e.g. from oxygen, nitrogen and/or sulfur). Particular heteroaryl groups that may be mentioned include those comprising, in the heteroaryl ring, at least one N atom.

Particular heteroaryl groups (e.g. representing ring Q) that may be mentioned include thiazolyl (e.g. thiazol-4-yl and thiazol-5-yl, also thiazol-2-yl), pyrimidinyl (e.g. pyrimidin-4-yl or pyrimidin-5-yl) and pyridonyl (e.g. pyridon-4-yl or pyridon-5-yl). For the avoidance of doubt, the skilled person will understand that pyridonyl groups may exist as the aromatic tautomers thereof, i.e. as hydroxy pyridinyl groups.

Further heteroaryl groups (e.g. representing ring Q) that may be mentioned include pyridinyl (e.g. pyridin-2-yl, pyridin-3-yl and pyridine-4-yl).

As will be understood by those skilled in the art, substituents on heteroaryl groups may, as appropriate, be located on any atom in the ring system, including a heteroatom (i.e. a N atom). In such circumstances, the skilled person will understand that reference to the substituent being present "as appropriate" will indicate that certain substituents may only be present in positions wherein the presence of such a substituent is chemically allowable, as understood by those skilled in the art.

For example, where X is present on a N atom (in which case, it may be referred to as $X^1$), each X may independently represent $R^a$. Similarly, where X is present on a C atom (in which case, it may be referred to as $X^2$), each X may independently represent halo, $R^a$, —CN, —N$_3$, —N(R$^b$)R$^c$, —NO$_2$, —ONO$_2$, —OR$^d$, S(O)$_p$R$^e$ or —S(O)N(R$^f$)R$^g$.

For the avoidance of doubt, the skilled person will understand that the identities of $Q^1$ to $Q^5$ will be selected such that the resulting heteroaryl is a suitable heteroaryl as known to those skilled in the art.

For example, the skilled person will understand that in 5-membered heteroaryl rings there can only be one O or S, but up to four N atoms (with up to four heteroatoms in total), which may be present as N or NX$^1$ (particularly, with up to one being present as NX$^1$ and the remainder being present as N), as appropriate. Similarly, in a 6-membered heteroaryl ring there will be no O or S present in the ring but up to four (e.g. one or two) N atoms, which will be present as N.

For the avoidance of doubt, as used herein, references to heteroatoms will take their normal meaning as understood by one skilled in the art. Particular heteroatoms that may be mentioned include phosphorus, selenium, tellurium, silicon, boron, oxygen, nitrogen and sulphur (e.g. oxygen, nitrogen and sulphur).

For the avoidance of doubt, references to polycyclic (e.g. bicyclic or tricyclic) groups (e.g. when employed in the context of cycloalkyl groups) will refer to ring systems wherein at least two scissions would be required to convert such rings into a straight chain, with the minimum number of such scissions corresponding to the number of rings defined (e.g. the term bicyclic may indicate that a minimum of two scissions would be required to convert the rings into a straight chain). For the avoidance of doubt, the term bicyclic (e.g. when employed in the context of alkyl groups) may refer to groups in which the second ring of a two-ring system is formed between two adjacent atoms of the first ring, and may also refer to groups in which two non-adjacent atoms are linked by an alkylene group, which later groups may be referred to as bridged.

The present invention also embraces isotopically-labelled compounds of the present invention which are identical to those recited herein, but for the fact that one or more atoms are replaced by an atom having an atomic mass or mass number different from the atomic mass or mass number usually found in nature (or the most abundant one found in nature). All isotopes of any particular atom or element as specified herein are contemplated within the scope of the compounds of the invention. Hence, the compounds of the invention also include deuterated compounds, i.e. in which one or more hydrogen atoms are replaced by the hydrogen isotope deuterium.

For the avoidance of doubt, in cases in which the identity of two or more substituents in a compound of the invention may be the same, the actual identities of the respective substituents are not in any way interdependent. For example, in the situation in which two or more X groups are present, those X groups may be the same or different. Similarly, where two or more X groups are present and each represent halo, the halo groups in question may be the same or different. Likewise, when more than one $R^a$ is present and each independently represents $C_{1-6}$ alkyl substituted by one or more G group, the identities of each G are in no way interdependent.

The skilled person will appreciate that compounds of the invention that are the subject of this invention include those that are stable. That is, compounds of the invention include those that are sufficiently robust to survive isolation, e.g. from a reaction mixture, to a useful degree of purity.

All embodiments of the invention and particular features mentioned herein may be taken in isolation or in combination with any other embodiments and/or particular features mentioned herein (hence describing more particular embodiments and particular features as disclosed herein) without departing from the disclosure of the invention.

For the avoidance of doubt, the skilled person will understand that in a particular embodiment the ring comprising $Q^1$ to $Q^5$ represents a 5- or 6-membered heteroaryl substituted with one or more X. Thus, where substituents present on the ring comprising $Q^1$ to $Q^5$ are represented by $X^1$ and $X^2$, at least one $X^1$ or $X^2$ represents other than H (e.g. in embodiments where $X^1$ represents H, at least one $X^2$ represents other than H).

In certain embodiments of the first aspect of the invention, $R^1$ represents $C_{2-12}$ alkyl optionally substituted by one or more F, such as $C_{2-8}$ alkyl optionally substituted by one or more F.

In certain embodiments of the first aspect of the invention, $R^1$ represents $C_{3-12}$ alkyl optionally substituted by one or more F, such as $C_{3-8}$ alkyl optionally substituted by one or more F.

In particular embodiments of the first aspect of the invention, $R^1$ represents $C_{4-12}$ alkyl optionally substituted by one or more F, such as $C_{4-8}$ alkyl optionally substituted by one or more F.

In more particular embodiments of the first aspect of the invention, $R^1$ represents $C_{4-6}$ alkyl optionally substituted by one or more F, such as $C_4$ alkyl optionally substituted by one or more F.

In alternative embodiments of the first aspect of the invention, $R^1$ represents $C_{4-10}$ alkyl optionally substituted by one or more F, such as $C_{4-6}$ alkyl optionally substituted by one or more F.

In particular embodiments, $R^1$ represents a group of structure (i.e. substructure)

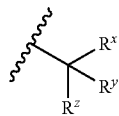

wherein:
$R^x$, $R^y$ and $R^z$ each independently represent H or $C_{1-11}$ alkyl (such as $C_{1-9}$ alkyl, e.g. such as $C_{1-7}$ alkyl) optionally substituted by one or more F;

or alternatively $R^x$ and $R^z$ be linked together to form, together with the carbon atom to which they are attached, a 3- to 6-membered ring, which ring is optionally substituted by one or more F.

As used herein, the skilled person will understand that bonds terminating with ⌇ represents the point of attachment (e.g. to the essential N atom in compounds of formula I, including all embodiments thereof).

For the avoidance of doubt, the skilled person will understand that, where $R^1$ is represented by the substructure bearing $R^x$, $R^y$ and $R^z$ groups, the sum total of carbons presented in the $R^x$, $R^y$ and $R^z$ groups, together with the carbon to which they are attached, may not exceed those present in the corresponding $R^1$ groups, as defined herein (including all embodiments thereof).

For the avoidance of doubt, groups forming part of structures representing $R^1$ (e.g. $R^x$, $R^y$ and $R^z$, and the carbon to which they are attached) may be optionally substituted as defined herein for $R^1$.

In further particular embodiments, $R^1$ may represent

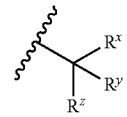

wherein $R^x$, $R^y$ and $R^z$ each independently represent H or $C_{1-11}$ alkyl, as appropriate (e.g. methyl, ethyl or n-propyl).

In particular embodiments, $R^x$, $R^y$ and $R^z$ each represent methyl.

In more particular embodiments, $R^1$ may represent

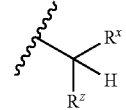

wherein $R^x$ and $R^z$ each independently represent H or $C_{1-11}$ alkyl, as appropriate (e.g. methyl, ethyl or n-propyl). In particular embodiments, when $R^x$ and $R^z$ are not H, they may be the same (e.g. $R^x$ and $R^z$ may both be methyl, such that $R^1$ may be isopropyl).

In alternative embodiments, when $R^x$ and $R^z$ are not H, they may be different (e.g. R may be propyl and $R^z$ methyl, i.e. $R^1$ may be 2-pentyl).

In such instances, the skilled person will recognize that the carbon to which $R^x$ and $R^z$ is a stereocentre and therefore $R^1$ may be depicted as

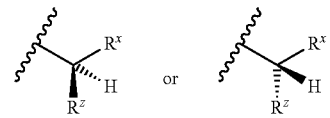

The skilled person will understand that such a stereocentre may be referred to as being in either the (R) or (S) configuration, depending on whether $R^x$ or $R^z$ is assigned a higher priority (according to the Cahn-Ingold-Prelog system, as understood by those skilled in the art).

In particular such embodiments, $R^x$ and $R^z$ may each independently represent $C_{1-11}$ alkyl wherein $R^x$ is a larger alkyl group (i.e. has a greater number of carbons atoms forming said alkyl group) than $R^z$. For example, in such embodiments $R^z$ may represent $C_{1-2}$ alkyl and $R^x$ may represent $C_{3-10}$ alkyl.

In alternative embodiments, $R^1$ may represent

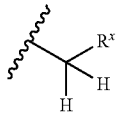

wherein R represents H or $C_{1-11}$ alkyl, such as methyl, ethyl or n-propyl (i.e. $R^1$ may be methyl, ethyl, n-propyl or n-butyl).

Accordingly, in particular embodiments of the invention $R^1$ may be methyl, ethyl, n-propyl, isopropyl n-butyl, sec-butyl, t-butyl or 2-pentyl. In particular, $R^1$ may represent n-butyl. More particularly, $R^1$ may represent tert-butyl.

In particular embodiments of the first aspect of the invention, each $R^2$ and $R^3$ independently represents H or $C_{1-2}$ alkyl (e.g. methyl).

The skilled person will understand that the prefixes "n-", "sec-" and "tert-" when applied to alkyl groups indicate the terms "normal", "secondary" and "tertiary". The term "normal" indicates a linear alkyl group where the point of attachment of the group to the rest of a molecule is through a carbon atom at the end of the carbon chain and thus that that carbon atom is bound to one other carbon atom. The term "secondary" indicates that the point of attachment of the rest of the molecule to the alkyl group is through a carbon atom adjacent to the end of the carbon chain and thus that that carbon is itself bound to two other carbon atoms. The term "tertiary" indicates that the point of attachment of the alkyl group to the rest of a molecule is through a carbon atom that is bound to three other carbon atoms.

In further embodiments of the first aspect of the invention, each $R^2$ and $R^3$ independently represents H, methyl or ethyl.

In more particular embodiments, $R^2$ and $R^3$ each represent H.

In a particular embodiment, there are provided compounds of the invention wherein:
any one of $Q^1$ to $Q^5$ represents, as appropriate, O, S, N or $NX^1$, and up to three (e.g. up to one) more of $Q^1$ to $Q^5$ may represent N,
wherein the remainder of $Q^1$ to $Q^5$ each represent $CX^2$, or alternatively $Q^5$ may represent a direct bond;
each $X^1$, where present, independently represents H or $R^a$;
each $X^2$ independently represents H, halo, $R^a$, —CN, —$N_3$, —N($R^b$)$R^c$, —$NO_2$, —$ONO_2$, —$OR^d$, —S(O)$_p R^e$ or —S(O)$_q$N($R^f$)$R^g$.

In more particular such embodiments, either:
(a) for a 5-membered heteroaryl
$Q^5$ represents a direct bond,
any one of $Q^1$ to $Q^4$ represents, as appropriate, O, S, N or $NX^1$, and up to three (e.g. up to one) more of $Q^1$ to $Q^5$ may represent N,
and the remainder of $Q^1$ to $Q^5$ each represent $CX^2$; and
(b) for a 6-membered heteroaryl
any one to four (e.g. one or two) of $Q^1$ to $Q^5$ represents N, and the remainder of $Q^1$ to $Q^5$ each represent $CX^2$.

Thus, either:
$Q^5$ represents a direct bond,
any one of $Q^1$ to $Q^4$ represents, as appropriate, O, S, N or $NX^1$, and up to three (e.g. up to one) more of $Q^1$ to $Q^4$ may represent N,
and the remainder of $Q^1$ to $Q^4$ each represent $CX^2$;
or
any one to four (e.g. one or two) of $Q^1$ to $Q^5$ represents N, and the remainder of $Q^1$ to $Q^5$ each represent $CX^2$ (e.g. wherein at least one $X^2$ represents other than H).

Particular heteroaryl groups that may be mentioned are those comprising at least one N atom. More particular heteroaryl groups that may be mentioned are those wherein one of $Q^1$ to $Q^5$ represents N (e.g. $Q^2$ or $Q^4$ represents N) and the remainder of $Q^1$ to $Q^5$ represents $CX^2$.

Thus, in particular embodiments, where $Q^5$ represents a direct bond, any one of $Q^1$ to $Q^4$ represents, as appropriate, O, S, N or $NX^1$, and up to three (e.g. up to one) more of $Q^1$ to $Q^4$ may represent N,
and the remainder of $Q^1$ to $Q^4$ each represent $CX^2$,
provided that at least one of $Q^1$ to $Q^4$ represents N or $NX^1$, In particular embodiments, each $X^1$, were present, represents H.

In certain embodiments, there is provided a compound of the invention wherein:
each $X^2$ independently represents H, halo, $R^a$, —CN, —$N_3$, —N($R^b$)$R^c$, —$NO_2$ or $OR^d$ wherein $R^a$ represents $C_{1-4}$ alkyl optionally substituted by one or more F, and $R^b$, $R^c$ and $R^d$ each independently represent H or $C_{1-4}$ alkyl optionally substituted by one or more F or =O.

In particular embodiments, there is provided a compound of the invention wherein each $X^2$ independently represents H, halo, $R^a$, —CN, —$N_3$, —$NO_2$ or —$OR^d$, particularly wherein $R^a$ represents $C_{1-4}$ alkyl optionally substituted by one or more F, and $R^b$, $R^c$ and $R^d$ each independently represent H or $C_{1-4}$ alkyl optionally substituted by one or more F or =O.

In more particular embodiments, there is provided a compound of the invention wherein each $X^2$ independently represents H, halo, —CN, $R^a$ or —$OR^d$ (e.g. wherein at least one $X^2$ represents other than H), particularly wherein $R^d$ represents H.

In yet more particular embodiments, there is provided a compound of the invention wherein each $X^2$ independently represents H, halo (e.g. F), $R^a$ or —OH (e.g. wherein at least one $X^2$ represents other than H).

In yet more particular embodiments, there is provided a compound of the invention wherein each $X^2$ independently represents H, halo (e.g. F), —$CF_3$ or —OH (e.g. wherein at least one $X^2$ represents other than H).

In further embodiments, each $X^2$ may independently represent H, halo, $R^a$, —CN, —N($R^b$)$R^c$ or —$OR^d$, wherein $R^a$ represents $C_{1-4}$ alkyl optionally substituted by one or more F, and $R^b$, $R^c R^d$ each independently represent H or $C_{1-4}$ alkyl optionally substituted by one or more F or =O.

In more particular embodiments, each $X^2$ independently represents H, F, Cl, $R^a$, —$NH_2$, —NHC(O)$CH_3$, —CN or —OH, wherein $R^a$ represents $C_{1-4}$ alkyl (e.g. $C_{1-2}$ alkyl) optionally substituted by one or more F (for example $R^a$ represents —$CH_3$, —$CHF_2$ or —$CF_3$ (e.g. —$CF_3$)).

In yet more particular embodiments, each $X^2$ independently represents H, F, Cl, $R^a$, —$NH_2$, —NHC(O)$CH_3$, or —OH, wherein $R^a$ represents $C_{1-2}$ alkyl optionally substituted by 1 or more F.

In particular embodiments, $R^a$ does not represent —$CH_2$—OH.

In yet further particular embodiments, each $X^2$ independently represents H, F, —$NH_2$, —NHC(O)$CH_3$, —$CF_3$ or —OH (e.g. wherein at least one $X^2$ represents other than H).

In particular embodiments of the invention, there is provided a compound of formula I wherein each $X^2$ independently represents H, F, —$NH_2$, —NHC(O)$CH_3$, —$CF_3$ or —OH (e.g. —$NH_2$, —OH or —$CF_3$).

In certain embodiments, each $X^2$ independently represents H, F, C, —CN, —$NH_2$, —$CH_3$, —$CF_3$ or —OH (e.g. wherein at least one $X^2$ represents other than H).

In certain embodiments, each $X^2$ independently represents H, F, C, —CN, —CH$_3$, —CF$_3$ or —OH (e.g. wherein at least one $X^2$ represents other than H).

In certain embodiments, each $X^2$ independently represents H, F, C, —CH$_3$, —CF$_3$ or —OH (e.g. wherein at least one $X^2$ represents other than H).

In certain embodiments, each $X^2$ independently represents H, F, C, —CF$_3$ or —OH (e.g. wherein at least one $X^2$ represents other than H).

For example, in particular embodiments each $X^2$ independently represents H or F, such as wherein one $X^2$ represents F and the remainder of the $X^2$ groups present represent H.

In certain embodiments that may be mentioned, at least one $X^2$ group is present and does not represent H (i.e. at least one $X^2$ group is present and is other than H).

In certain embodiments that may be mentioned, when more than one $X^2$ substituent is present, no more than one $X^2$ may represent a group selected from —N(R$^b$)R$^c$ and —OR$^d$ (particularly where R$^b$, R$^c$ and R$^d$ represent H).

In yet more particular embodiments:
$Q^1$ represents N;
$Q^2$ and $Q^3$ each independently represent N, CNH$_2$ or COH; and
$Q^4$ and $Q^5$ each represent CH.

In other particular embodiments of the invention:
$Q^1$ and $Q^5$ each represent CH;
$Q^2$ and $Q^3$ each independently represent N, CNH$_2$ or COH; and
$Q^4$ represents N.

In certain embodiments of the invention:
$Q^1$, $Q^4$ and $Q^5$ represent CH;
at least one of $Q^2$ or $Q^3$ represents N and the other represents CX$^2$; and
$X^2$ represents F, —NH$_2$, —NHC(O)CH$_3$, —CF$_3$ or —OH (e.g. F).

In certain embodiments of the invention:
at least one of $Q^1$, $Q^2$ or $Q^3$ represents N and the remainder of $Q^1$ to $Q^5$ represents CX$^2$; and
one $X^2$ represents F or Cl, and the remainder represent H.

For the avoidance of doubt, when $R^1$ represents n-butyl, $R^2$ and $R^3$ represent H, $Q^1$ represents N, $Q^2$ represents CNH$_2$, $Q^3$ represents N and $Q^4$ and $Q^5$ represent CH, the compound of formula I may be depicted as:

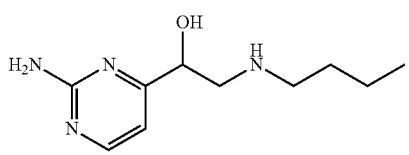

In certain embodiments, $Q^5$ represents a direct bond. In such instances, the ring containing the $Q^1$ to $Q^5$ groups (ring Q) is a 5-membered heteroaryl ring.

In particular embodiments:
at least one of $Q^1$ to $Q^3$ represents N;
the remainder of $Q^1$ to $Q^3$ each independently represent N or CX$^2$, or one of the remainder of $Q^1$ to $Q^3$ may alternatively represent O or S (e.g. S);
$Q^4$ represents CH; and
$Q^5$ represents a direct bond,
particularly wherein each $X^2$ independently represents H, F, —NH$_2$, —NHC(O)CH$_3$, —CF$_3$ or —OH (e.g. H, —NH$_2$, or —CF$_3$ or —OH).

In even more particular embodiments, there are provided compounds of formula I wherein:
$Q^1$ represents N;
$Q^2$ represents CNH$_2$ or CCF$_3$;
$Q^3$ represents S;
$Q^4$ represents CH; and
$Q^5$ represents a direct bond.

In alternative particular embodiments, there are provided compounds of formula I wherein:
$Q^1$ represents S;
$Q^2$ represents CNH$_2$ or CCF$_3$;
$Q^3$ represents N;
$Q^4$ represents CH; and
$Q^5$ represents a direct bond.

In certain embodiments, there are provided compounds of formula I wherein:
$Q^1$ represents CH;
$Q^2$ represents CF or C—Cl (e.g. CF);
$Q^3$ represents CH;
$Q^4$ represents N; and
$Q^5$ represents CH.

In certain embodiments that may be mentioned, $R^d$ represents H.

In further embodiments, does not G represent —OH.

In yet further embodiments, G represents halo (e.g. F).

For the avoidance of doubt, when $R^1$ represents n-butyl, $R^2$ and $R^3$ represent H, $Q^1$ represents N, $Q^2$ represents CNH$_2$, $Q^3$ represents S, $Q^4$ represents CH$_2$ and $Q^5$ represents a chemical bond, the compound of formula I may be depicted as:

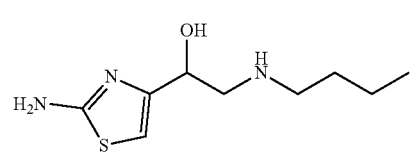

For the avoidance of doubt, the skilled person will understand that groups representing $Q^1$ to $Q^5$ may be depicted in relation to compounds of formula I without departing from the teaching of the invention.

For example, where $Q^4$ represents N and each of $Q^1$, $Q^2$, $Q^3$ and $Q^5$ represents CH or CX$^2$, the resulting compound may be more conveniently represented as a compound as depicted below:

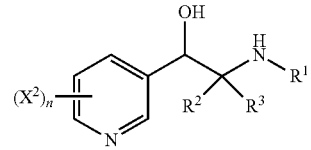

wherein $R^1$, $R^2$, $R^3$ and $X^2$ are as defined herein and n represents 0 to 4 (e.g. 0 to 2, such as 1 or 2, e.g. 1).

The skilled person will understand that particular Q groups (and the positions and number thereof, such as may correspond to $Q^1$ to $Q^5$ groups in compounds of formula I, provided that at least one of $Q^1$ to $Q^5$ represent N) that may be mentioned include those present in the examples provided herein.

Similarly, the skilled person will understand that particular $R^1$, $R^2$ and $R^3$ groups, groups representing ring Q, and $X^1$ and $X^2$ groups that may be mentioned include those present in the examples provided herein.

Particular compounds of the first aspect of the invention that may be mentioned include the compounds of the examples provided herein, and pharmaceutically acceptable salts thereof.

For example, compounds of formula I that may be mentioned include:
1-(2-Aminothiazol-4-yl)-2-(butylamino)ethan-1-ol;
2-(Butylamino)-1-(2-(trifluoromethyl)thiazol-4-yl)ethan-1-ol;
4-(2-(Butylamino)-1-hydroxyethyl)pyridin-2(1H)-one;
5-(2-(Butylamino)-1-hydroxyethyl)pyridin-2(1H)-one; and
1-(2-Aminopyrimidin-4-yl)-2-(butylamino)ethan-1-ol,
and pharmaceutically acceptable salts thereof.

Further compounds of formula I that may be mentioned include:
2-(Butylamino)-1-(pyridin-4-yl)ethan-1-ol;
2-(Butylamino)-1-(pyridin-3-yl)ethan-1-ol;
N-(5-(2-(Butylamino)-1-hydroxyethyl)thiazol-2-yl)isobutyramide;
1-(2-Aminothiazol-5-yl)-2-(butylamino)ethan-1-ol dihydrochloride;
N-(5-(2-(Butylamino)-1-hydroxyethyl)pyrimidin-2-yl) isobutyramide;
1-(2-Aminopyrimidin-5-yl)-2-(butylamino)ethan-1-ol
6-(2-(tert-Butylamino)-1-hydroxyethyl)pyridin-3-ol
5-(2-(tert-Butylamino)-1-hydroxyethyl)pyridin-3-ol;
4-(2-(tert-Butylamino)-1-hydroxyethyl)pyridin-3-ol;
4-(2-(tert-Butylamino)-1-hydroxyethyl)-1-methylpyridin-2(1H)-one;
2-(tert-Butylamino)-1-(5-fluoropyridin-2-yl)ethan-1-ol;
2-(tert-Butylamino)-1-(5-fluoropyridin-3-yl)ethan-1-ol;
2-(tert-Butylamino)-1-(3-fluoropyridin-4-yl)ethan-1-ol;
2-(tert-Butylamino)-1-(5-chloropyridin-3-yl)ethan-1-ol;
2-(tert-Butylamino)-1-(3-chloropyridin-2-yl)ethan-1-ol; and
2-(tert-Butylamino)-1-(5-chloropyridin-2-yl)ethan-1-ol,
and pharmaceutically acceptable salts thereof.

As described herein, compounds of the first aspect of the invention may also contain one or more asymmetric carbon atoms and may therefore exhibit optical and/or diastereoisomerism. Moreover, it has been found that certain such optical and/or diastereoisomers may show increased utility in the treatment of hyperglycaemia or disorders characterized by hyperglycaemia (such as type 2 diabetes), as described herein.

In a particular embodiment of the first aspect of the invention, the compound of formula I is such that the carbon substituted with the essential —OH group is in the (R) configuration, as understood by those skilled in the art.

Alternatively, the compound of formula I is such that the carbon substituted with the essential —OH group is in the (S) configuration, as understood by those skilled in the art.

Thus, in a particular embodiment, the compound of formula I is a compound of formula IA

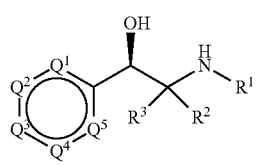

(IA)

wherein $Q^1$ to $Q^5$ (and, therefore, ring Q), $R^1$, $R^2$ and $R^3$ are as defined herein.

Similarly, the skilled person will understand that groups representing $Q^1$ to $Q^5$ may be depicted in relation to compounds of formula IA without departing from the teaching of the invention.

For example, where $Q^4$ represents N and each of $Q^1$, $Q^2$, $Q^3$ and $Q^5$ represents CH or $CX^2$, the resulting compound may be more conveniently represented as a compound as depicted below:

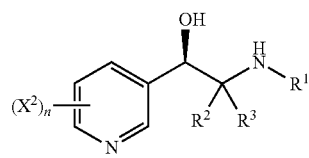

wherein $R^1$, $R^2$, $R^3$ and $X^2$ are as defined herein and n represents 0 to 4 (e.g. 0 to 2, such as 1 or 2, e.g. 1).

As described herein, particular compounds of the first aspect of the invention that may be mentioned include the compounds of the examples provided herein, and pharmaceutically acceptable salts thereof.

For example, compounds of formula IA that may be mentioned include:
(S)-1-(2-Aminothiazol-4-yl)-2-(butylamino)ethan-1-ol;
(S)-2-(Butylamino)-1-(2-(trifluoromethyl)thiazol-4-yl) ethan-1-ol; and
(S)-1-(2-Aminopyrimidin-4-yl)-2-(butylamino)ethan-1-ol,
and pharmaceutically acceptable salts thereof.

Further compounds of formula IA that may be mentioned include:
(S)—N-(5-(2-(Butylamino)-1-hydroxyethyl)thiazol-2-yl) isobutyramide;
(S)-1-(2-Aminothiazol-5-yl)-2-(butylamino)ethan-1-ol dihydrochloride;
(R)—N-(5-(2-(Butylamino)-1-hydroxyethyl)pyrimidin-2-yl)isobutyramide;
(R)-1-(2-Aminopyrimidin-5-yl)-2-(butylamino)ethan-1-ol
(S)-6-(2-(tert-Butylamino)-1-hydroxyethyl)pyridin-3-ol
(R)-5-(2-(tert-Butylamino)-1-hydroxyethyl)pyridin-3-ol;
(R)-4-(2-(tert-Butylamino)-1-hydroxyethyl)-1-methylpyridin-2(1H)-one;
(S)-2-(tert-Butylamino)-1-(5-fluoropyridin-2-yl)ethan-1-ol;
(R)-2-(tert-Butylamino)-1-(5-fluoropyridin-3-yl)ethan-1-ol;
(R)-2-(tert-Butylamino)-1-(3-fluoropyridin-4-yl)ethan-1-ol;
(R)-2-(tert-Butylamino)-1-(5-chloropyridin-3-yl)ethan-1-ol;
(S)-2-(tert-Butylamino)-1-(3-chloropyridin-2-yl)ethan-1-ol; and
(S)-2-(tert-Butylamino)-1-(5-chloropyridin-2-yl)ethan-1-ol,
and pharmaceutically acceptable salts thereof.

The skilled person will understand that references to a specific stereoisomer of a compound of formula I (e.g. in the case of compounds of formula I, where the carbon substituted by the essential —OH group is in, for example, the (R) configuration) will refer to the specific stereoisomer present in the substantial absence of the corresponding opposite stereoisomer (e.g. in the case of compounds of formula I, where the carbon substituted by the essential —OH group is in, for example, the (S) configuration).

For example, references to a compound of formula IA being present in the substantial absence of the corresponding opposite stereoisomer (i.e. as the case may be, in the (R) or (S) configuration) will refer to the substantial absence of the corresponding compound as depicted below.

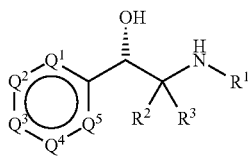

As used herein, references to the substantial absence of the corresponding opposite stereoisomer will refer to the desired stereoisomer (e.g. in the case of compounds of formula I, when the carbon substituted by the essential —OH group is in the (R) configuration) being present at a purity of at least 80% (e.g. at least 90%, such as at least 95%) relative to the opposite stereoisomer (e.g. in the case of compounds of formula I, when the carbon substituted by the essential —OH group is in the (S) configuration). Alternatively, in such instances, compounds may be indicated to be present in the substantial absence of the compound in the other configuration (i.e. for example, the (S) configuration), which may indicate that the compound in the relevant configuration is present in an enantiomeric excess (e.e.) of at least 90% (such as at least 95%, at least 98% or, particularly, at least 99%, for example at least 99.9%).

For the avoidance of doubt, compounds referred to as having a specific stereochemistry at a defined position (e.g. in the case of compounds of formula I, the carbon substituted by the essential —OH group being in the (R) or (S) configuration) may also have stereochemistry at one or more other positions, and so may exist as mixtures of enantiomers or diastereoisomers in relation to the stereochemistry at those positions.

In a certain embodiment that may be mentioned, the compound of the invention is not 6-[2-(tert-butylamino)-1-hydroxyethyl]-2-(hydroxymethyl)pyridin-3-ol (including (R)-6-[2-(tert-butylamino)-1-hydroxyethyl]-2-(hydroxymethyl)pyridin-3-ol and (S)-6-[2-(tert-butylamino)-1-hydroxyethyl]-2-(hydroxymethyl)pyridin-3-ol), or a pharmaceutically acceptable salt thereof.

Medical Uses

As indicated herein, the compounds of the invention, and therefore compositions and kits comprising the same, are useful as pharmaceuticals.

Thus, according to a second aspect of the invention there is provided a compound of the first aspect of the invention, as hereinbefore defined (i.e. a compound as defined in the first aspect of the invention, including all embodiments and particular features thereof), for use as a pharmaceutical (or for use in medicine).

For the avoidance of doubt, references to compounds as defined in the first aspect of the invention will include references to compounds of formula I (including all embodiments thereof) and pharmaceutically acceptable salts thereof.

As indicated herein, the compounds of the invention may be of particular use in treating hyperglycaemia or a disorder characterized by hyperglycaemia.

Thus, in a third aspect of the invention, there is provided a compound of the first aspect of the invention, as hereinbefore defined, for use in the treatment of hyperglycaemia or a disorder characterized by hyperglycaemia.

In an alternative third aspect of the invention, there is provided the use of a compound of formula I, or a pharmaceutically acceptable salt thereof, in the manufacture of a medicament for use in the treatment of hyperglycaemia or a disorder characterized by hyperglycaemia.

In a further alternative third aspect of the invention, there is provided a method of treating hyperglycaemia or a disorder characterized by hyperglycaemia comprising administering to a patient in need thereof a therapeutically effective amount of a compound of formula I, or a pharmaceutically acceptable salt thereof.

For the avoidance of doubt, the term "hyperglycaemia" as used herein will be understood by those skilled in the art to refer to a condition wherein an excessive amount of glucose circulates in blood plasma of the subject experiencing the same. In particular, it may refer to a subject (e.g a human subject) having blood glucose levels higher than about 10.0 mmol/L (such as higher than about 11.1 mmol/L, e.g. higher than about 15 mmol/L), although it may also refer to a subject (e.g a human subject) having blood glucose levels higher than about 7 mmol/L for an extended period of time (e.g. for greater than 24 hours, such as for greater than 48 hours).

The skilled person will understand that references to the treatment of a particular condition (or, similarly, to treating that condition) take their normal meanings in the field of medicine. In particular, the terms may refer to achieving a reduction in the severity of one or more clinical symptom associated with the condition. For example, in the case of type 2 diabetes, the term may refer to achieving a reduction of blood glucose levels. In particular embodiments, in the case of treating hyperglycaemia or conditions characterised by hyperglycaemia, the term may refer to achieving a reduction of blood glucose levels (for example, to or below about 10.0 mmol/mL (e.g. to levels in the range of from about 4.0 mmol/L to about 10.0 mmol/L), such as to or below about 7.5 mmol/mL (e.g. to levels in the range of from about 4.0 mmol/L to about 7.5 mmol/L) or to or below about 6 mmol/mL (e.g. to levels in the range of from about 4.0 mmol/L to about 6.0 mmol/L)).

As used herein, references to patients will refer to a living subject being treated, including mammalian (e.g. human) patients. Thus, in particular embodiments of the first aspect of the invention, the treatment is in a mammal (e.g. a human).

As used herein, the term therapeutically effective amount will refer to an amount of a compound that confers a therapeutic effect on the treated patient. The effect may be objective (i.e. measurable by some test or marker) or subjective (i.e. the subject gives an indication of and/or feels an effect).

Although compounds of the first aspect of the invention may possess pharmacological activity as such, certain pharmaceutically-acceptable (e.g. "protected") derivatives of compounds of the invention may exist or be prepared which may not possess such activity, but may be administered parenterally or orally and thereafter be metabolised in the body to form compounds of the invention. Such compounds (which may possess some pharmacological activity, provided that such activity is appreciably lower than that of the active compounds to which they are metabolised) may therefore be described as "prodrugs" of compounds of the invention.

As used herein, references to prodrugs will include compounds that form a compound of the invention, in an experimentally-detectable amount, within a predetermined time, following enteral or parenteral administration (e.g. oral or parenteral administration). All prodrugs of the compounds of the first aspect of the invention are included within the scope of the invention.

For the avoidance of doubt, the compounds of the first aspect of the invention are useful because they possess pharmacological activity, and/or are metabolised in the body following oral or parenteral administration to form compounds that possess pharmacological activity. In particular, as described herein, compounds of the first aspect of the invention are useful in the treatment of hyperglycaemia or disorders characterized by hyperglycaemia (such as type 2 diabetes), which terms will be readily understood by one of skill in the art (as described herein).

In a particular embodiment, the treatment is of a disorder (which may also be referred to as a condition or disease) characterised by hyperglycaemia.

In particular embodiments, compounds of the invention (i.e. compounds of formula I, including all embodiments thereof) are for use in the treatment of type 2 diabetes (or useful in the manufacture of a medicament for such treatment, or useful in a method for such treatment, as described herein).

In particular embodiments of the first aspect of the invention, the disorder is type 2 diabetes, such as type 2 diabetes of a sub-type selected from the list consisting of maturity-onset diabetes in the young (MODY), ketosis-prone diabetes in adults, latent autoimmune diabetes of adults (LADA), and gestational diabetes.

In further particular embodiments, the treatment of type 2 diabetes is in a non-obese patient.

For the avoidance of doubt, the skilled person will understand that patients with a Body Mass Index (BMI) of greater than 30 are considered to be obese.

In particular embodiments, the treatment may be of hyperglycaemia in a patient who is at risk of developing type 2 diabetes, which condition may be defined as pre-diabetes. Thus, compounds of the invention may be useful in the prevention of type 2 diabetes (e.g. in a patient having pre-diabetes).

As used herein, the term prevention (and, similarly, preventing) includes references to the prophylaxis of the disease or disorder (and vice-versa). As such, references to prevention may also be references to prophylaxis, and vice versa. In particular, the term may refer to achieving a reduction in the likelihood of the patient (or healthy subject) developing the condition (for example, at least a 10% reduction, such as at least a 20%, 30% or 40% reduction, e.g. at least a 50% reduction).

In more particular embodiments, the type 2 diabetes is characterised by the patient displaying severe insulin resistance (SIR).

In further embodiments, the treatment may be of hyperglycaemia in a patient having type 1 diabetes. Thus, compounds of the invention may be useful in the treatment of hyperglycaemia in type 1 diabetes.

The skilled person will understand that compounds of the invention may be useful in treating hyperglycaemia in patients having impaired insulin production, such as in patients having cystic fibrosis. Thus, in further embodiments, the disorder characterized by hyperglycaemia is cystic fibrosis-related diabetes.

In particular embodiments that may be mentioned, the disorder characterised by hyperglycaemia is (or is characterized by) severe insulin resistance (SIR), which may be understood by those in the art to refer to disorders wherein typically the subject has normal, or in some cases increased, insulin production but significantly reduced insulin sensitivity. In particular instances, such patients may be non-obese (e.g. being of a healthy weight). Thus, in particular embodiments, such treatments are performed in patients who are not defined as being obese (e.g. in patients who are defined as being of a healthy weight).

For example, SIR may be identified in a patient based in said patient having fasting insulin >150 pmol/L and/or a peak insulin on glucose tolerance testing of >1,500 pmol/L, particularly in individuals with a BMI<30 kg/m$^2$ (which patient may otherwise have normal glucose tolerance).

More particularly, SIR may be characterised by the patient having no significant response to the presence of insulin, which may result from a defect (e.g. a genetic defect) in the function of the insulin receptor.

Particular disorders that may be characterised by SIR include: Rabson-Mendenhall syndrome, Donohue's syndrome (leprechaunism), Type A and Type B syndromes of insulin resistance, the HAIR-AN (hyperandrogenism, insulin resistance, and acanthosis nigricans) syndromes, pseudo-acromegaly, and lipodystrophy.

More particular disorders that may be characterised by SIR include Donohue's syndrome and Type A syndrome of insulin resistance and, yet more particularly, Rabson-Mendenhall syndrome.

The skilled person will understand that treatment with compounds of the first aspect of the invention may further comprise (i.e. be combined with) further (i.e. additional/other) treatment(s) for the same condition. In particular, treatment with compounds of the invention may be combined with other means for the treatment of type 2 diabetes, such as treatment with one or more other therapeutic agent that is useful in the treatment of type 2 diabetes as known to those skilled in the art, such as therapies comprising requiring the patient to undergo a change of diet and/or undertake exercise regiments, and/or surgical procedures designed to promote weight loss (such as gastric band surgery).

In particular, treatment with compounds of the invention may be performed in combination with (e.g. in a patient who is also being treated with) one or more (e.g. one) additional compounds (i.e. therapeutic agents) that:
(i) are capable of reducing blood sugar levels; and/or
(ii) are insulin sensitizers; and/or
(iii) enhance insulin release,
all of which are described herein below.

In alternative embodiments, compounds of the first aspect of the invention (i.e. compounds of the invention) may be useful in the treatment of a non-alcoholic fatty liver disease (NAFLD).

Non-alcoholic fatty liver disease (NAFLD) is defined by excessive fat accumulation in the form of triglycerides (steatosis) in the liver (designated as an accumulation of greater than 5% of hepatocytes histologically). It is the most common liver disorder in developed countries (for example, affecting around 30% of US adults) and most patients are asymptomatic. If left untreated, the condition may progressively worsen and may ultimately lead to cirrhosis of the liver. NAFLD is particularly prevalent in obese patients, with around 80% thought to have the disease.

A sub-group of NAFLD patients (for example, between 2 and 5% of US adults) exhibit liver cell injury and inflammation in addition to excessive fat accumulation. This condition, designated as non-alcoholic steatohepatitis (NASH), is virtually indistinguishable histologically from alcoholic steatohepatitis. While the simple steatosis seen in NAFLD does not directly correlate with increased short-term morbidity or mortality, progression of this condition to NASH dramatically increases the risks of cirrhosis, liver failure and hepatocellular carcinoma. Indeed, NASH is now considered to be one of the main causes of cirrhosis (including cryptogenic cirrhosis) in the developed world.

The exact cause of NASH has yet to be elucidated, and it is almost certainly not the same in every patient. It is most closely related to insulin resistance, obesity, and the metabolic syndrome (which includes diseases related to diabetes mellitus type 2, insulin resistance, central (truncal) obesity, hyperlipidaemia, low high-density lipoprotein (HDL) cholesterol, hypertriglyceridemia, and hypertension). However, not all patients with these conditions have NASH, and not all patients with NASH suffer from one of these conditions. Nevertheless, given that NASH is a potentially fatal condition, leading to cirrhosis, liver failure and hepatocellular carcinoma, there exists a clear need for an effective treatment.

In particular embodiments, compounds of the invention (i.e. compounds of formula I, including all embodiments thereof) are for use in the treatment of a non-alcoholic fatty liver disease (or useful in the manufacture of a medicament for such treatment, or useful in a method for such treatment, as described herein).

The process by which the triglyceride fat accumulates in liver cells is called steatosis (i.e. hepatic steatosis). The skilled person will understand that the term "steatosis" encompasses the abnormal retention of fat (i.e. lipids) within a cell. Thus, in particular embodiments of the first aspect of the invention, the treatment or prevention is of a fatty liver disease which is characterized by steatosis.

During steatosis, excess lipids accumulate in vesicles that displace the cytoplasm of the cell. Over time, the vesicles can grow large enough to distort the nucleus, and the condition is known as macrovesicular steatosis. Otherwise, the condition may be referred to as microvesicular steatosis. Steatosis is largely harmless in mild cases; however, large accumulations of fat in the liver can cause significant health issues. Risk factors associated with steatosis include diabetes mellitus, protein malnutrition, hypertension, obesity, anoxia, sleep apnea and the presence of toxins within the cell.

As described herein, fatty liver disease is most commonly associated with alcohol or a metabolic syndrome (for example, diabetes, hypertension, obesity or dyslipidemia). Therefore, depending on the underlying cause, fatty liver disease may be diagnosed as alcohol-related fatty liver disease or non-alcoholic fatty liver disease (NAFLD).

Particular diseases or conditions that are associated with fatty liver disease that are not related to alcohol include metabolic conditions such as diabetes, hypertension, obesity, dyslipidemia, abetalipoproteinemia, glycogen storage diseases, Weber-Christian disease, acute fatty liver of pregnancy, and lipodystrophy. Other non-alcohol related factors related to fatty liver diseases include malnutrition, total parenteral nutrition, severe weight loss, refeeding syndrome, jejunoileal bypass, gastric bypass, polycystic ovary syndrome and diverticulosis.

The compounds of the invention have been found to be particularly useful in the treatment or prevention of NAFLD, which may be referred to as a fatty liver disease which is not alcohol related. A fatty liver disease which is "not alcohol related" may be diagnosed wherein alcohol consumption of the patient is not considered to be a main causative factor. A typical threshold for diagnosing a fatty liver disease as "not alcohol related" is a daily consumption of less than 20 g for female subjects and less than 30 g for male subjects.

If left untreated, subjects suffering from fatty liver disease may begin to experience inflammation of the liver (hepatitis). It has been postulated that one of the possible causes of this inflammation may be lipid peroxidative damage to the membranes of the liver cells. Inflammation of a fatty liver can lead to a number of serious conditions and it is therefore desirable to treat or prevent fatty liver disease before inflammation occurs. Thus, in particular embodiments of the first aspect of the invention, the treatment or prevention is of a NAFLD which is associated with inflammation.

Non-alcoholic steatohepatitis (NASH) is the most aggressive form of NAFLD, and is a condition in which excessive fat accumulation (steatosis) is accompanied by inflammation of the liver. If advanced, NASH can lead to the development of scar tissue in the liver (fibrosis) and, eventually, cirrhosis. As described above, the compounds of the invention have been found to be useful in the treatment or prevention of NAFLD, particularly when accompanied by inflammation of the liver. It follows that the compounds of the invention are also useful in the treatment or prevention of NASH. Therefore, in a further embodiment of the first aspect of the invention, the treatment or prevention is of non-alcoholic steatohepatitis (NASH).

The skilled person will understand that treatment with compounds of the first aspect of the invention may further comprise (i.e. be combined with) further (i.e. additional/other) treatment(s) for the same condition. In particular, treatment with compounds of the invention may be combined with other means for the treatment of a fatty liver disease, as described herein, such as treatment with one or more other therapeutic agent that is useful in the treatment of a fatty liver disease as known to those skilled in the art; for example, therapies comprising requiring the patient to undergo a change of diet and/or undertake exercise regiments, and/or surgical procedures designed to promote weight loss (such as gastric band surgery).

In particular, treatment with compounds of the invention may be performed in combination with (e.g. in a patient who is also being treated with) one or more (e.g. one) additional compounds (i.e. therapeutic agents) that are capable of reducing the level of fat (e.g. triglycerides) in the liver.

References to treatment of a fatty liver disease may refer to achieving a therapeutically significant reduction of fat (e.g. triglycerides levels) in liver cells (such as a reduction of at least 5% by weight, e.g. a reduction of at least 10%, or at least 20% or even 25%).

Pharmaceutical Compositions

As described herein, compounds of the first aspect of the invention are useful as pharmaceuticals. Such compounds may be administered alone or may be administered byway of known pharmaceutical compositions/formulations.

In a fourth aspect of the invention, there is provided a pharmaceutical composition comprising a compound as defined in the first aspect of the invention (i.e. a compound of the invention), and optionally one or more pharmaceutically acceptable adjuvant, diluent and/or carrier.

The skilled person will understand that references herein to compounds of the first aspect of the invention being for particular uses (and, similarly, to uses and methods of use relating to compounds of the invention) may also apply to pharmaceutical compositions comprising compounds of the invention as described herein.

In a fifth aspect of the invention, there is provided a pharmaceutical composition for use in the treatment of hyperglycaemia or a disorder characterized by hyperglycaemia (as defined herein, such as type 2 diabetes) comprising a compound as defined in the first aspect of the invention, and optionally one or more pharmaceutically acceptable adjuvant, diluent and/or carrier.

In an alternative fifth aspect of the invention, there is provided a pharmaceutical composition for use in the treatment or prevention of a non-alcoholic fatty liver disease, as defined herein.

The skilled person will understand that compounds of the first (and, therefore, second and third) aspect of the invention may act systemically and/or locally (i.e. at a particular site).

The skilled person will understand that compounds and compositions as described in the first to fifth aspects of the invention will normally be administered orally, intravenously, subcutaneously, buccally, rectally, dermally, nasally, tracheally, bronchially, sublingually, intranasally, topically, by any other parenteral route or via inhalation, in a pharmaceutically acceptable dosage form. Pharmaceutical compositions as described herein will include compositions in the form of tablets, capsules or elixirs for oral administration, suppositories for rectal administration, sterile solutions or suspensions for parenteral or intramuscular administration, and the like. Alternatively, particularly where such compounds of the invention act locally, pharmaceutical compositions may be formulated for topical administration.

Thus, in particular embodiments of the fourth and fifth aspects of the invention, the pharmaceutical formulation is provided in a pharmaceutically acceptable dosage form, including tablets or capsules, liquid forms to be taken orally or by injection, suppositories, creams, gels, foams, inhalants (e.g. to be applied intranasally), or forms suitable for topical administration. For the avoidance of doubt, in such embodiments, compounds of the invention may be present as a solid (e.g. a solid dispersion), liquid (e.g. in solution) or in other forms, such as in the form of micelles.

For example, in the preparation of pharmaceutical formulations for oral administration, the compound may be mixed with solid, powdered ingredients such as lactose, saccharose, sorbitol, mannitol, starch, amylopectin, cellulose derivatives, gelatin, or another suitable ingredient, as well as with disintegrating agents and lubricating agents such as magnesium stearate, calcium stearate, sodium stearyl fumarate and polyethylene glycol waxes. The mixture may then be processed into granules or compressed into tablets.

Soft gelatin capsules may be prepared with capsules containing one or more active compounds (e.g. compounds of the first and, therefore, second and third aspects of the invention, and optionally additional therapeutic agents), together with, for example, vegetable oil, fat, or other suitable vehicle for soft gelatin capsules. Similarly, hard gelatine capsules may contain such compound(s) in combination with solid powdered ingredients such as lactose, saccharose, sorbitol, mannitol, potato starch, corn starch, amylopectin, cellulose derivatives or gelatin.

Dosage units for rectal administration may be prepared (i) in the form of suppositories which contain the compound(s) mixed with a neutral fat base; (ii) in the form of a gelatin rectal capsule which contains the active substance in a mixture with a vegetable oil, paraffin oil, or other suitable vehicle for gelatin rectal capsules; (iii) in the form of a ready-made micro enema; or (iv) in the form of a dry micro enema formulation to be reconstituted in a suitable solvent just prior to administration.

Liquid preparations for oral administration may be prepared in the form of syrups or suspensions, e.g. solutions or suspensions, containing the compound(s) and the remainder of the formulation consisting of sugar or sugar alcohols, and a mixture of ethanol, water, glycerol, propylene glycol and polyethylene glycol. If desired, such liquid preparations may contain colouring agents, flavouring agents, saccharine and carboxymethyl cellulose or other thickening agent. Liquid preparations for oral administration may also be prepared in the form of a dry powder to be reconstituted with a suitable solvent prior to use.

Solutions for parenteral administration may be prepared as a solution of the compound(s) in a pharmaceutically acceptable solvent. These solutions may also contain stabilizing ingredients and/or buffering ingredients and are dispensed into unit doses in the form of ampoules or vials. Solutions for parenteral administration may also be prepared as a dry preparation to be reconstituted with a suitable solvent extemporaneously before use.

The skilled person will understand that compounds of the invention, and pharmaceutically-acceptable salts thereof, may be administered (for example, as formulations as described hereinabove) at varying doses, with suitable doses being readily determined by one of skill in the art. Oral, pulmonary and topical dosages (and subcutaneous dosages, although these dosages may be relatively lower) may range from between about 0.01 µg/kg of body weight per day (µg/kg/day) to about 200 µg/kg/day, preferably about 0.01 to about 10 µg/kg/day, and more preferably about 0.1 to about 5.0 µg/kg/day. For example, when administered orally, treatment with such compounds may comprise administration of a formulations typically containing between about 0.01 µg to about 2000 mg, for example between about 0.1 µg to about 500 mg, or between 1 µg to about 100 mg (e.g. about 20 µg to about 80 mg), of the active ingredient(s). When administered intravenously, the most preferred doses will range from about 0.001 to about 10 µg/kg/hour during constant rate infusion. Advantageously, treatment may comprise administration of such compounds and compositions in a single daily dose, or the total daily dosage may be administered in divided doses of two, three or four times daily (e.g. twice daily with reference to the doses described herein, such as a dose of 10 mg, 20 mg, 30 mg or 40 mg twice daily, or 10 µg, 20 µg, 30 µg or 40 µg twice daily).

In any event, the skilled person (e.g. the physician) will be able to determine the actual dosage which will be most suitable for an individual patient, which is likely to vary with the route of administration, the type and severity of the condition that is to be treated, as well as the species, age, weight, sex, renal function, hepatic function and response of the particular patient to be treated. The above-mentioned dosages are exemplary of the average case; there can, of course, be individual instances where higher or lower dosage ranges are merited, and such are within the scope of this invention.

As described herein above, the skilled person will understand that treatment with compounds of the first aspect of the invention may further comprise (i.e. be combined with) further (i.e. additional/other) treatment(s) for the same condition. In particular, treatment with compounds of the invention may be combined with other means for the treatment of hyperglycaemia or a disorder characterized by hyperglycaemia (as defined herein, such as type 2 diabetes), such as treatment with one or more other therapeutic agent that is useful in the treatment of hyperglycaemia or a disorder characterized by hyperglycaemia (as defined herein, such as type 2 diabetes).

In particular embodiments of the fourth and fifth aspects of the invention, the pharmaceutical composition may further comprise one or more additional (i.e. other) therapeutic agent.

In more particular embodiments, the one or more additional therapeutic agent is an agent for the treatment of type 2 diabetes as known to those skilled in the art, such as metformin, sulfonylureas (e.g. carbutamide, acetohexamide, chlorpropamide, tolbutamide. glipizide (glucotrol), gliclazide, glibenclamide, glyburide (Micronase), glibornuride, gliquidone, glisoxepide, glyclopyramide, glimepiride (Amaryl), glimiprime, JB253 or JB558), thiazolidinediones (e.g. pioglitazone, rosiglitazone (Avandia), lobeglitazone (Duvie) and troglitazone (Rezulin)), dipeptidyl peptidase-4 inhibitors (e.g. sitagliptin, vildagliptin, saxagliptin, linagliptin, anagliptin, teneligliptin, alogliptin, trelagliptin, gemigliptin, dutogliptin and omarigliptin), SGLT2 inhibitors (e.g. dapagliflozin, empagliflozin, canagliflozin, ipragliflozin, tofogliflozin, sergliflozin etabonate, remogliflozin etabonate, and ertugliflozin), and glucagon-like peptide-1 (GLP-1) analogues.

The skilled person will understand that combinations of therapeutic agents may also described as a combination product and/or provided as a kit-of-parts.

In a sixth aspect of the invention, there is provided a combination product comprising:
(A) a compound as defined in the first aspect of the invention; and
(B) one or more additional therapeutic agent,
wherein each of components (A) and (B) is formulated in admixture, optionally with one or more a pharmaceutically-acceptable adjuvant, diluent or carrier.

In a seventh aspect of the invention, there is provided a kit-of-parts comprising:
(a) a compound as defined in the first (or second and/or third) aspect of the invention, (or a pharmaceutical composition comprising the same) or a pharmaceutical composition as defined in the fourth or fifth aspect of the invention; and
(b) one or more other therapeutic agent, optionally in admixture with one or more pharmaceutically-acceptable adjuvant, diluent or carrier,
which components (a) and (b) are each provided in a form that is suitable for administration in conjunction with the other.

In particular embodiments (e.g. of the sixth and seventh aspects of the invention), the additional therapeutic agent is a therapeutic agent that is useful for the treatment of hyperglycaemia or a disorder characterized by hyperglycaemia (e.g. type 2 diabetes), as known to those skilled in the art (such as those described herein).

For example, in particular embodiments of the fourth to fifth aspects of the invention, the additional therapeutic agent is an agent that:
(i) is capable of reducing blood sugar levels; and/or
(ii) is an insulin sensitizer; and/or
(iii) is able to enhance insulin release,
which agents will be readily identified by those skilled in the art and include, in particular, such therapeutic agents that are commercially available (e.g. agents that the subject of a marketing authorization in one or more territory, such as a European or US marketing authorization).

The skilled person will understand that references to therapeutic agents capable of reducing blood glucose levels may refer to compounds capable of reducing levels of blood by at least 10% (such as at least 20%, at least 30% or at least 40%, for example at least 50%, at least 60%, at least 70% or at least 80%, e.g. at least 90%) when compared to the blood glucose levels prior to treatment with the relevant compound.

In alternative embodiments of the sixth and seventh aspects of the invention, the additional therapeutic agent is an agent for the treatment or prevention of a non-alcoholic fatty liver disease (such as NASH), which agents will be readily identified by those skilled in the art and include, in particular, such therapeutic agents that are commercially available (e.g. agents that the subject of a marketing authorization in one or more territory, such as a European or US marketing authorization).

Preparation of Compounds/Compositions

Pharmaceutical compositions/formulations, combination products and kits as described herein may be prepared in accordance with standard and/or accepted pharmaceutical practice.

Thus, in a further aspect of the invention there is provided a process for the preparation of a pharmaceutical composition/formulation, as hereinbefore defined, which process comprises bringing into association a compound of the invention, as hereinbefore defined, with one or more pharmaceutically-acceptable adjuvant, diluent or carrier.

In further aspects of the invention, there is provided a process for the preparation of a combination product or kit-of-parts as hereinbefore defined, which process comprises bringing into association a compound of the invention, as hereinbefore defined, or a pharmaceutically acceptable salt thereof with the other therapeutic agent that is useful in the treatment of hyperglycaemia or a disorder characterized by hyperglycaemia (e.g. type 2 diabetes), and at least one pharmaceutically-acceptable adjuvant, diluent or carrier.

As used herein, references to bringing into association will mean that the two components are rendered suitable for administration in conjunction with each other.

Thus, in relation to the process for the preparation of a kit of parts as hereinbefore defined, by bringing the two components "into association with" each other, we include that the two components of the kit of parts may be:
(i) provided as separate formulations (i.e. independently of one another), which are subsequently brought together for use in conjunction with each other in combination therapy; or
(ii) packaged and presented together as separate components of a "combination pack" for use in conjunction with each other in combination therapy.

Compounds as defined in the first (and, therefore, second and third) aspect of the invention (i.e. compounds of the invention) may be prepared in accordance with techniques that are well known to those skilled in the art, such as those described in the examples provided hereinafter.

For example, there is provided a process for the preparation of a compound of formula I, or a pharmaceutically acceptable salt thereof, as defined in the first aspect of the invention (which may be utilised in the preparation of, for example, a compound as defined in the second aspect of the invention), which process comprises:
(i) reaction of a compound of formula II

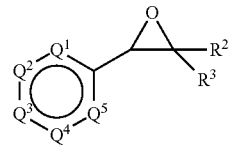

(II)

wherein $Q^1$ to $Q^5$ (and, therefore, ring Q), $R^2$ and $R^3$ are as defined hereinabove, with a compound of formula III $$H_2N-R^1 \quad \text{(III)}$$

wherein $R^1$ is as defined hereinabove, optionally in the presence of a suitable solvent known to those skilled in the art;

(iia) reaction of a compound of formula IV

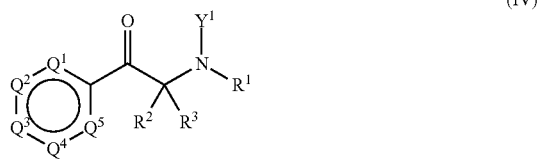

wherein $Q^1$ to $Q^5$, $R^1$, $R^2$ and $R^3$ are as defined hereinabove and $Y^1$ represents H or $PG^1$, wherein $PG^1$ is a suitable protecting group as known to those skilled in the art (e.g. —C(O)OtBu or —SO$_2$CH$_3$), with a suitable reduction agent as known to those skilled in the art (such as NaBH$_4$ or LiAlH$_4$) or by hydrogenation in the presence of a suitable catalyst;

(iib) for compounds of formula IA, reaction of a compound of formula IV as defined herein above but wherein $Y^1$ represents $PG^2$ wherein $PG^2$ is a suitable protecting group as known to those skilled in the art (e.g. —C(O)OtBu) in the presence of a suitable catalyst (such as a complex between (1S, 2S)-(+)—N-(4-toluenesulphonyl)-1,2-diphenylethylene diamine and [Ru(cymene)Cl$_2$]$_2$)) and in the presence of hydrogen or a suitable hydrogen donor (such as formic acid) and optionally in the presence of a base (e.g. Et$_3$N) and in the presence of a suitable solvent (such as CH$_2$Cl$_2$);

(iii) for compounds wherein at least one $X^2$ is present and represents —OH, deprotection of a compound wherein the corresponding —OH group is represented by —OPG$^2$, wherein PG$^2$ represents a suitable protecting group as known to those skilled in the art (e.g. benzyl or alkyl, such as methyl), under conditions known to those skilled in the art (for example: in the case of benzyl, in the presence of hydrogen and a suitable catalyst or a suitable acid; in the case of alkyl, such as methyl, in the presence of BBr$_3$, HBr or alkyl sulfides);

(iv) for compounds wherein at least one $X^2$ is present and represents —NH$_2$, deprotection of a compound wherein the corresponding —NH$_2$ group is represented by —NHPG$^3$ or —N(PG$^3$)$_2$, wherein PG$^3$ represents a suitable protecting group as known to those skilled in the art (e.g. carbamate protecting groups (such as tert-butyloxycarbonyl (Boc), fluorenylmethyloxycarbonyl (Fmoc) and carboxybenzyl (Cbz) and amide protecting groups (such as acetyl and benzoyl)), under conditions known to those skilled in the art (for example in the case of Boc, in the presence of a suitable acid (e.g. trifluoroacetic acid or HCl). If more than one PG$^2$ is present, each PG$^2$ may each represent the same protecting group, and therefore may be deprotected under a single set of conditions;

(v) for compounds wherein at least one $X^2$ is present and represents —NH$_2$, reduction of a compound wherein the corresponding group is represented by —NO$_2$, under conditions known to those skilled in the art (for example, by hydrogenation, such as hydrogenation using hydrogen gas and a suitable catalyst as known to those skilled in the art, (e.g. Pd—C, PtO$_2$, Raney-Nickel), Fe or Zn in acidic media (e.g. AcOH), borohydrides together with a suitable catalyst (e.g. NaBH$_4$ and Raney-Nickel), or agents such as SnCl$_2$, TiCl$_3$, SmI$_2$, and the like).

Those skilled in the art will understand that certain functional groups, such as the essential —OH and/or the —NHR$^1$ groups) may need to be protected (and deprotected) one or more times during the reaction, which protections (and deprotections) may be performed using techniques known to those skilled in the art.

Compounds of formulae II, III and IV are either commercially available, are known in the literature, or may be obtained either by analogy with the processes described herein, or by conventional synthetic procedures, in accordance with standard techniques, from available starting materials (e.g. appropriately substituted benzaldehydes, styrenes or phenacyl bromides (or phenacylchloride, and the like) using appropriate reagents and reaction conditions. In this respect, the skilled person may refer to inter alia "*Comprehensive Organic Synthesis*" by B. M. Trost and I. Fleming, Pergamon Press, 1991. Further references that may be employed include "*Science of Synthesis*", Volumes 9-17 (Hetarenes and Related Ring Systems), Georg Thieme Verlag, 2006.

The substituents $X^1$, $X^2$, $R^1$, $R^2$ and $R^3$, as hereinbefore defined, may be modified one or more times, after or during the processes described above for preparation of compounds of formula I by way of methods that are well known to those skilled in the art. Examples of such methods include substitutions, reductions, oxidations, dehydrogenations, alkylations, dealkylations, acylations, hydrolyses, esterifications, etherifications, halogenations and nitrations. The precursor groups can be changed to a different such group, or to the groups defined in formula I, at any time during the reaction sequence. The skilled person may also refer to "*Comprehensive Organic Functional Group Transformations*" by A. R. Katritzky, O. Meth-Cohn and C. W. Rees, Pergamon Press, 1995 and/or "*Comprehensive Organic Transformations*" by R. C. Larock, Wiley-VCH, 1999.

Such compounds may be isolated from their reaction mixtures and, if necessary, purified using conventional techniques as known to those skilled in the art. Thus, processes for preparation of compounds of the invention as described herein may include, as a final step, isolation and optionally purification of the compound of the invention (e.g. isolation and optionally purification of the compound of formula).

The skilled person will understand that compounds of formula I having specific stereochemistry (such as compounds of formula IA) may be provided by reacting suitable starting materials having the required stereochemistry in processes as described herein.

For example, compounds of formula IA may be provided by reacting compounds having the required stereochemistry in processes as described in step (i) or steps (iii) to (v) in the processes described herein above.

Further, the skilled person will understand that suitable starting materials having the required stereochemistry (such as suitable compounds of formula II and V wherein the carbon substituted with the essential oxygen is, for example, the (R) configuration, as required as necessary for the preparation of compounds of formula IA) may be prepared by analogy with the process described in step (iib) herein above.

It will be appreciated by those skilled in the art that, in the processes described above and hereinafter, the functional groups of intermediate compounds may need to be protected by protecting groups. The protection and deprotection of functional groups may take place before or after a reaction in the above-mentioned schemes.

Protecting groups may be applied and removed in accordance with techniques that are well known to those skilled in the art and as described hereinafter. For example, protected compounds/intermediates described herein may be converted chemically to unprotected compounds using standard deprotection techniques. The type of chemistry involved will dictate the need, and type, of protecting groups as well as the sequence for accomplishing the synthesis. The use of protecting groups is fully described in "*Protective Groups in Organic Synthesis*", 3rd edition, T. W. Greene & P. G. M. Wutz, Wiley-Interscience (1999).

Compounds as described herein (in particular, compounds as defined in the first and, therefore, second and third aspects of the invention) may have the advantage that they may be more efficacious than, be less toxic than, be longer acting than, be more potent than, produce fewer side effects than, be more easily absorbed than, and/or have a better pharmacokinetic profile (e.g. higher oral bioavailability and/or lower clearance) than, and/or have other useful pharmacological, physical, or chemical properties over, compounds known in the prior art, whether for use in the above-stated indications or otherwise. In particular, such compounds may have the advantage that they are more efficacious and/or exhibit advantageous properties in vivo.

Without wishing to be bound by theory, compounds as described herein are thought to be potent agonists of the $\beta_2$-adrenergic receptor, which allows for increased glucose uptake in skeletal muscle cells.

In addition, compounds as described herein are thought to be agonists of the $\beta_2$-adrenergic receptor without (or with only a minimal effect in) inducing cAMP production. It is thought that this allows for the increased glucose uptake in skeletal muscle cells with lower levels of side effects than would result from other treatments. Further, combining compounds as described herein with therapeutic agents that are able to decrease blood glucose levels is thought to provide an effective combination therapy.

EXAMPLES

The present invention is illustrated by way of the following examples.

Chemicals and reagents were obtained from commercial suppliers and were used as received unless otherwise stated. All reactions involving moisture sensitive reagents were performed in oven or flame dried glassware under a positive pressure of nitrogen or argon.

Abbreviations

Abbreviations as used herein will be known to those skilled in the art. In particular, the following abbreviations may be used herein.
AcOH acetic acid
aq aqueous
atm atmosphere
Boc$_2$O di-tert-butyldicarbonate
DIPEA N,N-diisopropylethylamine
DMAP 4-dimethylaminopyridine
DMF dimethylformamide
DMSO dimethylsulfoxide
eq equivalent
EtOAc ethyl acetate
EtOH ethanol
HPLC high-performance liquid chromatography
MeCN acetonitrile
MeOH methanol
MTBE methyl tert-butyl ether
Pd—C palladium on carbon
rt room temperature
sat saturated
TFA trifluoroacetic acid
THF tetrahydrofuran Example Compounds In the event that there is a discrepancy between nomenclature and the structure of compounds as depicted graphically, it is the latter that presides (unless contradicted by any experimental details that may be given and/or unless it is clear from the context).

Example 1: (S)-1-(2-Aminothiazol-4-yl)-2-(butylamino)ethan-1-ol hydrochloride

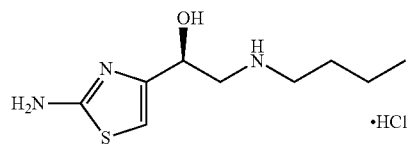

(a) 1-(2-Aminothiazol-4-yl)-2-bromoethan-1-one

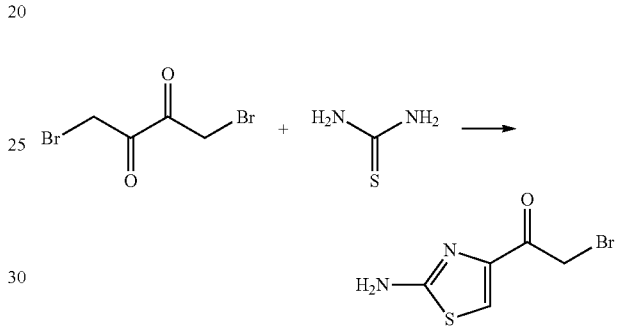

A solution of thiourea (1.4 g, 18.4 mmol) in EtOH (60 mL) was added dropwise to a solution of 1,4-dibromo-2,3-dione in EtOH (60 mL) at reflux. The mixture was heated at reflux for 30 min and allowed to cool to rt. The mixture was filtered, concentrated and the residue treated with EtOH (20 mL). The solid material was collected to give a first crop of the sub-title compound. A second crop was obtained by adding EtOAc (100 mL) to the filtrate and collecting the precipitate. The total yield was (1.28 g, 5.79 mmol, 32%) and the material was used in the next step without further purification.

(b) N-(4-(2-Bromoacetyl)thiazol-2-yl)isobutyramide

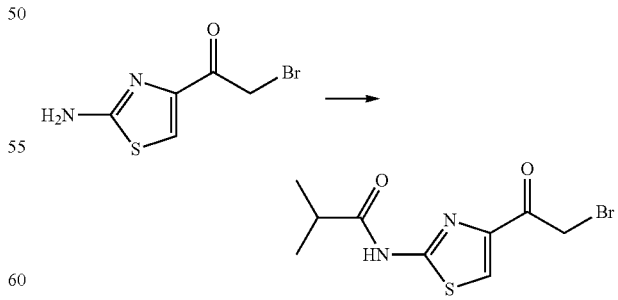

A mixture of 1-(2-aminothiazol-4-yl)-2-bromoethan-1-one (250 mg; 1.13 mmol) and isobutyric anhydride (0.56 mL, 3.40 mmol) was heated at 90° C. for 19 h. The mixture was allowed to cool to rt and stirred with EtOAc for 10 min and the solids were collected. The filtrate was concentrated

(c) tert-Butylbutyl(2-(2-isobutyramidothiazol-4-yl)-2-oxoethyl)carbamate

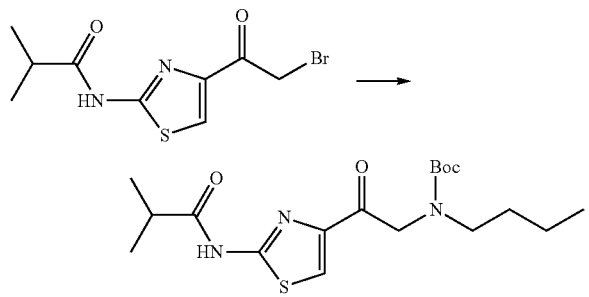

A solution of N-(4-(2-bromoacetyl)thiazol-2-yl)isobutyramide (960 mg, 3.30 mmol) in CH$_2$Cl$_2$ (15 mL) was added dropwise to a mixture of n-butylamine (0.65 mL, 6.60 mmol), DIPEA (0.57 mL, 3.30 mmol) and CH$_2$Cl$_2$ (8 mL) at ° C. The cooling bath was removed and the mixture was stirred at rt for 1 h. A solution of Boc$_2$O (2.27 mL, 9.90 mmol) in CH$_2$Cl$_2$ (5 mL) was added and the mixture was stirred at rt for 30 min. The mixture was diluted with CH$_2$Cl$_2$, washed with H$_2$O, brine, dried over Na$_2$SO$_4$ and concentrated. The residue was purified by chromatography to give the sub-title compound (690 mg, 1.80 mmol, 55%).

(d) tert-Butyl(S)-butyl(2-hydroxy-2-(2-isobutyramidothiazol-4-yl)ethyl)carbamate

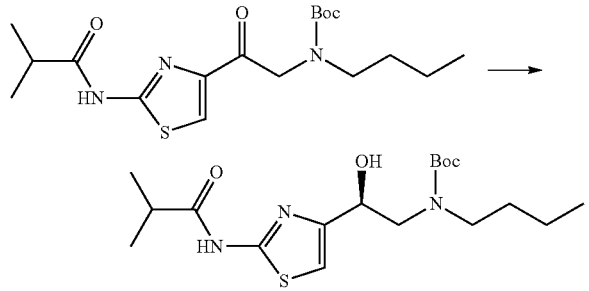

Formic acid/Et$_3$N (5:2, 1 mL) followed by (S,S)—N-(p-toluenesulfonyl)-1,2-diphenylethane-diamine(chloro)(p-cymene)ruthenium(II) (10 mg, 0.016 mmol) were added to a solution of tert-butyl butyl(2-(2-isobutyramidothiazol-4-yl)-2-oxoethyl)carbamate (120 mg, 0.31 mmol) in DMF (4 mL) at rt. The mixture was stirred at rt under ambient atmosphere for 23 h and diluted with CH$_2$Cl$_2$. It was washed with H$_2$O, brine, dried over Na$_2$SO$_4$ and concentrated. The residue was purified by chromatography to give the sub-title compound (90 mg, 0.23 mmol, 75%).

(e) (S)-1-(2-Aminothiazol-4-yl)-2-(butylamino)ethan-1-ol

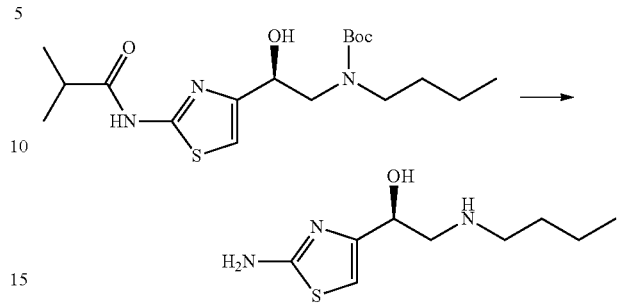

HCl (aq, 6 M, 3 mL) was added to a solution of tert-butyl (S)-butyl(2-hydroxy-2-(2-iso-butyramidothiazol-4-yl)ethyl)carbamate (420 mg, 1.09 mmol) in EtOH (3 mL). The mixture was heated in a microwave reactor at 85° C. for 4 h, allowed to cool and concentrated. The residue was purified by reverse phase chromatography to give the title compound (180 mg, 0.62 mmol, 57%).

$^1$H NMR (400 MHz, D$_2$O): δ 6.82 (d, J=1.0 Hz, 1H), 5.05 (ddd, J=9.6, 3.7, 1.0 Hz, 1H), 3.43 (dd, J=13.0, 3.6 Hz, 1H), 3.35 (dd, J=13.0, 9.6 Hz, 1H), 3.20-3.08 (m, 2H), 1.71 (tt, J=7.9, 6.5 Hz, 2H), 1.40 (hept, J=7.6 Hz, 2H), 0.94 (t, J=7.4 Hz, 3H).

Example 2: (S)-2-(Butylamino)-1-(2-(trifluoromethyl)thiazol-4-yl)ethan-1-ol hydrochloride

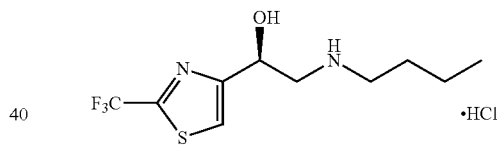

(a) Trifluorothioacetamide

A mixture of Trifluoroacetamide (1.2 g, 10.6 mmol), Lawesson's reagent (2.36 g, 5.84 mmol) and THF (10 mL) was heated at reflux for 2 h. The mixture was concentrated and purified by chromatography to give the sub-title compound (0.89 g, 6.9 mmol, 65%).

(b) 2-Bromo-1-(2-(trifluoromethyl)thiazol-4-yl)ethan-1-one

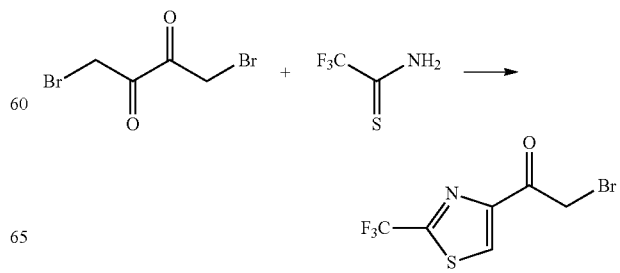

A solution of trifluorothioacetamide (0.89 g, 6.9 mmol) in MeCN (13 mL) was added dropwise to a solution of 1,4-dibromo-2,3-dione in MeCN (13 mL) at 60° C. over 1 h. The mixture was heated at 60° C. for 90 min, allowed to cool to rt and concentrated. The residue was purified by chromatography to give the sub-title compound (712 mg, 2.6 mmol, 38%).

(c) (R)-2-Bromo-1-(2-(trifluoromethyl)thiazol-4-yl)ethan-1-ol

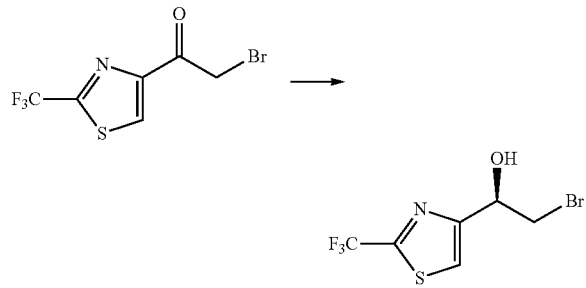

Borane (1 M in THF, 0.58 mL, 0.58 mmol) was added dropwise to a mixture of (R)-2-methyl-CBS-oxazaborolidine (1M in toluene, 0.07 mL, 0.07 mmol) and THF (0.2 mL) at rt. The mixture was stirred 15 min at rt and a solution of 2-bromo-1-(2-(trifluoromethyl)thiazol-4-yl)ethan-1-one (200 mg, 0.73 mmol) in THF (0.8 mL) was added dropwise (0.09 mL/min). After 90 min at rt, MeOH (2 mL) was added. The mixture was stirred for 30 min and carefully concentrated. The residue was treated with $CH_2Cl_2$ and the mixture was washed with $KH_2PO_4$ (0.5 M), $H_2O$ and dried over $Na_2SO_4$. The solvents were carefully removed to give the sub-title compound (190 mg, 0.68 mmol, 94%).

(d) (R)-4-(Oxiran-2-yl)-2-(trifluoromethyl)thiazole

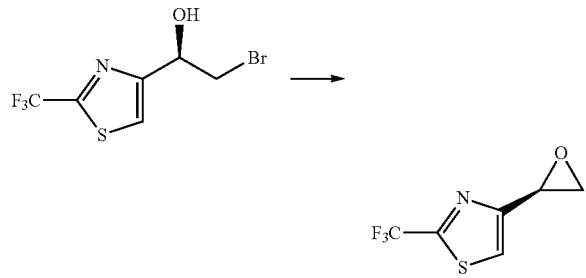

$K_2CO_3$ (36 mg, 0.26 mol) was added to a mixture of ((R)-2-bromo-1-(2-(trifluoromethyl)-thiazol-4-yl)ethan-1-ol (48 mg, 0.17 mmol) in MeOH (1.8 mL) at rt. The mixture was stirred for 30 min, filtered and concentrated. The residue was extracted with $CH_2Cl_2$ and the combined extracts were filtered and concentrated to give the sub-title compound (26 mg, 0.13 mmol, 72%).

(d) (S)-2-(Butylamino)-1-(2-(trifluoromethyl)thiazol-4-yl)ethan-1-ol hydrochloride

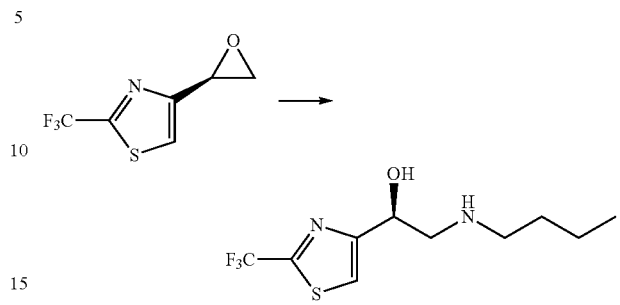

A mixture of (R)-4-(oxiran-2-yl)-2-(trifluoromethyl)thiazole (30 mg, 0.22 mmol) and n-butylamine (2.5 mL, 25.6 mmol) was heated at 60° C. in a sealed vial for 2 h, allowed to cool and concentrated. The residue was crystalized from MTBE/pentane. The solid was collected and dissolved in a small amount of MTBE. Pentane was added and the solution was kept in the freezer overnight. The solid formed was collected and purified by chiral HPLC to give the title compound (189 mg, 0.70 mmol, 55%. ee>99%).

$^1$H NMR (400 MHz, $CDCl_3$): δ 7.56 (d, J=1.0 Hz, 1H), 4.90 (ddd, J=1.0, 4.0, 7.7 Hz, 1H), 3.14 (dd, J=4.0, 12.3 Hz, 1H), 2.88 (dd, J=7.7, 12.3 Hz, 1H), 2.94 (br. s., 2H, overlapping), 2.71-2.57 (m, 2H), 1.51-1.41 (m, 2H), 1.40-1.28 (2H, m), 0.91 (t, J=7.3 Hz, 3H).

Example 3:5-(2-(Butylamino)-1-hydroxyethyl)pyridin-2(1H)-one

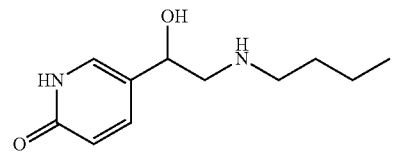

(a) 6-Benzyloxynicotinaldehyde

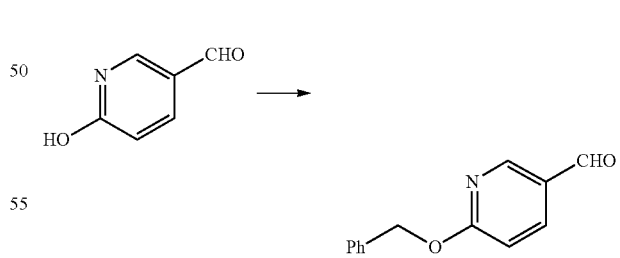

Benzyl bromide (500 mg, 2.92 mmol) was added to a mixture of 6-hydroxynicotinaldehyde (300 mg, 2.44 mmol), $Ag_2CO_3$ (1.0 g, 3.66 mmol) and MeCN (15 mL). The mixture was stirred at rt overnight, filtered and concentrated. The residue was partitioned between $H_2O$ and EtOAc and the organic layer was washed with $H_2O$, brine, dried over $MgSO_4$ and concentrated. The residue was purified by chromatography to give the sub-title compound (455 mg, 2.14 mmol, 88%).

(b) 2-(Benzyloxy)-5-(oxiran-2-yl)pyridine

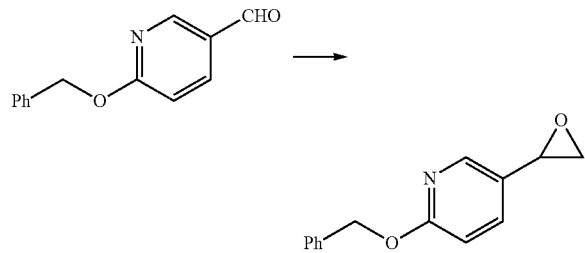

A solution trimethylsulfonium iodide (495 mg, 2.43 mg) in DMSO (7.5 mL) was added dropwise to a suspension of NaH (prepared from NaH, 101 mg, 2.53 mmol, 60% in mineral oil by washing with Et$_2$O) in THF (7.5 mL) at 0° C. The mixture was stirred at 0° C. for 30 min and a solution of 6-benzyloxynicotinaldehyde (450 mg, 2.11 mmol) in THF (3 mL) was added dropwise. The cooling bath was removed and the mixture was stirred at rt for 1 h and poured onto ice. The mixture was extracted with EtOAc and the combined extracts washed with H$_2$O, brine, dried over MgSO$_4$ and concentrated to give a quantitative yield of the sub-title compound that was used in the next step without further purification.

(c) 2-(Benzyl(butyl)amino)-1-(6-(benzyloxy)pyridin-3-yl)ethan-1-ol

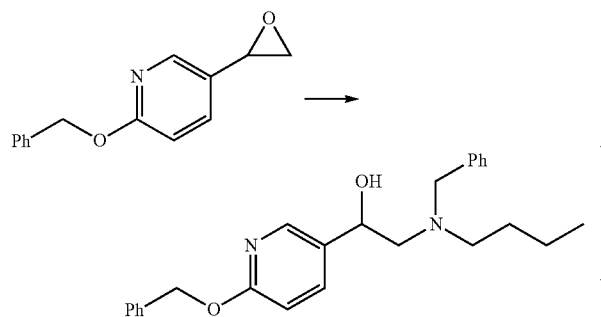

A mixture of 2-(benzyloxy)-5-(oxiran-2-yl)pyridine (200 mg, 0.88 mmol), n-butylamine (0.19 mL, 1.06 mmol) and iPrOH (0.5 mL) was heated in a microwave reactor at 100° C. for 90 min. The mixture was cooled, concentrated and purified by chromatography to give the sub-title compound (227 mg, 0.58 mmol, 66%).

(d) 5-(2-(Butylamino)-1-hydroxyethyl)pyridin-2(1H)-one

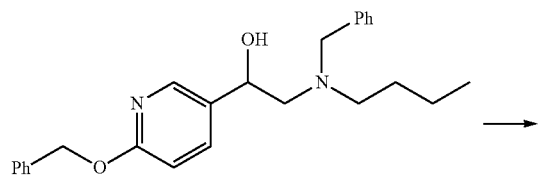

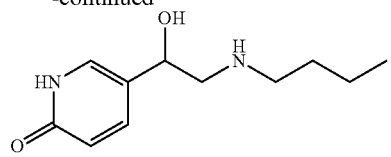

A mixture of 2-(benzyl(butyl)amino)-1-(6-(benzyloxy)pyridin-3-yl)ethan-1-ol (134 mg, 0.34 mg), Pd(OH)$_2$ (20% on carbon, 50% (w/w) aq suspension, 96 mg, 48 mg, 0.07 mmol) and cyclohexene (3.5 mL) was heated in a sealed vial at 85° C. for 2 h. Another portion of Pd(OH)$_2$ (20% on carbon, 50% (w/w) aq suspension, 96 mg, 48 mg, 0.07 mmol) was added and heating was continued for another 3 h. The mixture was cooled, filtered through Celite and concentrated. The residue was purified by chromatography to give the title compound (30 mg, 0.14 mmol, 42%).

Example 4: 4-(2-(Butylamino)-1-hydroxyethyl)pyridin-2(1H)-one acetate

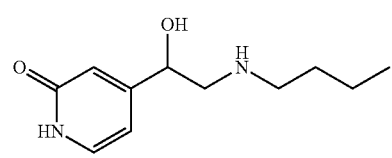

The title compound was obtained in accordance with the procedure in Example 3 from 2-hydroxypyridin-4-carbaldehyde.

$^1$H NMR (400 MHz, D$_2$O): δ 7.43 (dd, J=6.7, 0.7 Hz, 1H), 6.54-6.53 (m, 1H), 6.45 (ddd, J=6.9, 1.7, 0.5 Hz, 1H), 4.84 (dd, J=9.6, 3.2 Hz, 1H), 3.24 (dd, J=13.1, 3.2 Hz, 1H), 3.07 (dd, J=13.1, 9.6 Hz, 1H), 3.00-2.93 (m, 2H), 1.77 (s, 3H), 1.59-1.49 (m, 2H), 1.25 (dq, J=14.8, 7.4 Hz, 2H), 0.78 (t, J=7.4 Hz, 3H).

Example 5: (S)-1-(2-Aminopyrimidin-4-yl)-2-(butylamino)ethan-1-ol

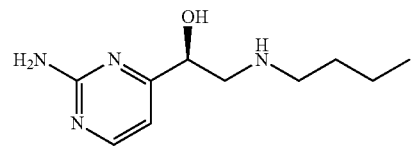

(a) 3,3-Dimethoxybutan-2-one

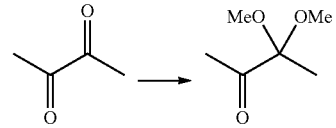

Diacetyl (26.3 mL, 300 mmol) was added dropwise to a solution of trimethylsilyl chloride (11.4 mL, 90 mmol) in MeOH (150 mL) at rt. The mixture was stirred at rt for 2 d and poured into a mixture of NaHCO₃ (aq, sat, 200 mL) and NaOH (aq, 2 M, 100 mL). The mixture was extracted with CH₂Cl₂ and the combined extracts dried over MgSO₄. Concentration and distillation (boiling point 44° C. at 20 mbar) gave the sub-title compound (23.0 g, 174 mmol, 58%).

(b) 1-(Dimethylamino)-4,4-dimethoxypent-1-en-3-one

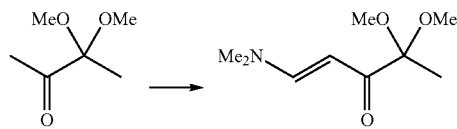

A mixture of 3,3-dimethoxybutan-2-one (23.0 g, 174 mmol) and dimethylformamide dimethylacetal (23 mL, 174 mmol) was heated at 160° C. for 16 h allowing ~5 mL of volatiles to distill off. Another portion of dimethylformamide dimethylacetal (5 mL) was added, the vessel was closed and the mixture heated at 160° C. for 3 h and cooled. The mixture was carefully concentrated and distilled (115° C., at −1 torr) to give the sub-title compound (25 g, 134 mmol, 77%).

(c) 4-(1,1-Dimethoxyethyl)pyrimidin-2-amine

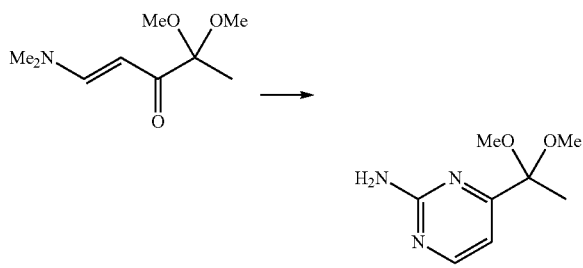

A mixture of 1-(dimethylamino)-4,4-dimethoxypent-1-en-3-one (1.0 g, 5.34 mmol), 1-acetylguanidine (0.54 g, 5.34 mmol) and EtOH (5 mL) was heated at 100° C. for 16 h. An additional portion of 1-acetylguanidine (0.54 g, 5.34 mmol) was added and the heating was continued for 4 h. The mixture was allowed to stand at rt overnight. The solids were collected, washed with cold EtOH and Et₂O and dried to give the sub-title compound (0.5 g, 2.73 mmol, 51%).

(d) N-(4-(1,1-Dimethoxyethyl)pyrimidin-2-yl)isobutyramide

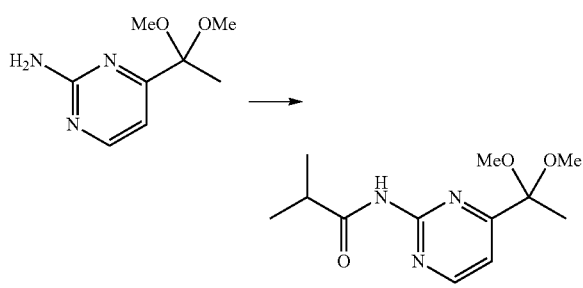

A mixture of 4-(1,1-dimethoxyethyl)pyrimidin-2-amine (100 mg, 0.55 mmol) and isobutyric anhydride (260 mg, 1.63 mmol) was heated in a sealed vial at 120° C. for 3 h and allowed to cool. Petroleum ether (3 mL) was added and the solution was kept at −20° C. for 1 h. The solids were collected, washed with petroleum ether and dried to give the sub-title compound (70 mg, 0.28 mmol, 51%).

(e) N-(4-(1-Methoxyvinyl)pyrimidin-2-yl)isobutyramide

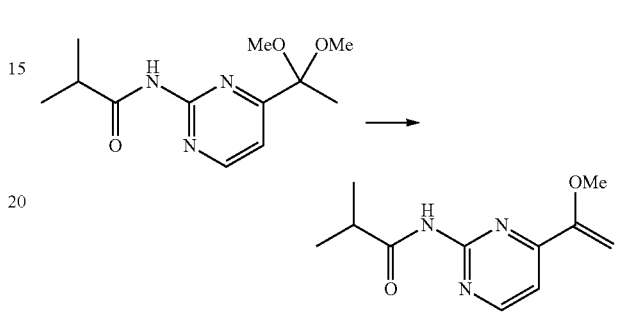

Trimethylsilyl trifluoromethanesulfonate (0.94 mL, 5.2 mmol) was added dropwise to a mixture of N-(4-(1,1-dimethoxyethyl)pyrimidin-2-yl)isobutyramide (600 mg, 2.4 mmol), DIPEA (1.0 mL, 5.9 mmol) and CH₂Cl₂ (4 mL) at 0° C. The mixture was stirred at rt for 1 d and concentrated. The residue was partitioned between H₂O and EtOAc and the organic layer was washed with H₂O, brine, dried over Na₂SO₄ and concentrated. The residue was dissolved in THF (4 mL) and H₂O (1 mL), and NH₄F (0.44 g, 11.8 mmol) was added. The mixture was heated at 100° C. for 30 min, diluted with EtOAc and washed with H₂O, brine, dried over Na₂SO₄ and concentrated. The residue was purified by chromatography to give the sub-title compound (400 mg, 1.8 mmol, 76%).

(f) N-(4-(2-Chloroacetyl)pyrimidin-2-yl)isobutyramide

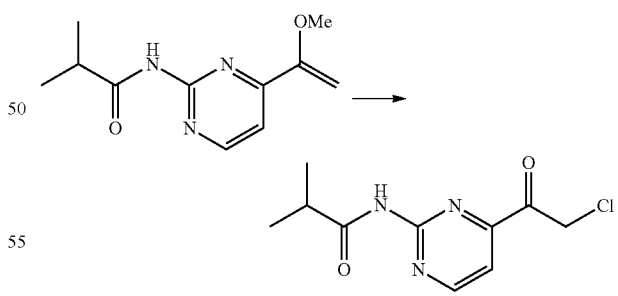

N-Bromosuccinimide (38.0 mg, 0.19 mmol) was added in portions to a mixture of N-(4-(1-methoxyvinyl)pyrimidin-2-yl)isobutyramide (43 mg, 0.19 mmol), THF (1 mL) and H₂O (0.25 mL) at 0° C. The mixture was allowed to come to rt over 1 h. NaCl (114 mg, 1.94 mmol) was added and the mixture was stirred at rt for 2 h and diluted with EtOAc. The mixture was washed with H₂O, brine, dried over MgSO₄ and concentrated. The residue was purified by chromatography to give the sub-title compound (45 mg, 0.18 mmol, 96%).

(g) (R)—N-(4-(2-Chloro-1-hydroxyethyl)pyrimidin-2-yl)isobutyramide

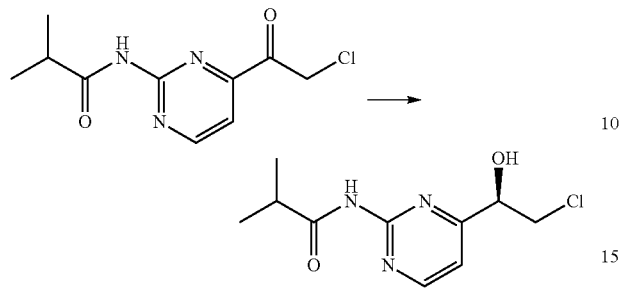

The sub-title compound was prepared from N-(4-(2-chloroacetyl)pyrimidin-2-yl)isobutyramide in accordance with the procedure in Example 1, Step (d).

(h) (R)—N-(4-(Oxiran-2-yl)pyrimidin-2-yl)isobutyramide

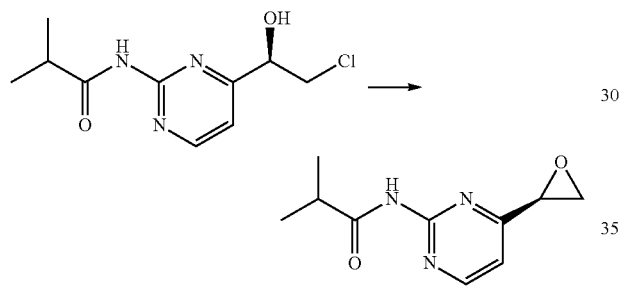

NaOH (aq, 4 M, 0.12 mL, 0.5 mmol) was added to a solution of (R)—N-(4-(2-chloro-1-hydroxyethyl)pyrimidin-2-yl)isobutyramide (12.0 mg, 0.05 mmol) in THF (1 mL). The mixture was stirred at rt for 30 min, diluted with EtOAc, washed with H₂O, brine, dried over Na₂SO₄ and concentrated to give the sub-title compound (10 mg, 0.048 mmol, 98%) which was used in the next step without any further purification.

(i) (S)-1-(2-Aminopyrimidin-4-yl)-2-(butylamino)ethan-1-ol

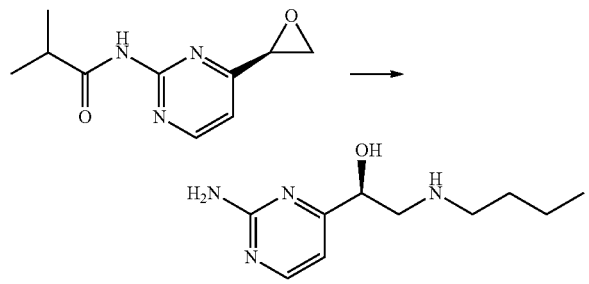

A mixture of (R)—N-(4-(oxiran-2-yl)pyrimidin-2-yl)isobutyramide (300 mg, 1.45 mmol) and n-butylamine (2.8 mL, 29 mmol) was heated in a microwave reactor at 100° C. for 2 h, allowed to cool and concentrated. The N-butyl isobutyramide that was formed in the reaction was removed by vacuum distillation (Kugelrohr, 125° C.). The residue was purified by chromatography to give the title compound (90 mg, 0.43 mmol, 30%).

¹H NMR (400 MHz, CD₃OD): δ 9.77 (d, J=5.2 Hz, 1H), 8.37 (dd, J=5.2, 0.6 Hz, 1H), 6.14 (ddd, J=8.6, 3.8, 0.6 Hz 1H), 4.49 (dd, J=12.3, 3.9 Hz, 1H), 4.29 (dd, J=12.3, 8.6 Hz, 1H), 4.25-4.11 (m, 2H), 3.12-3.03 (m, 2H), 3.00-2.87 (m, 2H), 2.50 (t, J=7.3 Hz, 3H).

Example 6: 2-(Butylamino)-1-(pyridin-4-yl)ethan-1-ol

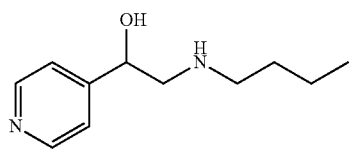

(a) 2-Bromo-1-(pyridin-4-yl)ethan-1-one hydrochloride

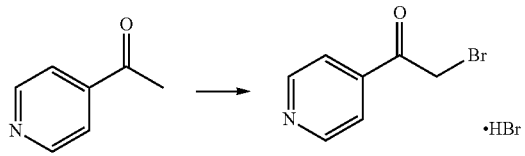

Bromine (0.23 mL, 4.54 mmol) in toluene (4 mL) was added dropwise to a mixture of 4-acetylpyridine (500 mg, 4.13 mmol), AcOH (2 mL) and toluene (8 mL) at 0° C. The mixture was stirred at rt overnight. The solid was collected, washed with Et₂O and dried to give the title compound (650 mg, 2.31 mmol, 56%).

(b) 2-(Butylamino)-1-(pyridin-4-yl)ethan-1-ol

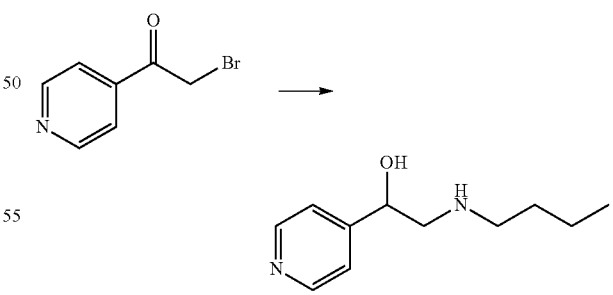

NaBH₄ (72.7 mg, 1.92 mmol) was added in portions to a mixture of 2-bromo-1-(pyridin-4-yl)ethan-1-one hydrochloride (150 mg, 0.53 mmol) and EtOH (2 mL) at 0° C. The mixture was stirred at rt for 2 h and filtered. n-Butylamine (0.13 mL, 1.33 mmol) was added to the filtrate and the mixture was heated at rx for 3 h, allowed to cool and concentrated. CHCl₃ (4 mL) was added to the residue, the solids were filtered of and the filtrate concentrated. The residue was purified by chromatography to give the title compound (20 mg, 0.10 mmol, 19%).

¹H NMR (400 MHz, CDCl₃): δ 8.55-8.53 (m, 2H), 7.30-7.28 (m, 2H), 4.68 (dd, J=8.8, 3.6 Hz, 1H), 2.93 (dd, J=12.0, 3.6 Hz, 1H), 2.71-2.58 (m, 3H), 1.50-1.29 (m, 4H), 0.91 (t, J=7.2 Hz, 3H).

Example 7: 2-(Butylamino)-1-(pyridin-3-yl)ethan-1-ol

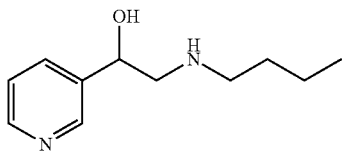

The title compound was prepared in accordance with Example 6 from 3-acetylpyridine.

¹H NMR (400 MHz, CDCl₃): δ 8.58 (d, J=1.9 Hz, 1H), 8.51 (dd, J=4.8, 1.6 Hz, 1H), 7.74-7.71 (m, 1H), 7.29-7.24 (m, 1H), 4.72 (dd, J=9.6, 3.6 Hz, 1H), 2.91 (dd, J=12.4, 3.6 Hz, 1H), 2.73-2.60 (m, 3H), 1.51-1.31 (m, 4H), 0.92 (t, J=7.2 Hz, 3H).

Example 8: (S)—N-(5-(2-(Butylamino)-1-hydroxyethyl)thiazol-2-yl)isobutyramide

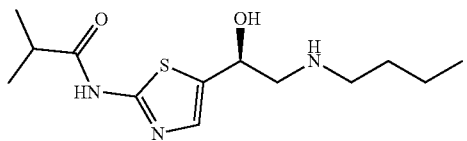

(a) 2-Isobutyramidothiazole-5-carboxylicacid

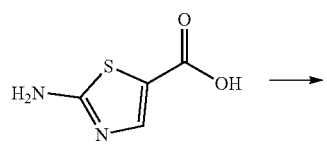

A mixture of 2-aminothiazole-5-carboxylic acid (600 mg, 4.16 mmol) and isobutyric acid (2.76 mL, 16.6 mmol) was heated at 100° C. overnight and allowed to cool. The solid was washed with Et₂O and the residue was used in the next step without further purification (847 mg, 3.95 mmol, 95%).

(b) N-(5-(2-Bromoacetyl)thiazol-2-yl)isobutyramide

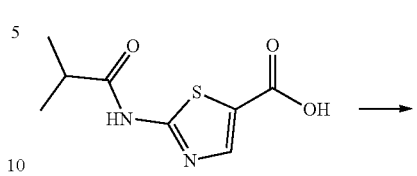

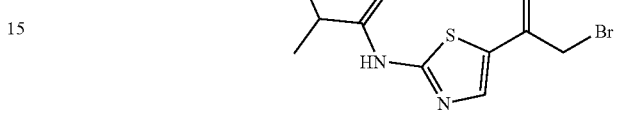

SOCl₂ (2.8 mL, 39.2 mmol) and a drop of DMF was added to a solution of 2-isobutyr-amidothiazole-5-carboxylic acid (1.20 g, 5.60 mmol) in CH₂Cl₂ (15 mL) at rt. The mixture was stirred at rt for 7 h. A drop of DMF was added and the mixture was concentrated. CH₂Cl₂ was added and the mixture concentrated. The procedure of adding CH₂Cl₂ followed by concentration was repeated twice. The residue was dried in vacuo, dissolved in CH₂Cl₂ and trimethylsilyl diazomethane (8.40 mL, 16.80 mmol) was added dropwise at 0° C. The mixture was allowed to come to rt over 10 h and cooled to 0° C. HBr (33% in AcOH, 1.28 mL, 22.4 mmol) was added dropwise at 0° C. The cooling bath was removed and the mixture was stirred rt for 1 h, diluted with CH₂Cl₂ and washed with NaHCO₃ (aq, sat), dried over MgSO₄ and concentrated. The residue was used in the next step without further purification (950 mg, 3.27 mmol, 58%).

(c) tert-Butyl butyl(2-(2-isobutyramidothiazol-5-yl)-2-oxoethyl)carbamate

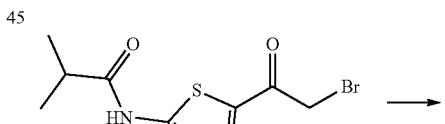

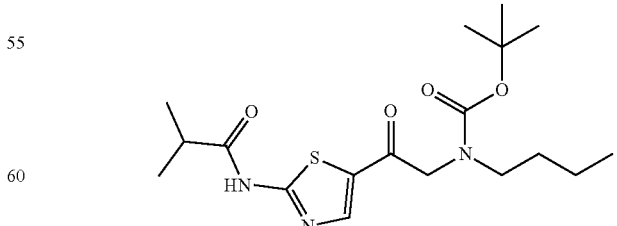

The sub-title compound was prepared from N-(4-(2-chloroacetyl)pyrimidin-2-yl)isobutyramide in accordance with the procedure in Example 1, Step (c).

(d) tert-Butyl (S)-butyl(2-hydroxy-2-(2-isobutyramidothiazol-5-yl)ethyl)carbamate

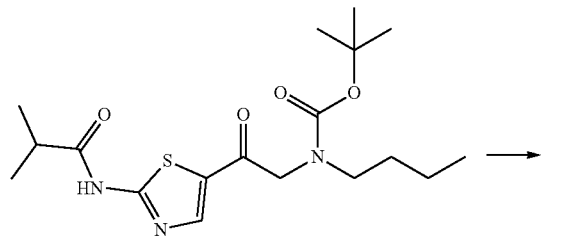

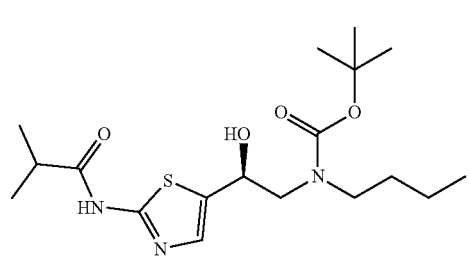

The sub-title compound was prepared from tert-butyl butyl(2-(2-isobutyramidothiazol-5-yl)-2-oxoethyl)carbamate in accordance with the procedure in Example 1, Step (d). The reaction time was 140 h. Yield 54%, ee=98%.

(e) (S)—N-(5-(2-(Butylamino)-1-hydroxyethyl)thiazol-2-yl)isobutyramide

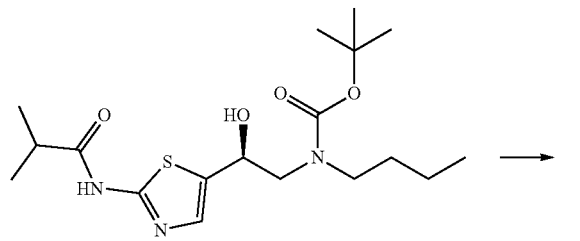

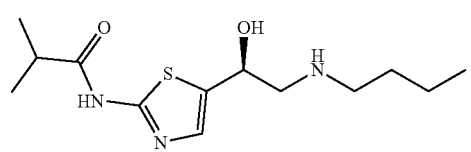 [SMILES: CCCCNC[C@H](O)c1cnc(NC(=O)C(C)C)s1]

The title compound was prepared from tert-butyl (S)-butyl(2-hydroxy-2-(2-isobutyramido-thiazol-5-yl)ethyl)carbamate in accordance with the procedure in Example 8.

$^1$H NMR (400 MHz, CD$_3$OD): δ 7.46 (d, J=0.9 Hz, 1H), 5.27 (ddd, J=9.2, 4.1, 0.7 Hz, 1H), 3.40-3.29 (m, 2H), 3.13-3.03 (m, 2H), 2.79 (hept, J=6.9 Hz, 1H), 1.72-1.64 (m, 2H), 1.39 (h, J=7.4 Hz, 2H), 1.19 (d, J=6.9 Hz, 6H), 0.93 (t, J=7.4 Hz, 3H).

Example 9: (S)-1-(2-Aminothiazol-5-yl)-2-(butylamino)ethan-1-ol dihydrochloride

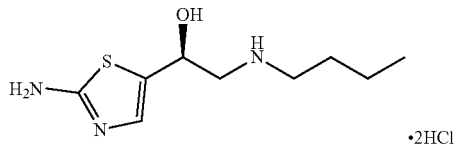

HCl (4 M in dioxane, 0.29 mL, 9.4 mmol) was added dropwise to a mixture of tert-butyl (S)-butyl(2-hydroxy-2-(2-isobutyramidothiazol-5-yl)ethyl)carbamate (195 mg, 0.47 mmol, see Example 8, Step (d)) in dioxane (0.5 mL) at rt. The mixture was stirred at rt for 24 h and concentrated. The residue was crystallized twice from MeCN/MeOH (10:1) to give the title compound (63 mg, 0.22 mmol, 47%).

$^1$H NMR (400 MHz, D$_2$O): δ 7.21 (d, J=0.8 Hz, 1H), 5.22 (ddd, J=9.6, 3.6, 0.8 Hz, 1H), 3.46-3.33 (m, 2H), 3.18-3.10 (m, 2H), 1.76-1.67 (m, 2H), 1.48-1.37 (m, 2H), 0.95 (t, J=7.6 Hz, 3H).

Example 10: (R)—N-(5-(2-(Butylamino)-1-hydroxyethyl)pyrimidin-2-yl)isobutyramide Hydrochloride

(a) N-(5-Bromopyrimidin-2-yl)isobutyramide

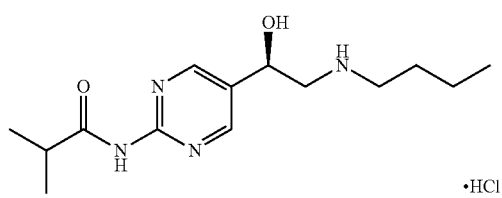 [SMILES: CCCCNC[C@H](O)c1cnc(NC(=O)C(C)C)nc1 ; Cl]

Isobutyric anhydride (2.20 mL, 13.3 mmol) was added in one portion to a mixture of 5-bromopyrimidin-2-amine (550 mg; 3.16 mmol), DMAP (405.5 mg, 3.32 mmol) and pyridine (5 mL). The mixture was stirred at 100° C. for 18 h and allowed to cool. Water was added and the mixture was stirred at rt for 30 min and extracted with Et$_2$O. The combined extracts were washed with brine, dried (Na$_2$SO$_4$) and concentrated to give the sub-title compound (376 mg, 1.54 mmol, 49%).

(b) N-(5-(1-Ethoxyvinyl)pyrimidin-2-yl)isobutyramide

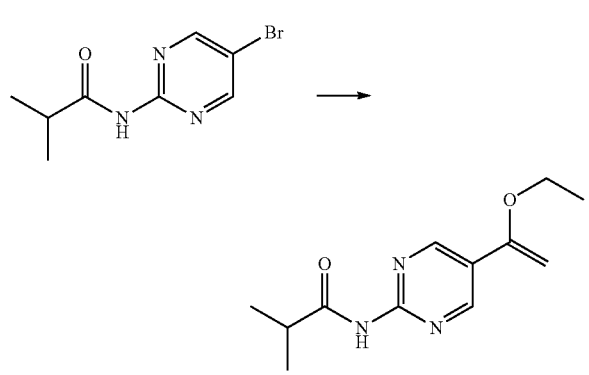

1-Ethoxyvinyltributyltin (0.30 mL, 0.74 mmol) was added to a mixture of N-(5-bromo-pyrimidin-2-yl)isobutyramide (165 mg, 0.68 mmol), (Ph₃P)₂PdCl₂ (14.2 mg, 0.02 mmol) and DMF (3 mL). The mixture was heated under microwave irradiation at 70° C. for 3 h and allowed to cool. KF (aq) was added and the mixture was sonicated for 1 h. Water was added and the mixture was stirred at rt for 30 min and extracted with CH₂Cl₂. The combined extracts were dried (MgSO₄) and concentrated. The residue was purified by chromatography to give the sub-title compound (132 mg, 0.56 mmol, 83%).

(c) N-(5-(2-Bromoacetyl)pyrimidin-2-yl)isobutyramide

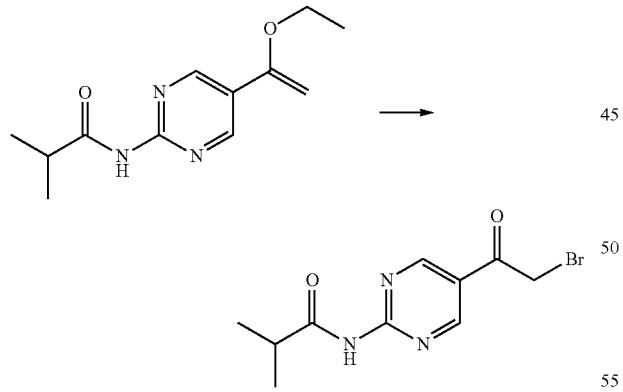

N-Bromosuccinimide (345 mg, 1.94 mmol) was added in one portion to a mixture of N-(5-(1-ethoxyvinyl)pyrimidin-2-yl)isobutyramide (415 mg, 1.94 mmol), THF (5 mL) and H₂O (5 mL) at 0° C. The mixture was allowed to come to rt over 1 h and concentrated to remove THF. H₂O was added and the mixture was extracted with EtOAc. The combined extracts were dried over MgSO₄ and concentrated. The residue was purified by chromatography to give the sub-title compound (185 mg, 0.65 mmol, 37%).

(d) tert-Butyl butyl(2-(2-isobutyramidopyrimidin-5-yl)-2-oxoethyl)carbamate

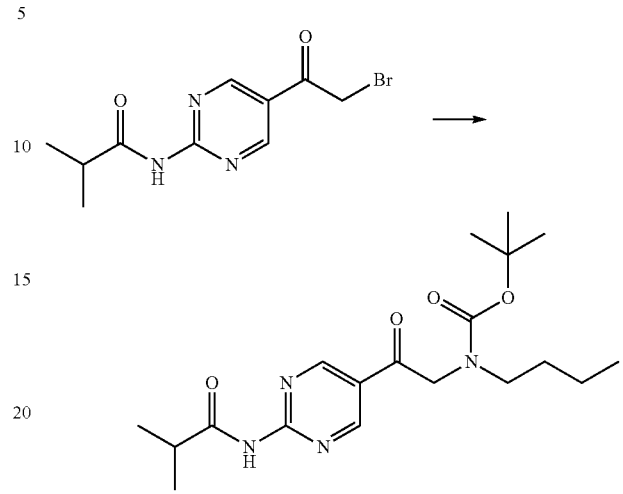

The sub-title compound was prepared from N-(5-(2-bromoacetyl)pyrimidin-2-yl)isobutyramide in accordance with the procedure in Example 1, Step (c).

(e) tert-Butyl (R)-butyl(2-hydroxy-2-(2-isobutyramidopyrimidin-5-yl)ethyl)carbamate

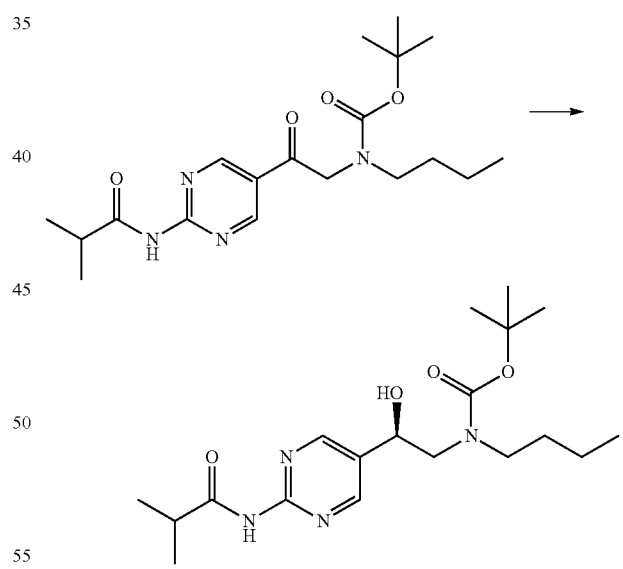

(S, S)—N-(p-Toluenesulfonyl)-1,2-diphenylethanediamine(choro)(p-cymene)ruthenium(II) (9.4 mg, 0.015 mmol) was added to a mixture of tert-butyl butyl (2-(2-isobutyramido-pyrimidin-5-yl)-2-oxoethyl)carbamate (56 mg, 0.15 mmol), formic acid/Et₃N (5:2, 0.30 mL) and DMF (3 mL). The mixture was stirred at rt for 2.5 h. H₂O was added and the mixture extracted with CH₂Cl₂. The combined extracts were dried (Na₂SO₄) and concentrated. The residue was purified by chromatography to give the sub-title compound (45 mg, 0.12 mmol, 80%).

(f) (R)—N-(5-(2-(Butylamino)-1-hydroxyethyl)pyrimidin-2-yl)isobutyramide Hydrochloride

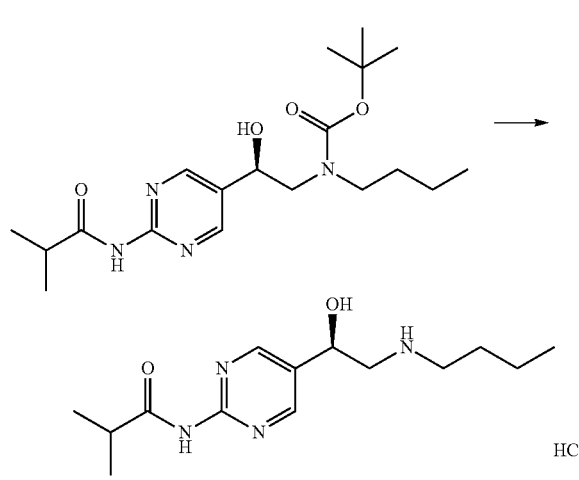

HCl (1 M in Et₂O, 6 mL) was added to tert-butyl (R)-butyl(2-hydroxy-2-(2-isobutyramido-pyrimidin-5-yl)ethyl)carbamate (50 mg, 0.13 mmol) at rt and the mixture was stirred at rt for 2 h. The solids were collected and purified by reverse-phase chromatography to give the title compound (15 mg, 0.047 mmol, 36%).

Example 11: (R)-1-(2-Aminopyrimidin-5-yl)-2-(butylamino)ethan-1-ol

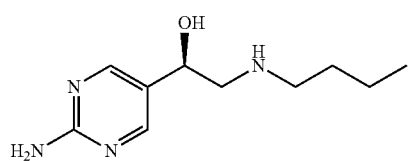

K₂CO₃ (35.5 mg, 0.26 mmol) was added to a mixture of (R)—N-(5-(2-(Butylamino)-1-hydroxyethyl)pyrimidin-2-yl)isobutyramide hydrochloride (see Example 11, step (f), 24 mg, 0.076 mmol) and MeOH (4 mL). The mixture was heated at 65° C. for 2 h, allowed to cool, filtered and concentrated. The residue was purified by chromatography to give the title compound (11 mg, 0.052 mmol, 69%).

¹H NMR (400 MHz, D₂O): δ 8.35 (s, 2H), 4.77-4.81 (m, 1H (intersects with the solvent), 2.96 (dd, J=12.7, 8.2 Hz, 1H), 2.87 (dd, J=12.7, 5.2 Hz, 1H), 2.66 (tt, J=7.2, 3.7 Hz, 1H), 1.43-1.53 (m, 2H), 1.26-1.39 (m, 2H), 0.91 (t, J=7.4 Hz. 3H).

Example 12: (S)-6-(2-(tert-Butylamino)-1-hydroxyethyl)pyridin-3-ol

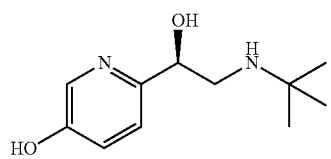

(a) 1-(5-(Benzyloxy)pyridin-2-yl)ethan-1-one

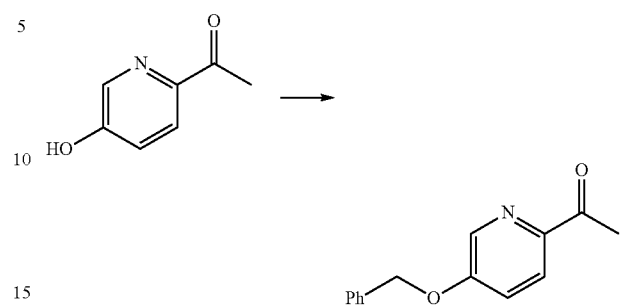

K₂CO₃ (504 mg, 3.65 mmol) followed benzylbromide (0.22 mL, 1.82 mmol) was added to a solution of 1-(5-hydroxypyridin-2-yl)ethanone (250 mg, 1.82 mmol) in MeCN (8 mL) at rt. The mixture was stirred at rt overnight and filtered. The filtrate was concentrated and the residue purified by chromatography to give the sub-title compound (360 mg, 1.58 mmol, 87%).

(b) 1-(5-(Benzyloxy)pyridin-2-yl)-2-bromoethan-1-one

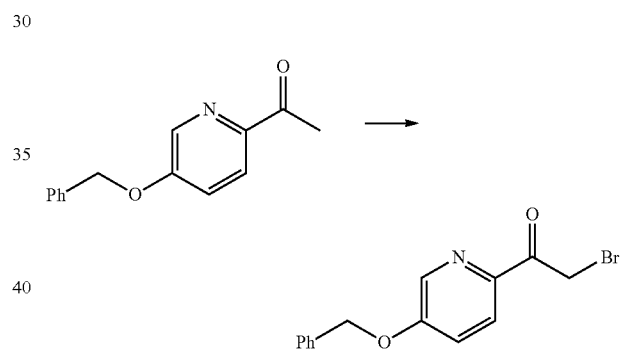

HBr (33% in AcOH, 3.2 mL) was added to a solution of 1-(5-(benzyloxy)pyridin-2-yl)ethan-1-one (320 mg, 1.41 mmol) in AcOH (6.4 mL) at rt. The mixture was cooled in an ice-bath and Br₂ (72.4 µL, 0.141 mmol) was added dropwise. The ice-bath was removed and the mixture was stirred at rt for 2 h and filtered. The solids were washed with Et₂O and treated with NaHCO₃ (aq, sat). The mixture was extracted with CH₂Cl₂ and the combined extracts dried (Na₂SO₄), filtered and concentrated to give the sub-title compound (355 mg, 1.16 mmol, 82%).

(c) 1-(5-(Benzyloxy)pyridin-2-yl)-2-chloroethan-1-one

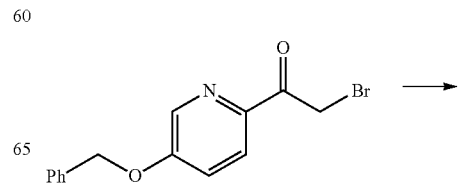

-continued

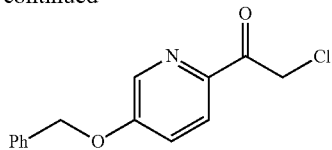

NaCl (1.15 g (19.6 mmol) was added to a mixture of 1-(5-(benzyloxy)pyridin-2-yl)-2-bromoethan-1-one (300 mg, 0.98 mmol), THF (5.2 mL) and H₂O (3.5 mL) at rt. The mixture was vigorously stirred at 70° C. for 20 h, diluted with EtOAc, washed with brine, dried (MgSO₄) and concentrated. The residue was purified by chromatography to give the sub-title compound (240 mg, 0.92 mmol, 94%).

(d) (R)-1-(5-(Benzyloxy)pyridin-2-yl)-2-chloro-ethan-1-ol

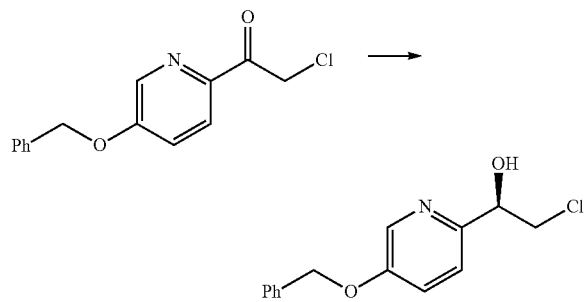

RhClCp*[(1S,2S)-p-TsNCH(C₆H₅)CH(C₆H₅)NH₂]/HCl.Et₃N (30.4 mg, 39 μmol), prepared from dichloro(pentamethylcyclopentadienyl)rhodium(III) dimer, (1S,2S)-(+)—N-(4-toluene-sulphonyl)-1,2-diphenylethylene diamine and Et₃N as described in WO 2008/054155, was added to a mixture of 1-(5-(benzyloxy)pyridin-2-yl)-2-chloroethan-1-one (205 mg, 0.78 mmol) in THF (2.8 mL). Formic acid/Et₃N (5:2, 0.28 mL) was added and the mixture was stirred at rt for 1 h. The mixture was diluted with EtOAc, washed with H₂O, dried (Na₂SO₄), filtered and concentrated. The residue was purified by chromatography to give the sub-title compound (201 mg, 0.76 mmol, 97%, ee=95%).

(e) (R)-5-(Benzyloxy)-2-(oxiran-2-yl)pyridine

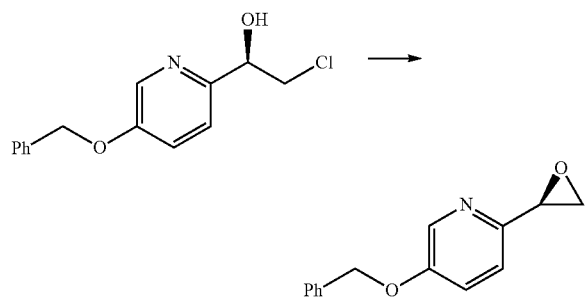

NaOH (aq, 1 M, 1.73 mL, 1.73 mmol) was added to a solution of (R)-1-(5-(benzyloxy)-pyridin-2-yl)-2-chloroethan-1-ol (12.0 mg, 0.05 mmol) in iPrOH (1.2 mL). The mixture was stirred at rt for 1 h and diluted with EtOAc. The organic layer was washed with H₂O, brine, dried over Na₂SO₄ and concentrated to give the sub-title compound (123 mg, 0.54 mmol, 94%) which was used in the next step without any further purification.

(f) (S)-1-(5-(Benzyloxy)pyridin-2-yl)-2-(tert-butylamino)ethan-1-ol

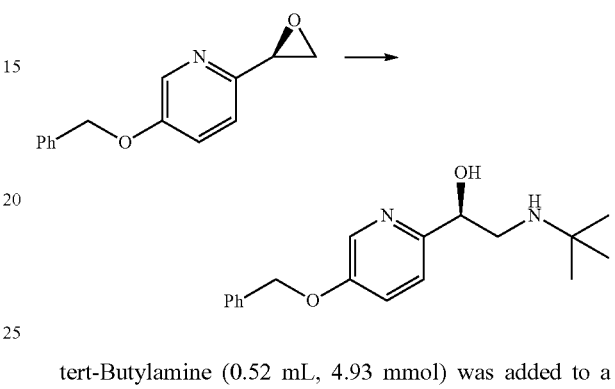

tert-Butylamine (0.52 mL, 4.93 mmol) was added to a mixture of (R)-5-(benzyloxy)-2-(oxiran-2-yl)pyridine (112 mg, 0.49 mmol) and iPrOH (0.39 mL) at rt. The mixture was heated at 70° C. for 16 h, cooled and concentrated. The residue was crystallized from CH₂Cl₂/hexane (1:5) to give the sub-title compound (136 mg, 0.45 mmol, 92%).

(g) (S)-6-(2-(tert-Butylamino)-1-hydroxyethyl)pyridin-3-ol

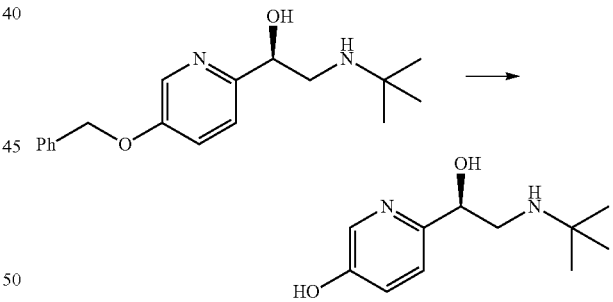

Et₃SiH (0.40 mL, 2.50 mmol) was added to a mixture of (S)-1-(5-(benzyloxy)pyridin-2-yl)-2-(tert-butylamino)ethan-1-ol (75 mg, 0.25 mmol), Pd—C (10%, 53.1 mg, 0.05 mmol) and MeOH (0.6 mL) at rt. The mixture was stirred at rt for 10 min, filtered through Celite and concentrated. H₂O was added to the residue and the mixture was extracted with CH₂Cl₂. The aq phase was concentrated, treated with EtOH and filtered through Celite. Concentration gave the title compound (49 mg, 0.23 mmol, 93%, ee=95%).

¹H NMR (400 MHz, CDCl₃): 5.56 (d, J=2.4 Hz, 1H), 7.08 (d, J=8.4 Hz, 1H), 6.82 (dd, J=8.4, 2.8 Hz, 1H), 4.86 (t, J=3.8 Hz, 1H), 3.21 (dd, J=11.6, 4.0 Hz, 1H), 3.00 (dd, J=11.6, 3.6 Hz, 1H), 1.22 (s, 9H).

Example 13: (R)-5-(2-(tert-Butylamino)-1-hydroxyethyl)pyridin-3-ol dihydrochloride

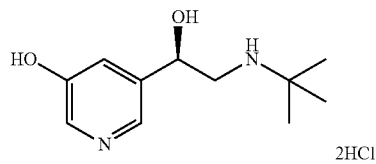

2HCl

(a) 3-(Benzyloxy)-5-bromopyridine

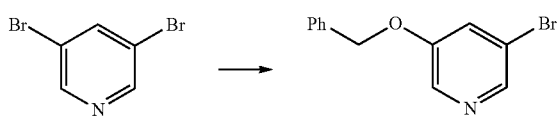 [SMILES: Brc1cncc(Br)c1 ; Brc1cncc(OCc2ccccc2)c1]

NaH (60% in mineral oil, 1.27 g, 31.66 mmol) was washed with hexane. DMF (20 mL) was added and the mixture cooled in an ice-bath. Benzyl alcohol (3.28 mml, 31.66 mmol) was added dropwise over 30 min and the mixture stirred for 20 min at rt. 3,5-dibromopyridine (5.00 g, 21.11 mmol) was added in one portion and the mixture was stirred at rt for 18 h. NH₄Cl (aq, 10%) was slowly added followed by Et₂O. The layers were separated and the aq phase extracted with Et₂O. The combined extracts were washed with brine, dried (Na₂SO₄) and concentrated. The residue was purified by chromatography to give the sub-title compound (3.86 g, 14.61 mmol, 69%).

(b) 1-(5-(Benzyloxy)pyridin-3-yl)-2-chloroethan-1-one

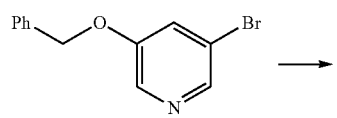

Isopropylmagnesium chloride (2 M in THF, 7.63 mL, 15.26 mmol) was added dropwise to a solution of 3-(benzyloxy)-5-bromopyridine (3.10 g, 11.74 mmol) in THF (20 mL) at 0° C. The mixture was stirred at rt for 90 min and a solution of 2-choro-N-methoxy-N-methylacetamide (1.78 g, 12.9 mmol) in THF (20 mL) was added dropwise. The mixture was stirred at rt for 1 h. NH₄Cl (aq, 10%) was added and the mixture was extracted with Et₂O. The combined extracts were washed with brine, dried (Na₂SO₄) and concentrated. The residue was purified by chromatography to give the sub-title compound (1.00 g, 3.82 mmol, 33%).

(c) (R)-1-(5-(Benzyloxy)pyridin-3-yl)-2-chloroethan-1-ol

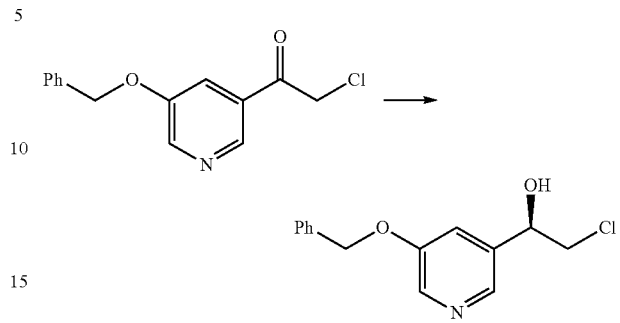

The sub-title compound was prepared from 1-(5-(benzyloxy)pyridin-3-yl)-2-chloroethan-1-one in accordance with the procedure in Example 13, Step (d).

(d) (R)-1-(5-(Benzyloxy)pyridin-3-yl)-2-(tert-butylamino)ethan-1-ol

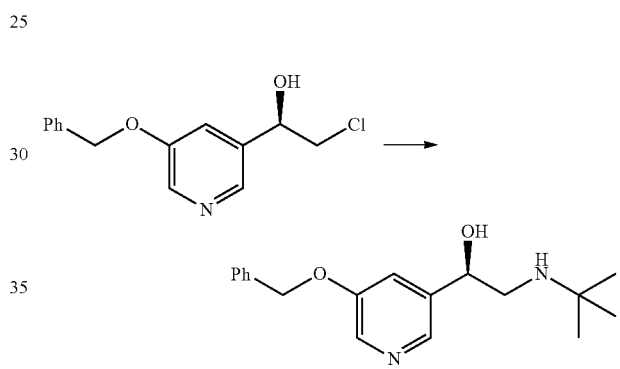

tert-Butylamine (2.43 mL, 23.13 mmol) followed by NaOH (101.77 mg, 2.54 mmol) were added to a mixture of (R)-1-(5-(benzyloxy)pyridin-3-yl)-2-chloroethan-1-ol (610 mg, 2.31 mmol) and iPrOH (0.35 mL, 4.63 mmol) at rt. The mixture was stirred at 85° C. for 9 h, diluted with EtOAc, washed with H₂O and brine, dried (Na₂SO₄) and concentrated. The residue was purified by chromatography to give the sub-title compound (305 mg, 1.02 mmol, 44%, ee=80%).

(e) (R)-5-(2-(tert-Butylamino)-1-hydroxyethyl)pyridin-3-ol dihydrochloride

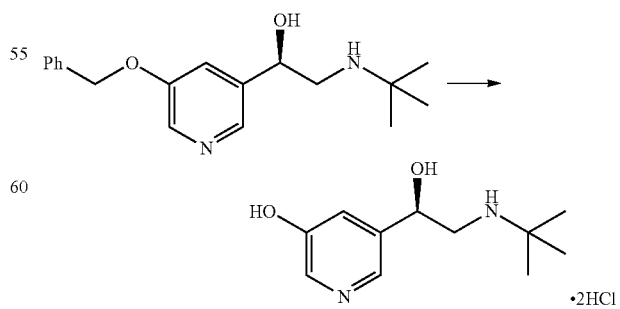

A mixture of (R)-1-(5-(benzyloxy)pyridin-3-yl)-2-(tert-butylamino)ethan-1-ol (300 mg, 1.00 mmol), 10% Pd—C (212.56 mg, 0.20 mmol) and iPrOH (15 mL) was hydrogenated at 8 atm at rt for 2 h, filtered through Celite and concentrated. The residue was dissolved in Et$_2$O (20 mL) and MeOH (3 mL), and HCl (2 M in Et$_2$O, 1.00 mL, 2.00 mmol) was added. The mixture was stirred at rt for 20 min and kept at 20° C. for 2 h. The solids were collected, washed with Et$_2$O and dried to give the title compound (210 mg, 0.74 mmol, 74%).

$^1$H NMR (400 MHz, D$_2$O) δ 8.43 (s, 1H), 8.35 (d, J=2.6 Hz, 1H), 8.13-8.06 (m, 1H), 5.25 (dd, J=10.2, 3.0 Hz, 1H), 3.44 (dd, J=12.9, 3.1 Hz, 1H), 3.26 (dd, J=12.9, 10.2 Hz, 1H), 1.42 (s, 9H).

Example 14: 4-(2-(tert-Butylamino)-1-hydroxyethyl)pyridin-3-ol hydrochloride

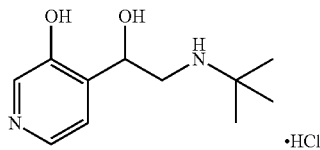

(a) 1-(3-(Benzyloxy)pyridin-4-yl)ethan-1-one

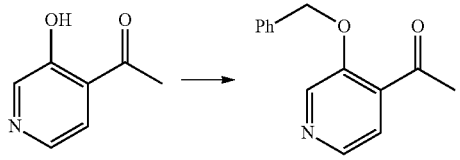

NaH (60% in mineral oil, 35 mg, 0.88 mmol) was washed with n-pentane, and THF (2 mL) was added. The mixture was cooled in an ice-bath and 4-acetyl-3-hydroxypyridine (100 mg, 0.73 mmol) was added in portions. After 5 min, 15-crown-5 (16 mg, 73 µmol) was added and the mixture was stirred for 20 min at 0° C. Benzylbromide (95 µL, 0.80 mmol) was added dropwise and the mixture was stirred at 0° C. for 10 min and at rt for 16 h. MeOH (5 mL) was added and the mixture concentrated. CH$_2$Cl$_2$ was added to the residue and the mixture filtered through Celite and concentrated. The residue was purified by chromatography to give the sub-title compound (62 mg, 0.27 mmol, 37%).

(b) 1-(3-(Benzyloxy)pyridin-4-yl)-2-bromoethan-1-one

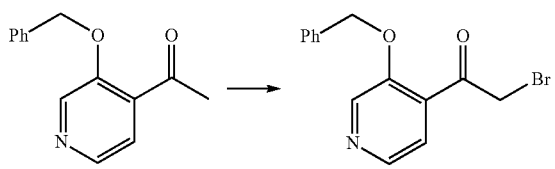 [SMILES: CC(=O)c1ccncc1OCc1ccccc1 ; O=C(CBr)c1ccncc1OCc1ccccc1]

The sub-title compound was prepared from 1-(3-(benzyloxy)pyridin-4-yl)ethan-1-one in accordance with the procedure in Example 13, Step (b).

(c) 3-(Benzyloxy)-4-(oxiran-2-yl)pyridine

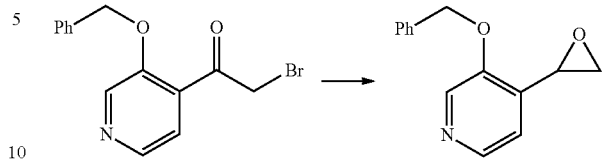

NaBH$_4$ (2.93 mg, 77 µmol) was added to a mixture of 1-(3-(benzyloxy)pyridin-4-yl)-2-bromoethan-1-one (100 mg, 0.26 mmol) and iPrOH (0.5 mL) at 0° C. The cooling bath was removed and the mixture was stirred at rt for 1 h. K$_2$CO$_3$ (35.7 mg, 0.26 mmol) was added at rt and the mixture was stirred at for 5 h. The mixture was filtered through Celite and the solids washed with iPrOH (0.3 mL). The filtrate was used as is in the next step.

(d) 1-(3-(Benzyloxy)pyridin-4-yl)-2-(tert-butylamino)ethan-1-ol

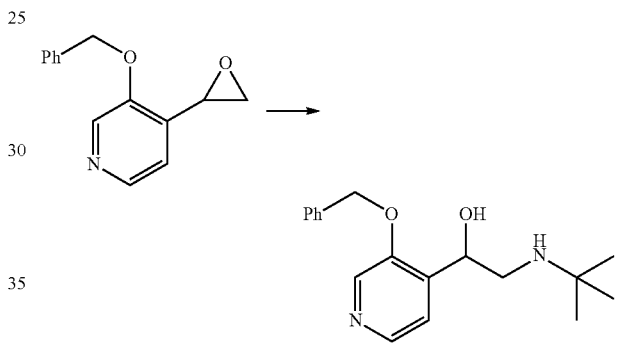

tert-Butylamine (0.19 mL, 1.85 mmol) was added to a solution 3-(benzyloxy)-4-(oxiran-2-yl)pyridine (0.18 mmol in iPrOH; see Example 15, Step (b)) at rt. The mixture was heated at 70° C. for 16 h and concentrated. The residue was purified by chromatography to give the sub-title compound (36 mg, 0.12 mmol, 65%).

(e) 4-(2-(tert-Butylamino)-1-hydroxyethyl)pyridin-3-ol hydrochloride

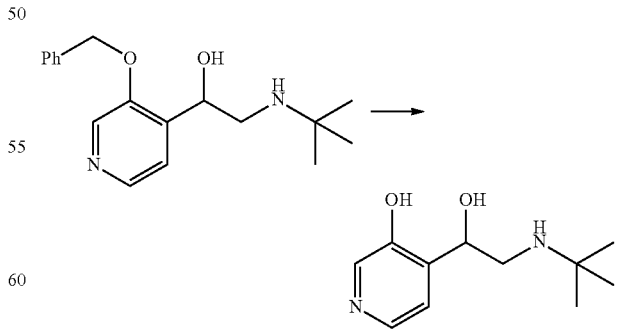

Et$_3$SiH (0.19 mL, 1.20 mmol) was added to a mixture of 1-(3-(benzyloxy)pyridin-4-yl)-2-(tert-butylamino)ethan-1-ol (36 mg, 0.12 mmol), Pd—C (10%, 25.5 mg, 0.024 mmol) and MeOH (0.2 mL) at rt. The mixture was stirred at rt for 10 min, filtered through Celite and concentrated. The residue was purified by chromatography and dissolved in dioxane. HCl (4 M in dioxane, 50 µL, 0.20 mmol) was added and the solid collected and dried to give the title compound (26 mg, 0.11 mmol, 88%).

¹H NMR (400 MHz, CD₃OD): δ. 8.03-8.01 (m, 1H), 7.37 (d, J=8.4 Hz, 1H), 7.18 (dd, J=8.4, 2.8 Hz, 1H), 4.78 (dd, J=8.8, 3.6 Hz, 1H), 3.09 (dd, J=12.0, 4.0 Hz, 1H), 2.96 (dd, J=11.8, 9.0 Hz, 1H), 1.27 (s, 9H).

Example 15: (R)-4-(2-(tert-Butylamino)-1-hydroxyethyl)-1-methylpyridin-2(1H)-one

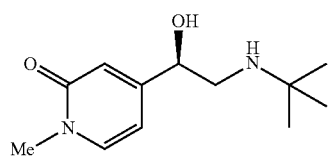 [SMILES: Cn1ccc([C@@H](O)CNC(C)(C)C)cc1=O]

(a) 4-Bromo-1-methylpyridin-2(1H)-one

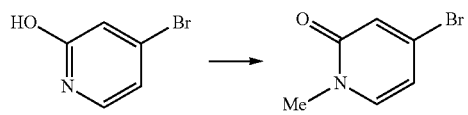

Methyl iodide (1.79 mL, 28.74 mmol) was added to a mixture of 4-bromo-2-hydroxypyridine (1.00 g, 5.75 mmol), K₂CO₃ (4.05 g, 29.31 mmol) and MeCN (30 mL) at rt. The Mixture was heated at 50° C. for 3 h, concentrated and treated with H₂O. The mixture was extracted with CH₂Cl₂ and the combined extracts dried (Na₂SO₄) and concentrated. The residue was crystallized from Et₂O/hexane to give the sub-title compound (640 mg, 3.40 mmol, 59%).

(b) 4-(1-Ethoxyvinyl)-1-methylpyridin-2(1H)-one

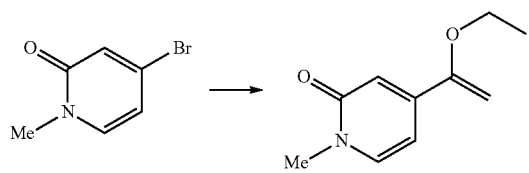

1-Ethoxyvinyltributyltin (1.00 mL, 2.93 mmol) was added to a mixture of 4-bromo-1-methylpyridin-2(1H)-one (500 mg, 2.65 mmol), (Ph₃P)₂PdCl₂ (18.7 mg, 26.6 µmol) and toluene (10 mL). The mixture was heated at 100° C. for 20 h and allowed to cool. KF (0.6 g in 12 mL H₂O) was added and the mixture was stirred at rt for 15 min. EtOAc (20 mL) was added and the mixture filtered through Celite. The layers in the filtrate were separated and the aq phase extracted with EtOAc. The combined extracts were washed with brine, dried (MgSO₄) and concentrated. The residue was purified by chromatography to give the sub-title compound (420 mg, 2.34 mmol, 88%).

(c) 4-(2-Chloroacetyl)-1-methylpyridin-2(1H)-one

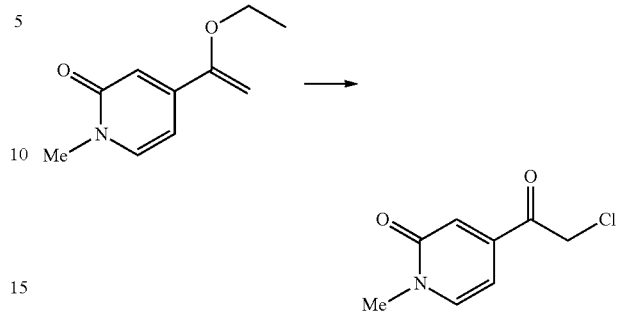

H₂O (3.2 mL) followed by N-chlorosuccinimide (297 mg, 2.23 mmol) in one portion, were added to a solution of 4-(1-ethoxyvinyl)-1-methylpyridin-2(1H)-one (380 mg, 2.12 mmol), in THF (16 mL) at rt. The mixture was stirred at rt for 2 d and CH₂Cl₂ was added. The organic phase was collected, dried (Na₂SO₄) and concentrated. The residue was crystallized from MeCN to give the sub-title compound (190 mg, 1.02 mmol, 48%).

(d) (R)-4-(2-Chloro-1-hydroxyethyl)-1-methylpyridin-2(1H)-one

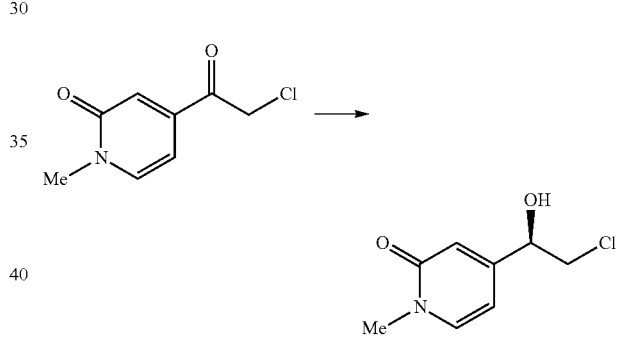

The sub-title compound was prepared from 4-(2-chloroacetyl)-1-methylpyridin-2(1H)-one in accordance with the procedure in Example 13, Step (d).

(e) (R)-4-(2-(tert-Butylamino)-1-hydroxyethyl)-1-methylpyridin-2(1H)-one

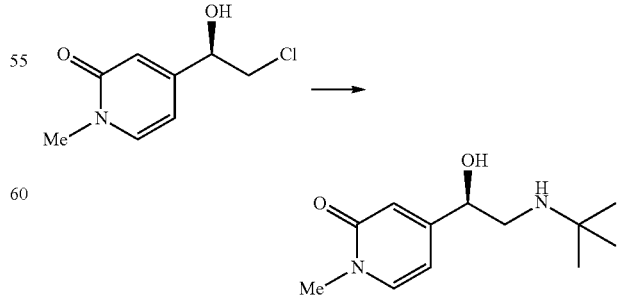

tert-Butylamine (0.45 mL, 4.26 mmol) followed by NaOH (17.05 mg, 0.43 mmol) were added to a mixture of ((R)-4-(2-chloro-1-hydroxyethyl)-1-methylpyridin-2(1H)-one (80 mg, 0.43 mmol) and MeOH (0.20 mL) at rt. The mixture was stirred at 80° C. for 90 min, allowed to cool and concentrated. H₂O was added to the residue and the mixture extracted with EtOAc. The combined extracts were dried (Na₂SO₄) and concentrated. The residue was purified by reverse-phase chromatography to give the title compound (21 mg, 93.6 μmol, 22%, ee=95%).

¹H NMR (400 MHz, D₂O): δ 7.51 (d, J=6.9 Hz, 1H), 6.48-6.47 (m, 1H), 6.40 (dd, J=6.9, 1.9 Hz, 1H), 4.51 (dd, J=8.2, 4.3 Hz, 1H), 3.43 (s, 3H), 2.72-2.57 (m, 2H), 0.95 (s, 9H).

Example 16: (S)-2-(tert-Butylamino)-1-(5-fluoro-pyridin-2-yl)ethan-1-0

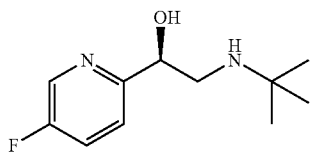

(a) 2-Chloro-1-(6-fluoropyridin-3-yl)ethan-1-one

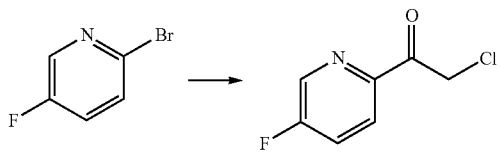 [SMILES: Fc1ccc(Br)nc1 ; O=C(CCl)c1ccc(F)cn1]

Isopropylmagnesium chloride (2 M in THF, 4.26 mL, 8.52 mmol) was added dropwise to a solution of 2-bromo-5-fluoropyridine (750 mg, 4.26 mmol) in THF (6 mL) at rt. The mixture was stirred at rt for 2 h and a solution of 2-chloro-N-methoxy-N-methylacetamide (703.5 mg, 5.11 mmol) 1 n THF (6 mL) was added dropwise. The mixture was stirred at rt for overnight and poured into HCl (aq, 2 M, 8 mL) and ice (150 g). The mixture was extracted with Et₂O. The combined extracts were washed with brine, dried (Na₂SO₄) and concentrated. The residue was purified by chromatography to give the sub-title compound (280 mg, 1.61 mmol, 38%).

(b) (R)-2-Chloro-1-(5-fluoropyridin-2-yl)ethan-1-ol

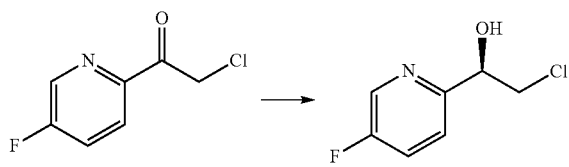 [SMILES: O=C(CCl)c1ccc(F)cn1 ; O[C@@H](CCl)c1ccc(F)cn1]

The sub-title compound was prepared from 2-chloro-1-(6-fluoropyridin-3-yl)ethan-1-one in accordance with the procedure in Example 13, Step (d).

(c) (S)-2-(tert-Butylamino)-1-(5-fluoropyridin-2-yl)ethan-1-ol

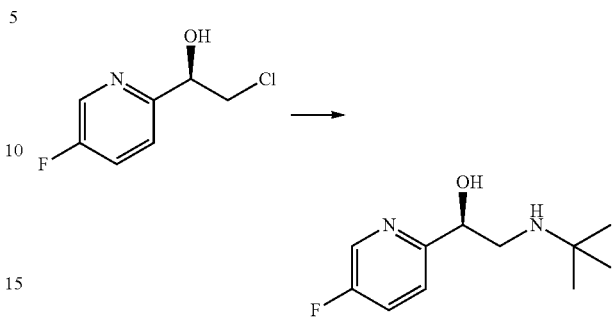

tert-Butylamine (1.56 mL, 14.86 mmol) followed by NaOH (59.45 mg, 1.48 mmol) were added to a mixture of (R)-2-Chloro-1-(5-fluoropyridin-2-yl)ethan-1-ol (261 mg, 1.49 mmol) and iPrOH (1.14 mL, 14.86 mmol) at rt. The mixture was heated at 65° C. for 2 h, allowed to cool and concentrated. The residue was sonicated with CH₂Cl₂ (100 mL), washed with H₂O dried (Na₂SO₄) and concentrated. The residue was purified by chromatography to give the title compound (92 mg, 10.43 mmol, 29%).

¹H NMR (400 MHz, CDCl₃): δ 8.38 (d, 1H, J=2.6 Hz), 7.49 (dd, 1H, J=8.6 Hz, 4.6 Hz), 7.40 (td, 1H, J=8.6 Hz, 2.7 Hz), 4.67 (dd, 1H, J=7.9 Hz, 3.9 Hz), 3.02 (dd, 1H, J=11.7 Hz, 3.9 Hz), 2.68 (dd, 1H, J=11.7, 8.0 Hz), 2.95-2.23 (bs, 2H), 1.09 (s, 9H).

Example 17: (R)-2-(tert-Butylamino)-1-(5-fluoropyridin-3-yl)ethan-1-0!

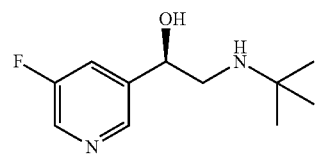

(a) 2-Chloro-1-(5-fluoropyridin-3-yl)ethan-1-one

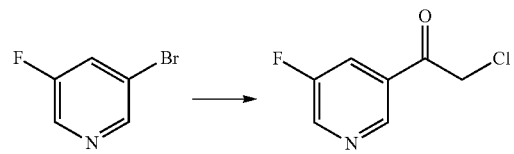 [SMILES: Fc1cncc(Br)c1 ; O=C(CCl)c1cncc(F)c1]

Isopropylmagnesium chloride (2 M in THF, 10.47 mL, 20.94 mmol) was added to a solution of LiCl (887.69 mg, 20.94 mmol) in THF (8 mL) at rt. After 15 min at rt, 3-bromo-5-fluoropyridine (3.35 g, 19.04 mmol) in THF (30 mL) was added dropwise at 0° C. The mixture was stirred at rt for 2 h and cooled in an ice-bath. A solution of 2-chloro-N-methoxy-N-methylacetamide (2.62 g, 19.04 mmol) 1 THF (30 mL) was added dropwise, and the mixture was stirred at rt for 2 h. NH₄Cl (aq, 10%) was added and the mixture was extracted with Et₂O. The combined extracts were washed with brine, dried (Na₂SO₄) and concentrated. The residue was purified by chromatography to give the sub-title compound (1.52 g, 20.94 mmol, 46%).

(b) (R)-2-Chloro-1-(5-fluoropyridin-3-yl)ethan-1-one

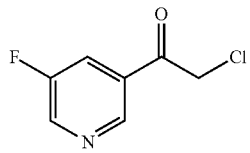
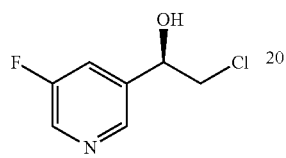

The sub-title compound was prepared from 2-chloro-1-(5-fluoropyridin-3-yl)ethan-1-one in accordance with the procedure in Example 13, Step (d), with the exception that the reaction time was 15 min. ee=92.5%.

(c) (R)-2-(tert-Butylamino)-1-(5-fluoropyridin-3-yl)ethan-1-ol

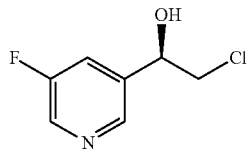
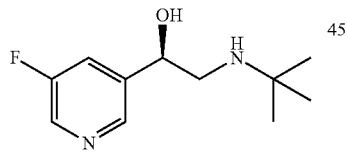

tert-Butylamine (11.37 mL, 108.21 mmol) followed by NaOH (476.08 mg, 11.90 mmol) were added to a mixture of 2-chloro-1-(5-fluoropyridin-3-yl)ethan-1-one (1.90 g, 10.82 mmol) and iPrOH (1.66 mL, 21.64 mmol) at rt. The mixture was heated at 75° C. for 4 h, allowed to cool, diluted with EtOAc, washed with H₂O and brine, dried (Na₂SO₄) and concentrated. The residue was dissolved in hot EtOAc and allowed to cool. Pentane was added and the mixture kept at −20° C. overnight. The solids were collected and purified by chromatography to give the title compound (1.43 g, 6.74 mmol, 62%, ee=98%). 20 ¹H NMR (400 MHz, CDCl₃): δ 8.43-8.27 (m, 2H), 7.57-7.42 (m, 1H), 4.62 (dd, J=8.8, 3.7 Hz, 1H), 2.94 (dd, J=12.1, 3.8 Hz, 1H), 2.53 (dd, J=12.1, 8.8 Hz, 1H), 1.10 (s, 9H).

Example 18: (R)-2-(tert-Butylamino)-1-(3-fluoropyridin-4-yl)ethan-1-ol

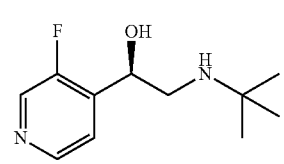

(a) 2-Chloro-1-(3-fluoropyridin-4-yl)ethan-1-one

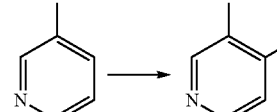

n-Butyllithium (2.5 M in hexane, 2.58 mL, 6.44 mmol) was added dropwise to a mixture of diisopropylamine (0.87 mL, 6.18 mmol) in Et₂O (30 mL) at −10° C. After 30 min the mixture was cooled to −60° C. and a solution of 3-fluoropyridine (0.44 mL, 5.15 mmol) in Et₂O (10 mL) was added dropwise at −60° C. After 45 min a solution of 2-chloro-N-methoxy-N-methylacetamide (708.49 mg, 5.15 mmol) 1 in Et₂O (10 mL) was added dropwise at −60° C. and the mixture was stirred at −60° C. for 1 h. The cooling bath was removed and NH₄C (aq, 10%, 20 mL) was carefully added. The organic phase was collected, diluted with EtOAc, washed with NH₄Cl (aq, 10%), brine, dried (Na₂SO₄), filtered through silica gel and concentrated. The residue was partitioned between H₂O and CH₂Cl₂ and the aq phase was washed with CH₂Cl₂. The combined organic phases were dried (Na₂SO₄) and concentrated to give the sub-title compound (750 mg, 4.32 mmol, 84%).

(b) (R)-2-Chloro-1-(3-fluoropyridin-4-yl)ethan-1-ol

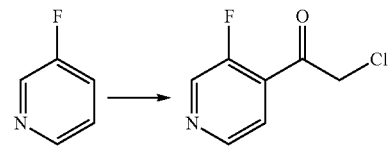 [SMILES: Fc1cccnc1 ; O=C(CCl)c1ccncc1F]

The sub-title compound was prepared from 2-chloro-1-(3-fluoropyridin-4-yl)ethan-1-one in accordance with the procedure in Example 13, Step (d), with the exception that the reaction time was 90 min.

(c) (R)-2-(tert-Butylamino)-1-(3-fluoropyridin-4-yl)ethan-1-ol

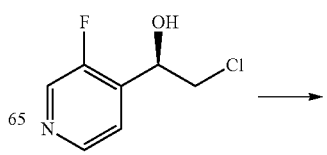

-continued

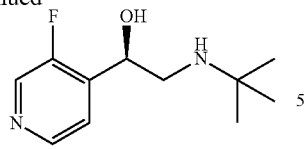

tert-Butylamine (1.71 mL, 16.23 mmol) followed by NaOH (43.28 mg, 1.08 mmol) were added to a mixture of (R)-2-chloro-1-(3-fluoropyridin-4-yl)ethan-1-ol (1.90 g, 10.82 mmol) and iPrOH (1.66 mL, 21.64 mmol) at rt. The mixture was heated at 75° C. overnight, allowed to cool, diluted with EtOAc, washed with H$_2$O and brine, dried (Na$_2$SO$_4$) and concentrated. The residue was dissolved in Et$_2$O and filtered through amino-functionalized silica gel and concentrated. The residue was dissolved in a small amount of EtOAc and pentane was added. The mixture kept at −20° C. overnight and the solids were collected and dried to give the title compound (40 mg, 0.19 mmol, 17%, ee=58%).

$^1$H NMR (400 MHz, CDCl$_3$): δ 8.41 (dd, J=4.9, 1.2 Hz, 1H), 8.37 (d, J=1.9 Hz, 1H), 7.54 (s, 1H), 4.89 (dd, J=8.3, 4.0 Hz, 1H), 3.04 (ddd, J=12.1, 3.8, 1.2 Hz, 1H), 2.52 (dd, J=12.1, 8.3 Hz, 1H), 1.11 (s, 9H).

Example 19: (R)-2-(tert-Butylamino)-1-(5-chloro-pyridin-3-yl)ethan-1-0

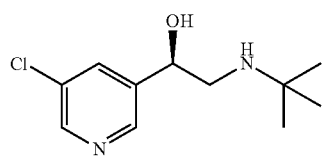

(a) 2-chloro-1-(5-chloropyridin-3-yl)ethan-1-one

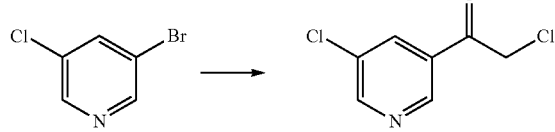

The sub-title compound was prepared from 3-bromo-5-chloropyridine in accordance with the procedure in Example 17, Step (a).

(b) (R)-2-chloro-1-(5-chloropyridin-3-yl)ethan-1-ol

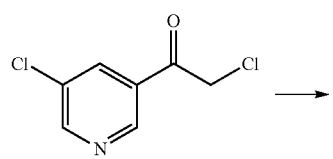

-continued

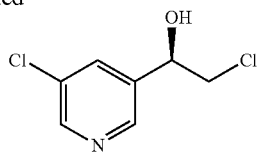

The sub-title compound was prepared from 2-chloro-1-(5-chloropyridin-3-yl)ethan-1-one in accordance with the procedure in Example 18, Step (b). ee=92.5%.

(c) (R)-2-(tert-Butylamino)-1-(5-chloropyridin-3-yl)ethan-1-ol

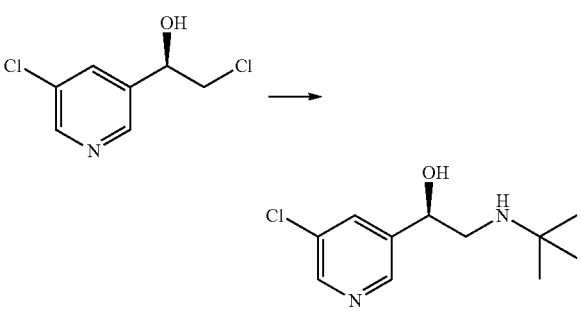

tert-Butylamine (2.46 mL, 23.43 mmol) followed by NaOH (103.09 mg, 2.58 mmol) were added to a mixture of (R)-2-chloro-1-(5-chloropyridin-3-yl)ethan-1-ol (450 mg, 2.34 mmol) and iPrOH (0.36 mL, 4.69 mmol) at rt. The mixture was heated at 90° C. for 5 h, allowed to cool, diluted with EtOAc, washed with H$_2$O and brine, dried (Na$_2$SO$_4$) and concentrated. The residue was dissolved in a small amount of EtOAc and pentane was added. The mixture kept at −20° C. overnight and the solids were collected and dried to give the title compound (340 mg, 1.49 mmol, 63%).

$^1$H NMR (400 MHz, CDCl$_3$): δ 8.48 (d, J=2.4 Hz, 1H), 8.45 (d, J=1.8 Hz, 1H), 7.75 (ddd, J=2.5, 1.9, 0.7 Hz, 1H), 4.61 (dd, J=8.9, 3.7 Hz, 1H), 2.96 (dd, J=12.1, 3.8 Hz, 1H), 2.54 (dd, J=12.1, 8.9 Hz, 1H), 1.12 (s, 9H).

Example 20: (S)-2-(tert-Butylamino)-1-(3-chloro-pyridin-2-yl)ethan-1-ol dihydrochloride

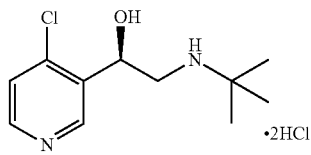

(a) 2-Bromo-1-(3-chloropyridin-2-yl)ethan-1-one hydrobromide

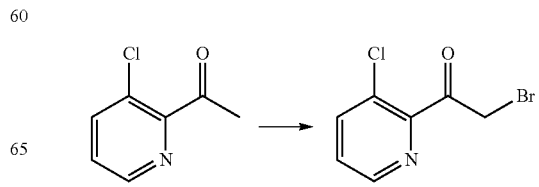

The sub-title compound was prepared from 2-acetyl-3-chloropyridine in accordance with the procedure in Example 13, Step (b).

(b) 2-Chloro-1-(3-chloropyridin-2-yl)ethan-1-one

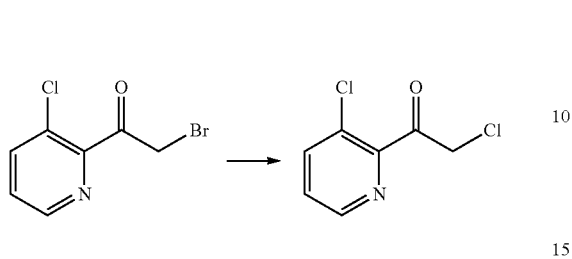

The sub-title compound was prepared from 2-bromo-1-(3-chloropyridin-2-yl)ethan-1-one hydrobromide in accordance with the procedure in Example 13, Step (c).

(c) (R)-2-Chloro-1-(3-chloropyridin-2-yl)ethan-1-ol

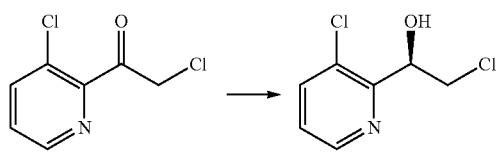 [SMILES: O=C(CCl)c1ncccc1Cl ; O[C@@H](CCl)c1ncccc1Cl]

The sub-title compound was prepared from 2-chloro-1-(3-fluoropyridin-4-yl)ethan-1-one in accordance with the procedure in Example 13, Step (d), with the exception that the reaction time was 2 h and the solvent was DMF instead of THF. ee=91%.

(d) (S)-2-(tert-Butylamino)-1-(3-chloropyridin-2-yl)ethan-1-ol dihydrochloride

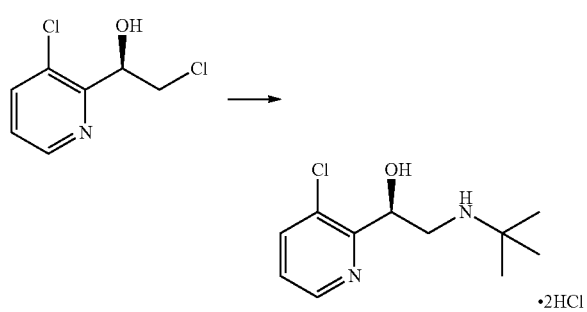

tert-Butylamine (2.71 mL, 25.77 mmol) followed by NaOH (75.60 mg, 1.89 mmol) were added to a mixture of (R)-2-chloro-1-(3-chloropyridin-2-yl)ethan-1-ol (330 mg, 1.72 mmol) and iPrOH (0.26 mL, 3.44 mmol) at rt. The mixture was heated at 90° C. for 3 h, allowed to cool, diluted with EtOAc, washed with H$_2$O and brine, dried (Na$_2$SO$_4$) and concentrated. The residue was dissolved in hot MeCN (10 mL) and kept at rt for 1 h. The solids were collected and dried to give the title compound (140 mg, 0.46 mmol, 27%).
$^1$H NMR (400 MHz, D$_2$O): δ 8.73 (dd, J=5.4, 1.4 Hz, 1H), 8.44 (dd, J=8.4, 1.4 Hz, 1H), 7.88 (dd, J=8.4, 5.4 Hz, 1H), 5.65 (dd, J=9.6, 2.8 Hz, 1H), 3.57 (dd, J=13.0, 2.9 Hz, 1H), 3.31 (dd, J=13.0, 9.6 Hz, 1H), 1.44 (s, 9H).

Example 21: (S)-2-(tert-Butylamino)-1-(5-chloropyridin-2-yl)ethan-1-ol dihydrochloride

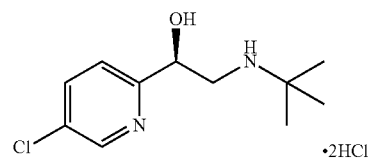

(a) (R)-2-Chloro-1-(5-chloropyridin-2-yl)ethan-1-ol

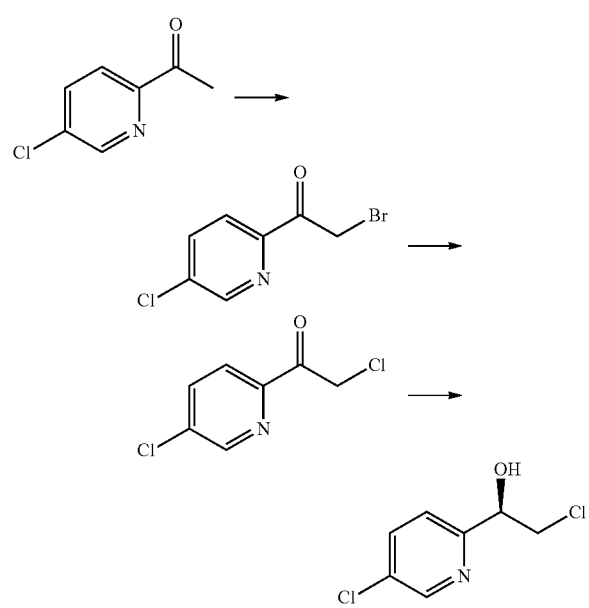

The sub-title compound was prepared from 2-acetyl-5-chloropyridine in accordance with the procedures in Example 21, Steps (a) to (c).

(b) (S)-2-(tert-Butylamino)-1-(5-chloropyridin-2-yl)ethan-1-ol dihydrochloride

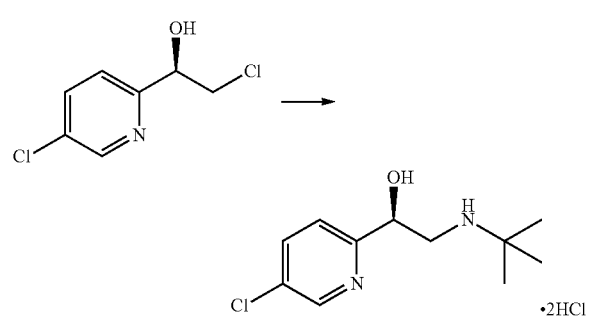

tert-Butylamine (1.56 mL, 14.84 mmol) followed by NaOH (43.53 mg, 1.09 mmol) were added to a mixture of (R)-2-chloro-1-(5-chloropyridin-2-yl)ethan-1-ol (190 mg, 0.99 mmol) and iPrOH (0.15 mL, 1.99 mmol) at rt. The mixture was heated at 90° C. for 3 h, allowed to cool, diluted with EtOAc, washed with H$_2$O and brine, dried (Na$_2$SO$_4$) and concentrated. The residue was dissolved in Et$_2$O and HCl (2 M in Et$_2$O, 0.99 mL, 1.98 mmol) was added. The mixture was concentrated and the residue crystallized from MeCN to give the title compound (120 mg, 0.40 mmol, 40%, ee=90%).

$^1$H NMR (400 MHz, D$_2$O): δ 8.70 (d, J=2.4 Hz, 1H), 8.22 (dd, J=8.6, 2.4 Hz, 1H), 7.79 (d, J=8.6 Hz, 1H), 5.22 (dd, J=9.5, 3.3 Hz, 1H), 3.50 (dd, J=12.9, 3.3 Hz, 1H), 3.30 (dd, J=12.9, 9.5 Hz, 1H), 1.41 (s, 9H).

BIOLOGICAL EXAMPLES

L6-myoblasts were grown in Dulbecco's Modified Eagle's Medium (DMEM) containing 4.5 g/l glucose supplemented with 10% fetal bovine serum, 2 mM L-Glutamine, 50 U/ml penicillin, 50 g/ml streptomycin and 10 mM HEPES. Cells were plated at 1×10$^5$ cells per ml in 24-well plates. After reaching 90% confluence the cells were grown in medium containing 2% FBS for 7 days where upon cells differentiated into myotubes.

Biological Example 1: Glucose Uptake

Differentiated L6-myotubes were serum-starved over night in medium containing 0.5% fatty-acid free BSA and stimulated with agonist, final concentration 1×10$^{-5}$. After 1 h 40 min cells were washed with warm, glucose free medium or PBS and another portion of agonist was added to glucose free medium. After 20 min the cells were exposed to 50 nM $^3$H-2-deoxy-glucose for another 10 min before washed in ice cold glucose free medium or PBS and lysed in 0.2 M NaOH for 1 h in 60° C. Cell lysate was mixed with scintillation buffer (Emulsifier Safe, Perkin Elmer and radio-activity detected in a p-counter (Tri-Carb 2800TR, Perkin Elmer). The activity for each compound is compared to that of isoproterenol. If a compound shows activity of more than 75% of that of isoproterenol, the activity is denoted with +++, if it is between 75 and 50% it is denoted with ++; if it is between 50 and 25% it is denoted with +; if it less than 25% it is denoted with −.

Biological Example 2: Measurement of Intracellular cAMP Levels

Differentiated cells were serum-starved over night and stimulated with agonist, final concentration 1×10$^{-5}$, for 15 min in stimulation buffer (HBSS supplemented with 1% BSA, 5 mM HEPES and 1 mM IBMX, pH 7.4) The medium was then aspirated and to end the reaction 100 μL of 95% EtOH was added to each well of a 24-well plate and cells were kept in −20° C. over night. The EtOH was let to evaporate and 500 μL of lysis buffer (1% BSA, 5 mM HEPES and 0.3% Tween-20, pH 7.4) was added to each well before put in −80° C. for 30 min and then kept in −20° C. Intracellular cAMP levels were detected using an alpha screen cAMP kit (6760635D from Perkin Elmer). The activity for each compound is compared to that of isoproterenol. If a compound shows activity of more than 75% of that of isoproterenol, the activity is denoted with +++, if it is between 75 and 50% it is denoted with ++; if it is between 50 and 25% it is denoted with +; if it less than 25% it is denoted with −.

Using the assays described in Biological Examples 1 and 2 the following results were obtained.

| Compound example no. | Biological example 1 | Biological example 2 |
|---|---|---|
| 1 | + | − |
| 2 | + | − |
| 3 | + | − |
| 4 | ++ | − |
| 5 | + | − |
| 6 | + | − |
| 7 | ++ | − |
| 8 | + | − |
| 9 | + | − |
| 10 | ++ | − |
| 11 | ++ | − |
| 12 | ++ | − |
| 13 | +++ | − |
| 14 | +++ | − |
| 15 | +++ | − |
| 16 | ++ | − |
| 17 | +++ | + |
| 18 | + | − |
| 19 | +++ | − |
| 20 | + | − |
| 21 | + | − |

The invention claimed is:

1. A compound of the following formula:

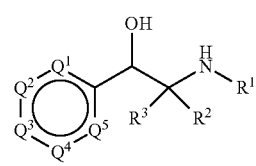

(I)

or a pharmaceutically acceptable salt thereof.

2. The compound of claim 1, or a pharmaceutically acceptable salt thereof, wherein the compound is present in an enantiomeric excess (e.e.) of at least 90%.

3. A pharmaceutical composition comprising a compound as defined in claim 1, or a pharmaceutically acceptable salt thereof, and one or more pharmaceutically acceptable adjuvant, diluent and/or carrier.

4. The pharmaceutical composition of claim 3, wherein the compound is present in an enantiomeric excess (e.e.) of at least 90%.

5. A combination product comprising:
   (a) a compound as defined in claim 1, or a pharmaceutically acceptable salt thereof; and
   (b) one or more other therapeutic agent that is useful in the treatment of hyperglycaemia or a disorder characterized by hyperglycaemia,
   wherein each of components (a) and (b) is formulated in admixture, optionally with one or more a pharmaceutically-acceptable adjuvant, diluent and/or carrier.

6. The combination product of claim 5, wherein the compound is present in an enantiomeric excess (e.e.) of at least 90%.

7. A kit-of-parts comprising:
   (a) a pharmaceutical composition comprising a compound as defined in claim 1, or a pharmaceutically acceptable salt thereof, and optionally one or more pharmaceutically acceptable adjuvant, diluent and/or carrier, and
   (b) one or more other therapeutic agent that is useful in the treatment of hyperglycaemia or a disorder characterized by hyperglycaemia, optionally in admixture with one or more pharmaceutically-acceptable adjuvant, diluent and/or carrier, which components (a) and (b) are each provided in a form that is suitable for administration in conjunction with the other.

8. The kit of claim 7, wherein the compound is present in an enantiomeric excess (e.e.) of at least 90%.

* * * * *

UNITED STATES PATENT AND TRADEMARK OFFICE
CERTIFICATE OF CORRECTION

PATENT NO. : 11,357,757 B2  
APPLICATION NO. : 16/645286  
DATED : June 14, 2022  
INVENTOR(S) : Benjamin Pelcman Page 1 of 1

It is certified that error appears in the above-identified patent and that said Letters Patent is hereby corrected as shown below:

In the Claims

In Claim 1, at Column 66, please replace the structural formula:

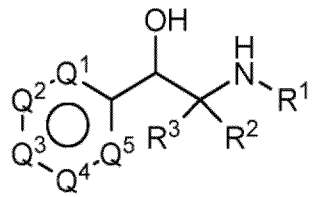

With the structural formula:

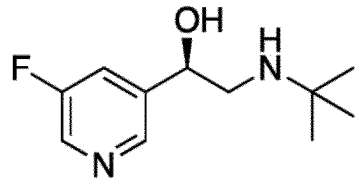

Signed and Sealed this  
Twenty-seventh Day of December, 2022

Katherine Kelly Vidal  
*Director of the United States Patent and Trademark Office*